(12) United States Patent
Thompson et al.

(10) Patent No.: US 10,121,975 B2
(45) Date of Patent: Nov. 6, 2018

(54) ORGANIC ELECTROLUMINESCENT MATERIALS AND DEVICES

(71) Applicant: University of Southern California, Los Angeles, CA (US)

(72) Inventors: Mark E. Thompson, Anaheim, CA (US); Yifei Liu, Los Angeles, CA (US); Peter I. Djurovich, Long Beach, CA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 857 days.

(21) Appl. No.: 14/302,042

(22) Filed: Jun. 11, 2014

(65) Prior Publication Data
US 2015/0008402 A1    Jan. 8, 2015

Related U.S. Application Data

(60) Provisional application No. 61/842,565, filed on Jul. 3, 2013.

(51) Int. Cl.
*H01L 51/54* (2006.01)
*C09K 11/06* (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
CPC ................................................ C09K 2211/104
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Marie R. Yamnitzky

(74) *Attorney, Agent, or Firm* — Duane Morris LLP

(57) ABSTRACT

A compound comprising a ligand $L_A$ selected from:

$L_{A1}$ $L_{A2}$ $L_{A3}$ $L_{A4}$ $L_{A5}$ $L_{A6}$ $L_{A7}$ and (Continued)

-continued

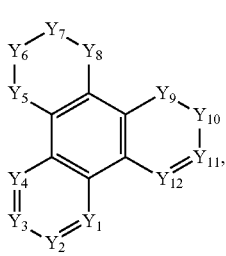

$L_{A8}$ as well as, devices and formulations containing the compound are disclosed. In the compounds, independently $X_1$-$X_6$ are CH or N; $Y_1$-$Y_{12}$ are independently selected from CH, N, and C-APR$_1$'R$_1$"; when present, exactly one of $Y_1$ through $Y_{12}$ is C-APR$_1$'R$_1$" in $L_{A8}$; A is selected from a single bond, —CR$_A$R$_B$—, —NR$_A$—, —O—, —S— and —SiR$_A$R$_B$—; and R, R$_1$', R$_1$", R$_2$, R$_3$, R$_4$, and R$_B$ are each independently a substituent selected from hydrogen, deuterium, alkyl, cycloalkyl, aryl, and combinations thereof. The P-atom of the ligand L$_A$ is bonded to a metal M having an atomic weight of at least 40.

21 Claims, 38 Drawing Sheets

(51) Int. Cl.
H01L 51/00 (2006.01)
C07F 15/00 (2006.01)
H01L 51/50 (2006.01)
(52) U.S. Cl.
CPC .......... C09K 2211/1029 (2013.01); C09K 2211/1044 (2013.01); C09K 2211/1088 (2013.01); C09K 2211/1096 (2013.01); C09K 2211/185 (2013.01); H01L 51/5016 (2013.01)

(56) References Cited

U.S. PATENT DOCUMENTS

| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,893,743 | B2 * | 5/2005 | Sato et al. .......... H01L 51/0059 257/102 |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 2002/0034656 | A1 | 3/2002 | Thompson et al. |
| 2002/0048689 | A1 * | 4/2002 | Igarashi et al. ...... C07D 213/26 428/690 |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0152802 | A1 | 8/2003 | Tsuboyama et al. |
| 2003/0162053 | A1 | 8/2003 | Marks et al. |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0137267 | A1 | 7/2004 | Igarashi et al. |
| 2004/0137268 | A1 | 7/2004 | Igarashi et al. |
| 2004/0174116 | A1 | 9/2004 | Lu et al. |
| 2005/0014024 | A1 * | 1/2005 | Tsuboyama et al. ... C07F 1/005 428/690 |
| 2005/0025993 | A1 | 2/2005 | Thompson et al. |
| 2005/0112407 | A1 | 5/2005 | Ogasawara et al. |
| 2005/0238919 | A1 | 10/2005 | Ogasawara |
| 2005/0244673 | A1 | 11/2005 | Satoh et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0202194 | A1 | 9/2006 | Jeong et al. |
| 2006/0240279 | A1 | 10/2006 | Adamovich et al. |
| 2006/0251923 | A1 | 11/2006 | Lin et al. |
| 2006/0263635 | A1 | 11/2006 | Ise |
| 2006/0280965 | A1 | 12/2006 | Kwong et al. |
| 2007/0190359 | A1 | 8/2007 | Knowles et al. |
| 2007/0278938 | A1 | 12/2007 | Yabunouchi et al. |
| 2008/0015355 | A1 | 1/2008 | Schafer et al. |
| 2008/0018221 | A1 | 1/2008 | Egen et al. |
| 2008/0106190 | A1 | 5/2008 | Yabunouchi et al. |
| 2008/0124572 | A1 | 5/2008 | Mizuki et al. |
| 2008/0220265 | A1 | 9/2008 | Xia et al. |
| 2008/0297033 | A1 | 12/2008 | Knowles et al. |
| 2009/0008605 | A1 | 1/2009 | Kawamura et al. |
| 2009/0009065 | A1 | 1/2009 | Nishimura et al. |
| 2009/0017330 | A1 | 1/2009 | Iwakuma et al. |
| 2009/0030202 | A1 | 1/2009 | Iwakuma et al. |
| 2009/0039776 | A1 | 2/2009 | Yamada et al. |
| 2009/0045730 | A1 | 2/2009 | Nishimura et al. |
| 2009/0045731 | A1 | 2/2009 | Nishimura et al. |
| 2009/0101870 | A1 | 4/2009 | Prakash et al. |
| 2009/0108737 | A1 | 4/2009 | Kwong et al. |
| 2009/0115316 | A1 | 5/2009 | Zheng et al. |
| 2009/0115324 | A1 * | 5/2009 | Hashimoto et al. ......... C07F 15/0086 313/504 |
| 2009/0165846 | A1 | 7/2009 | Johannes et al. |
| 2009/0167162 | A1 | 7/2009 | Lin et al. |
| 2009/0179554 | A1 | 7/2009 | Kuma et al. |
| 2009/0209756 | A1 * | 8/2009 | Chi et al. ............ C07F 15/0033 544/225 |
| 2012/0187349 | A1 * | 7/2012 | Stoessel et al. .... C07F 15/0086 252/519.2 |
| 2015/0076454 | A1 * | 3/2015 | Tsai .................... H01L 51/0088 257/40 |
| 2015/0280147 | A1 * | 10/2015 | Wesemann et al. ... C09K 11/06 252/301.16 |
| 2015/0280150 | A1 * | 10/2015 | Wesemann et al. ......... H01L 51/0059 257/40 |

FOREIGN PATENT DOCUMENTS

| EP | 2034538 | | 3/2009 |
| JP | 2002-170684 | A * | 6/2002 |
| JP | 200511610 | | 1/2005 |
| JP | 2007123392 | | 5/2007 |
| JP | 2007254297 | | 10/2007 |
| JP | 2008074939 | | 4/2008 |
| WO | 2001039234 | | 5/2001 |
| WO | 2002002714 | | 1/2002 |
| WO | 200215645 | | 2/2002 |

(56) References Cited

FOREIGN PATENT DOCUMENTS

| WO | 2003040257 | 5/2003 |
| --- | --- | --- |
| WO | 2003060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | WO 2011/035836 A1 * | 3/2011 |
| WO | WO 2014/067598 A1 * | 5/2014 |
| WO | WO 2014/067617 A1 * | 5/2014 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3, (2007).

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhicliang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1:15-20 (2000).

Hamada, Yuji et al., "High Luminance in Organic Electroluminescent Devices with Bis(10-hydroxybenzo[h]quinolinato) beryllium as an Emitter, " Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

(56) References Cited

OTHER PUBLICATIONS

Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91:209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Orgnic LIght-Emitting Diodes with Phosphorescent Platinum Complexes Containing NCN-Coordinting Tridentate Lignd," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Chiu, Y.C., et al., "Blue to True-Blue Phosphorescent Ir-(III) Complexes Bearing a Nonconjugated Ancillary Phosphine Chelate: Strategic Synthesis, Photophysics, and Device Integration," ACS Applied Materials & Interfaces, 1 (2009), 433-42.
Hung, J.Y., et al., "Blue-Emitting Ir(III)Phosphors with Ancillary 4,6-Difluorobenzyl Diphenylphosphine Based Cyclometalate," Dalton Transactions (2009), 6472-75.
Lee, T. C., et al., "Syntheses, Photophysics, and Application of Iridium(III) Phosphorescent Emitters for Highly Efficient, Long-Life Organic Light-Emitting Diodes," Chemistry—an Asian Journal, 4 (2009), 742-53.
Lin, C. H., et al., "Heteroleptic Ir(III) Complexes Containing Both Azolate Chromophoric Chelate and Diphenylphosphinoaryl Cyclometalates; Reactivities, Electronic Properties and Applications," Dalton Transactions, 40 (2011), 1132-43.
Lin, C. H., et al., "Stepwise Formation of Iridium(III) Complexes with Monocyclometalating and Dicyclometalating Phosphorus Chelates," Inorganic Chemistry, 51 (2012), 1785-95.

* cited by examiner

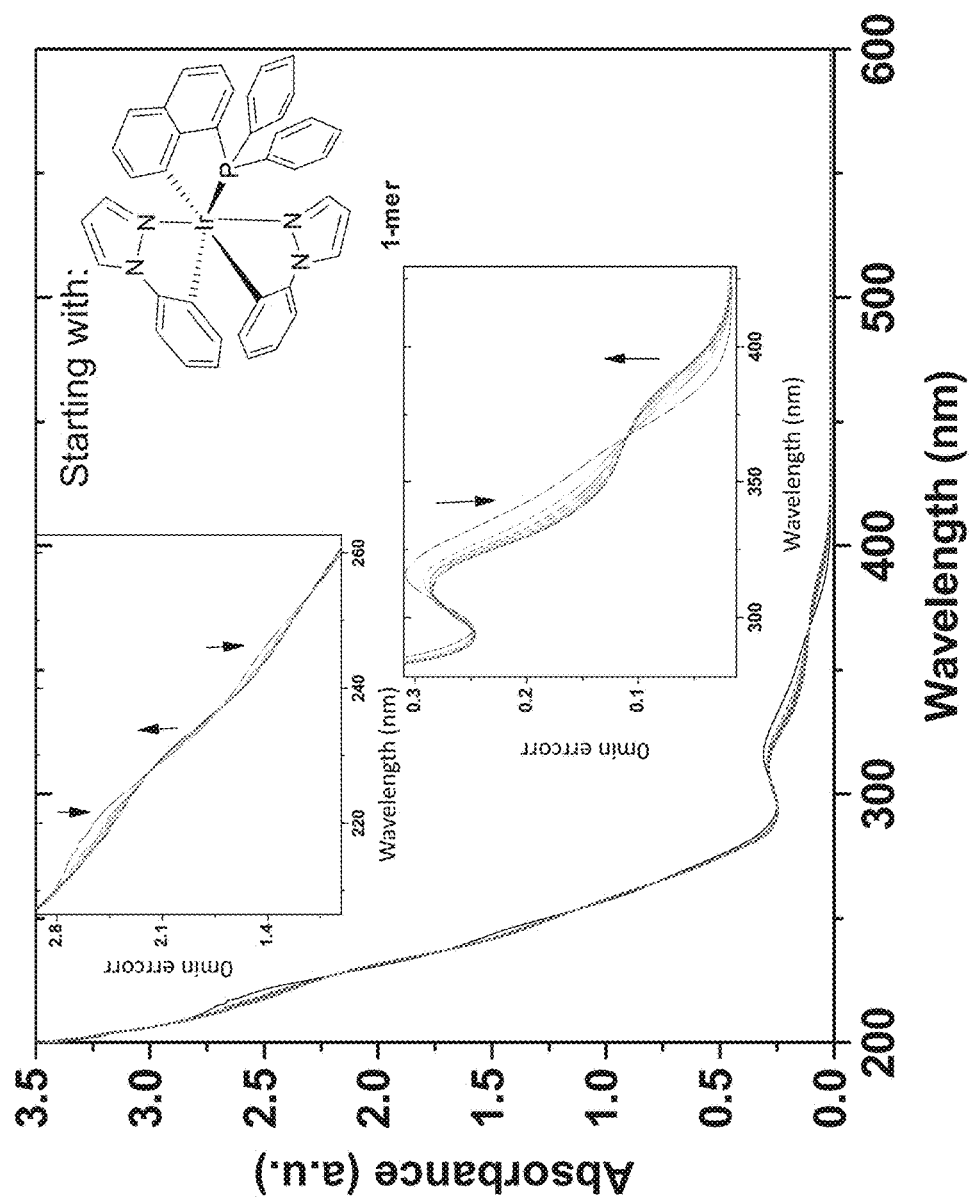
FIG. 6.1

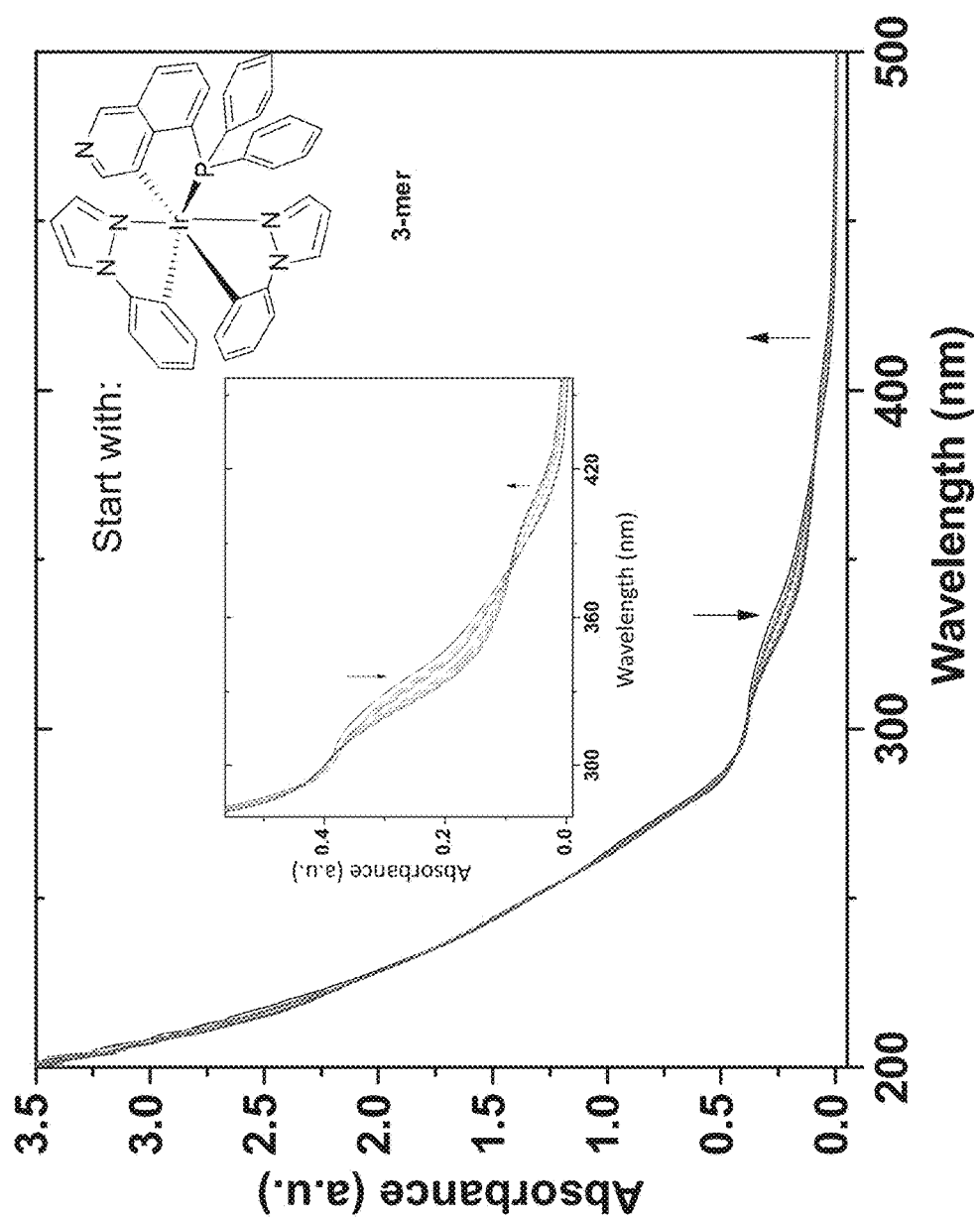
FIG. 6.2

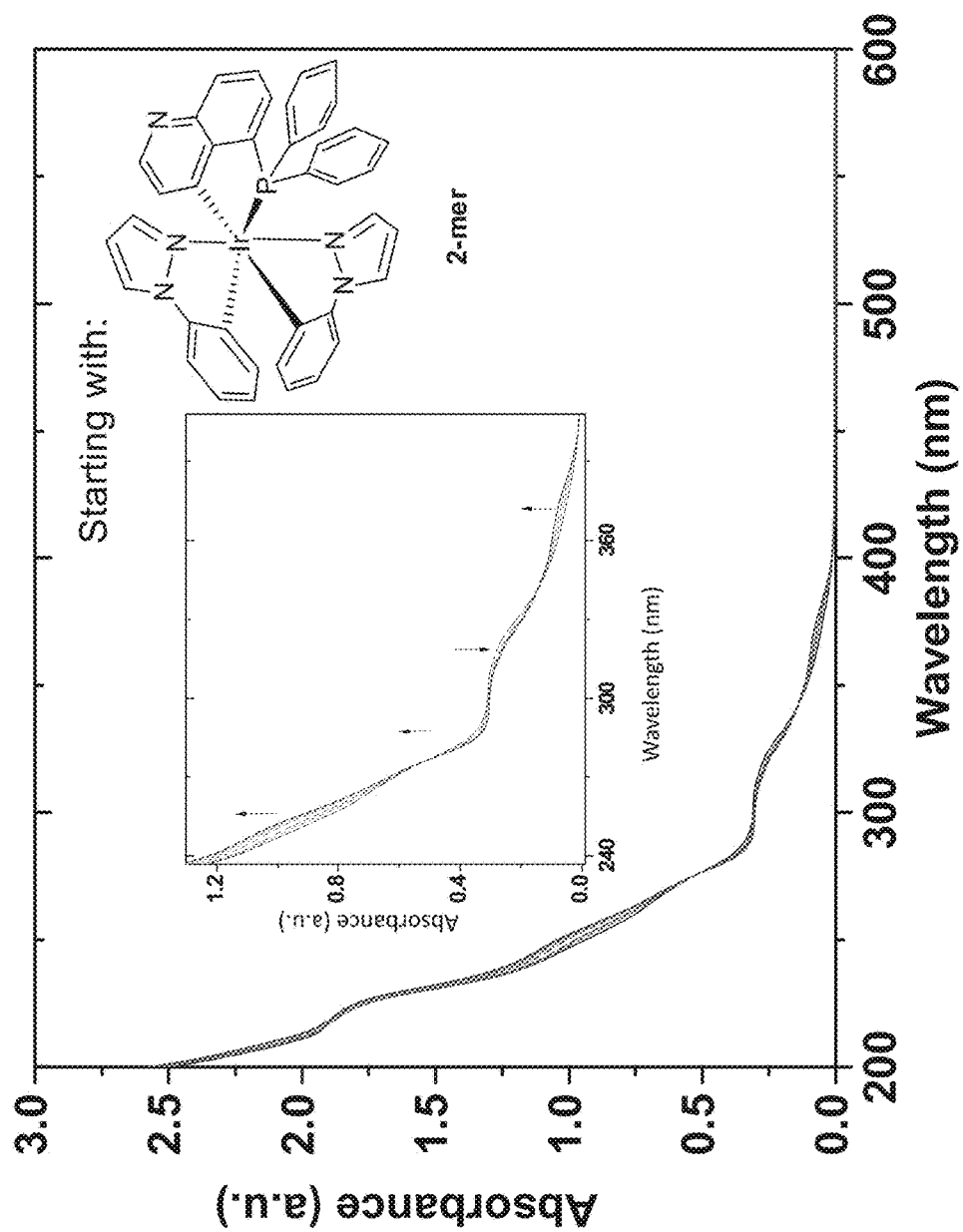
FIG. 6.3

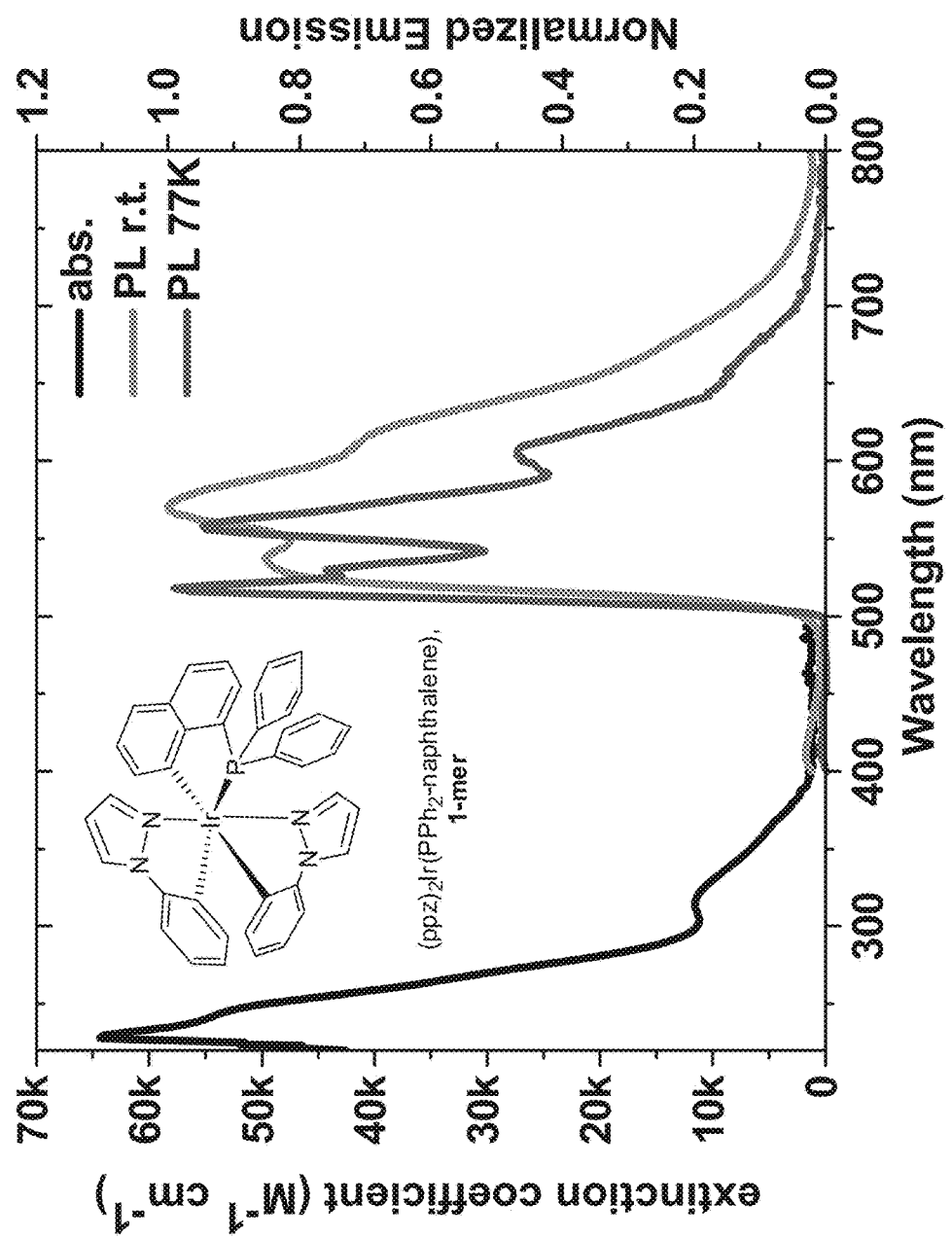
FIG. 8.1

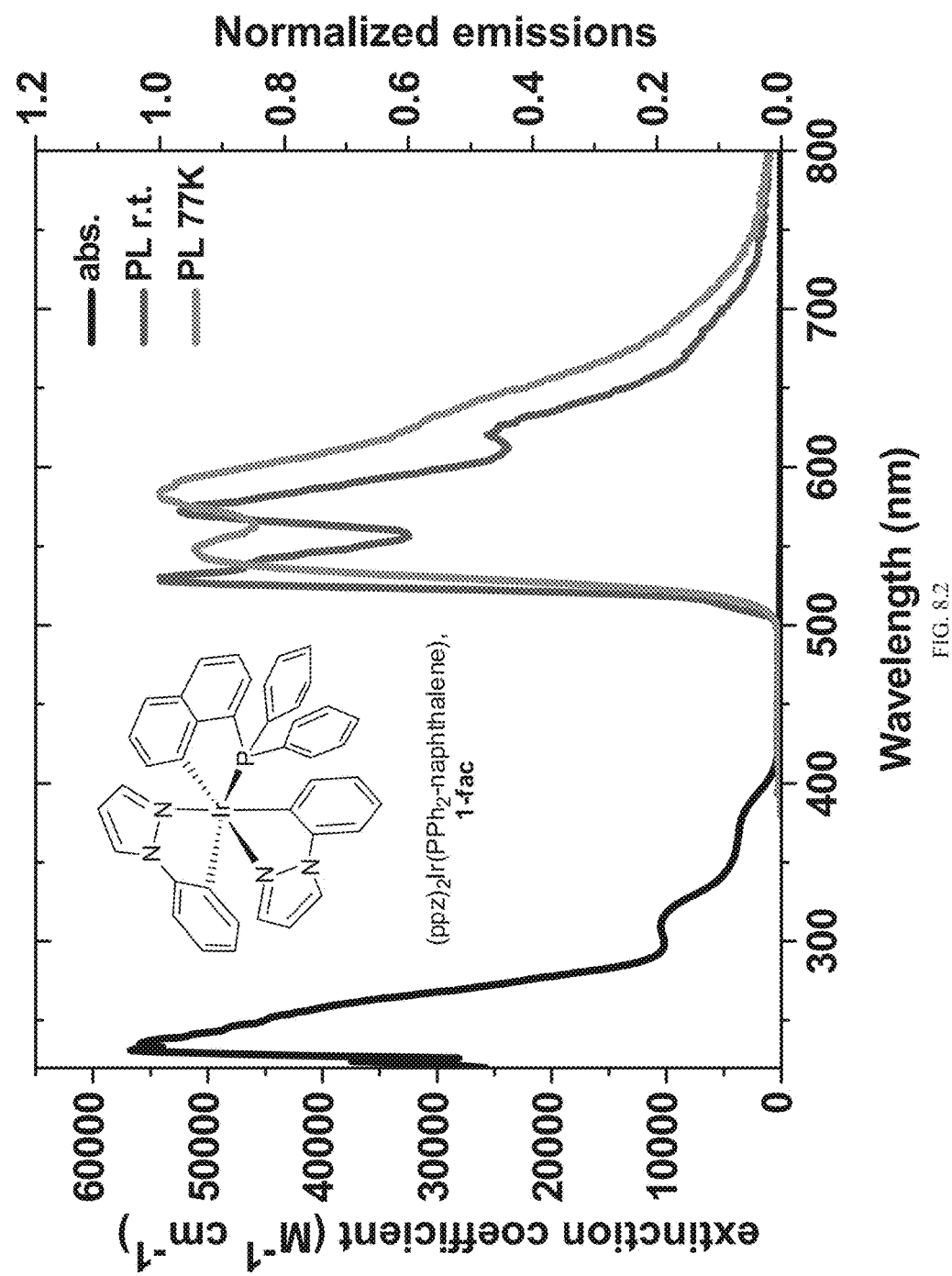
FIG. 8.2

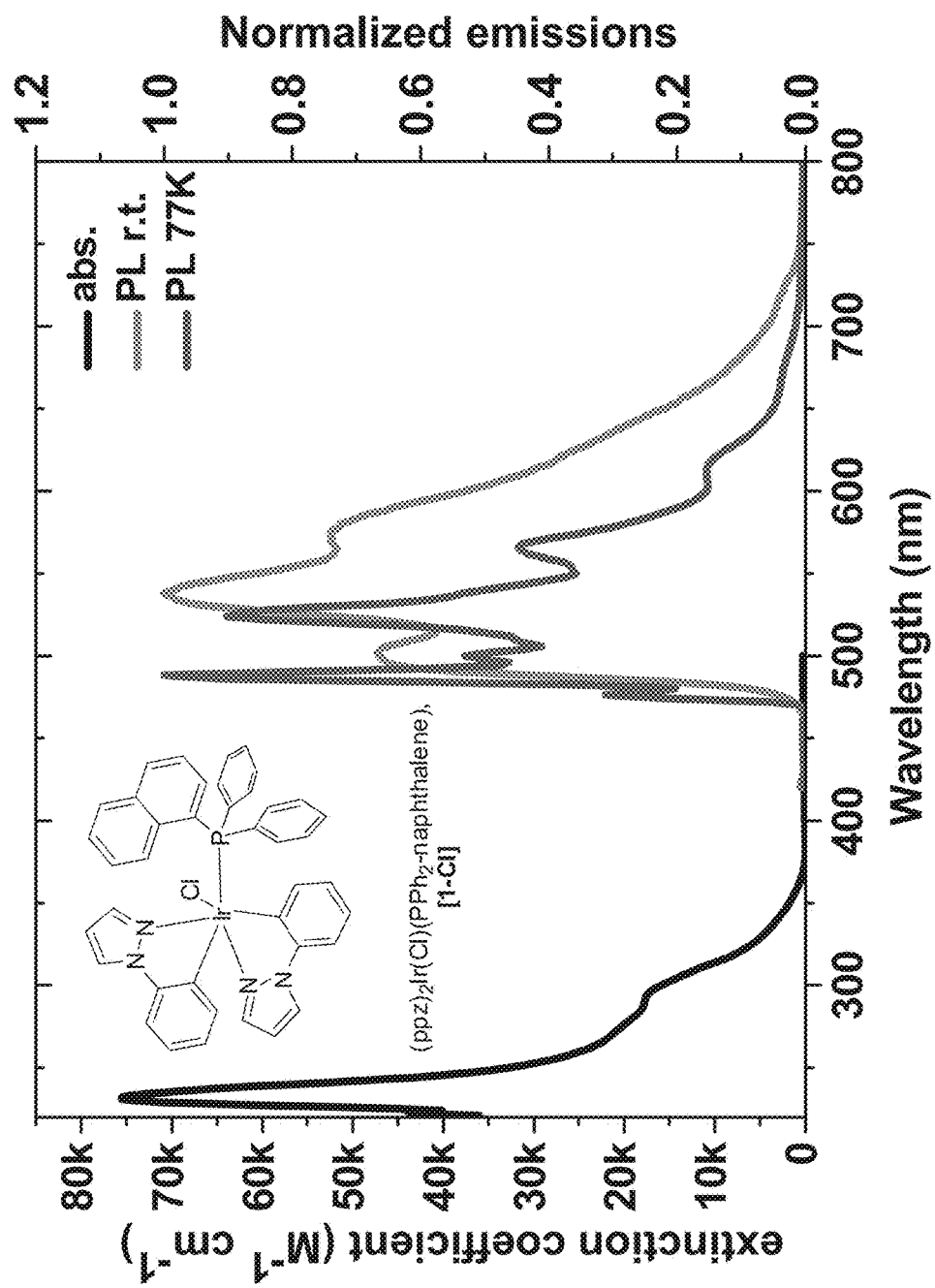
FIG. 8.3

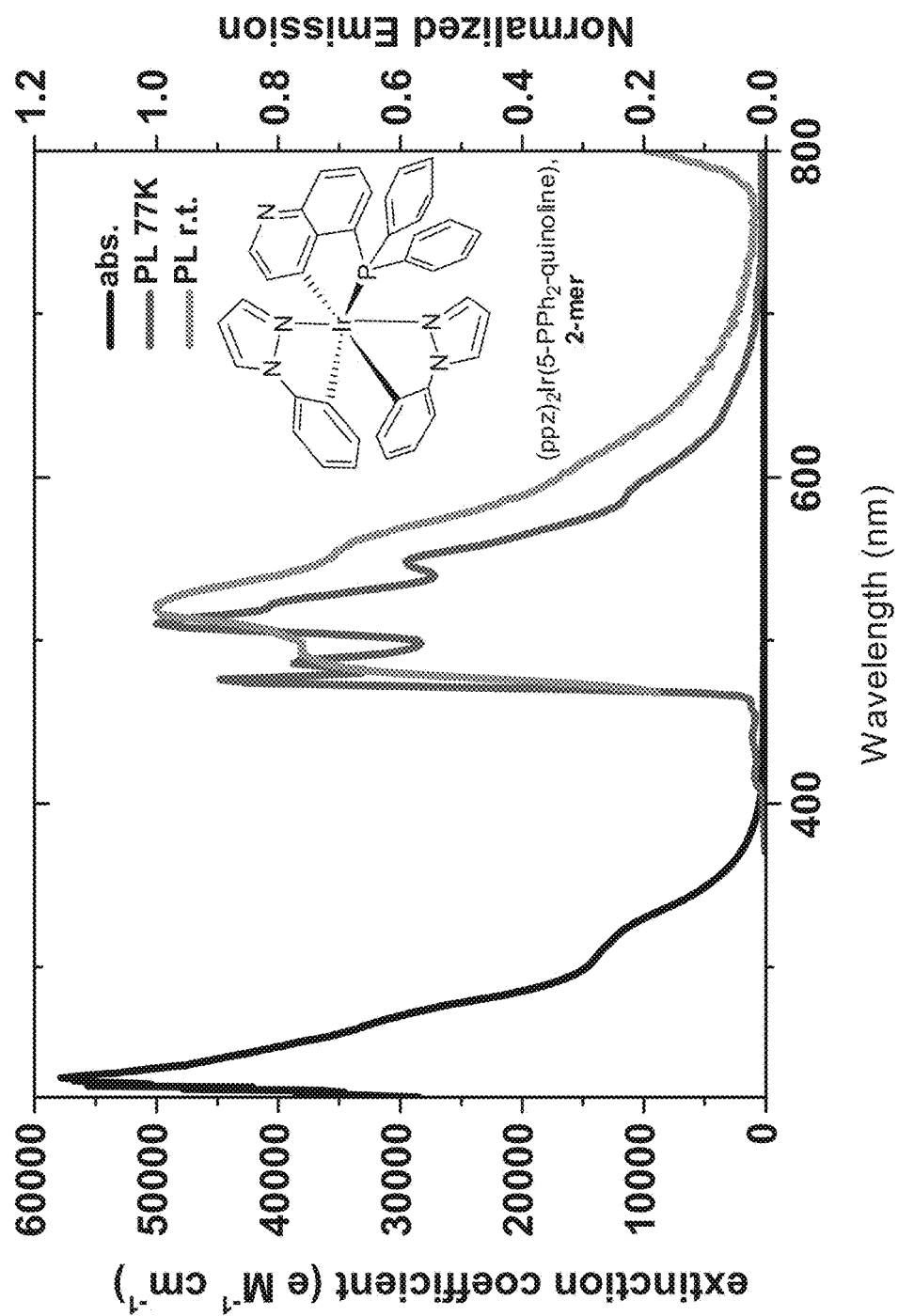
FIG. 9.1

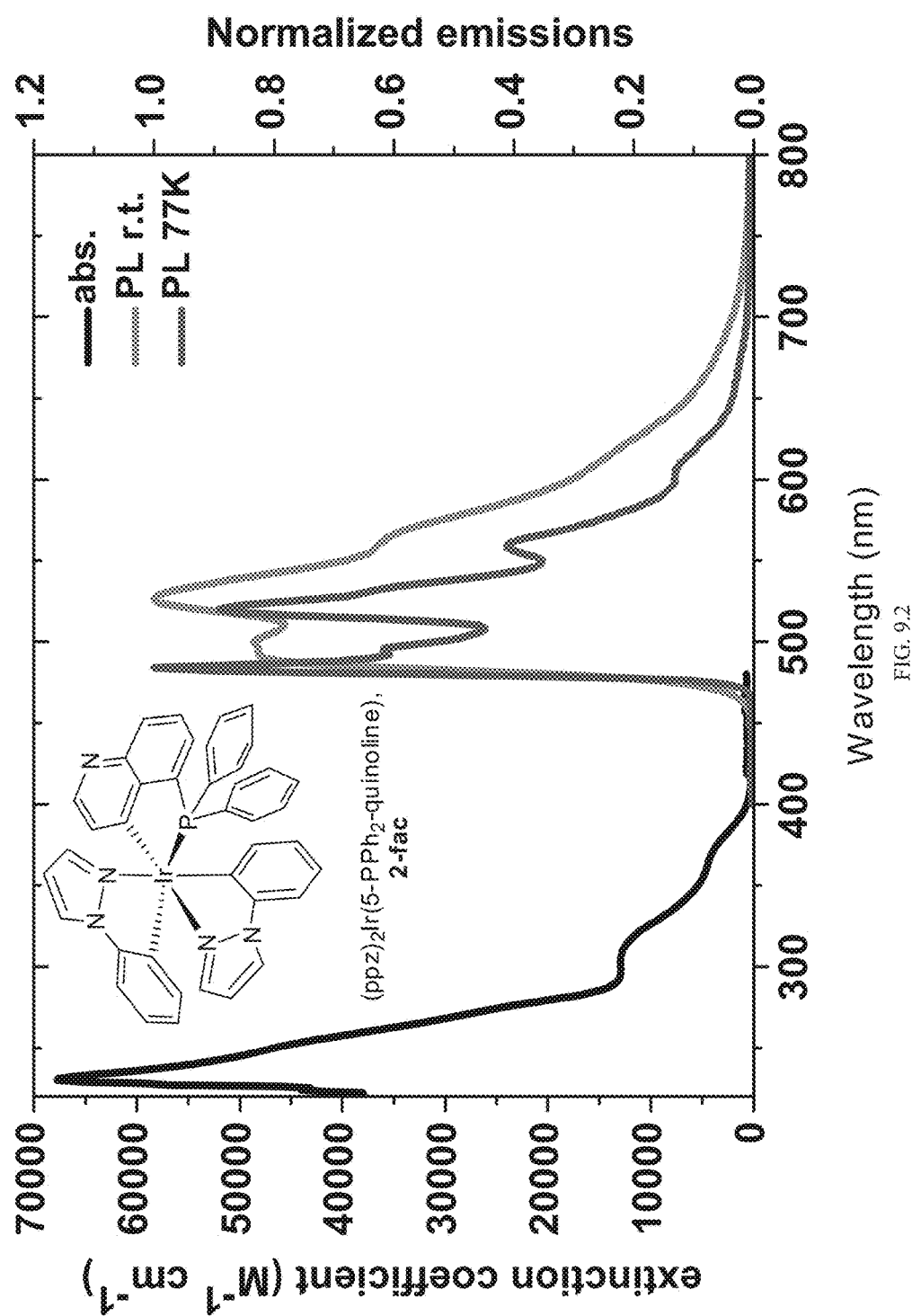
FIG. 9.2

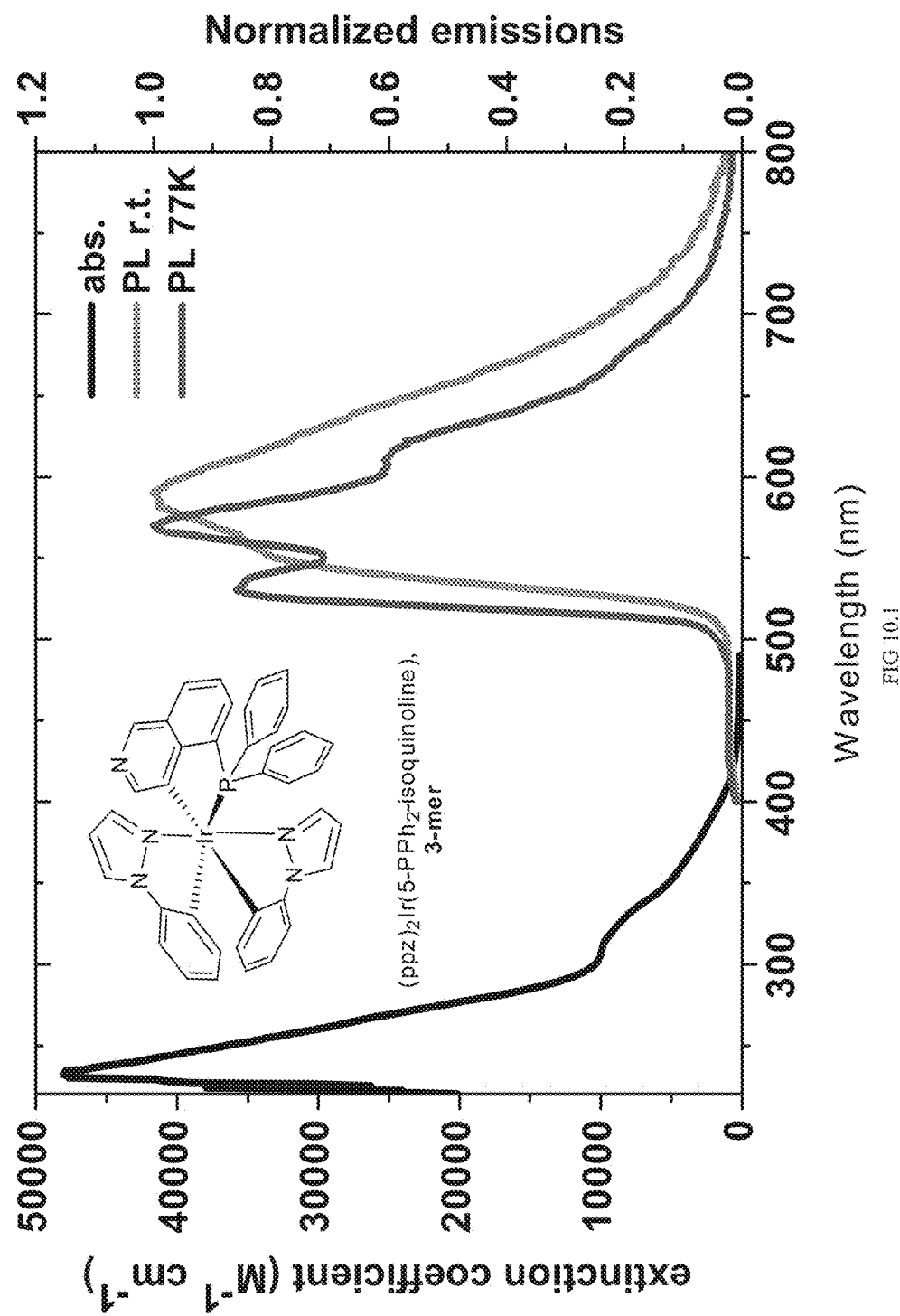
FIG 10.1

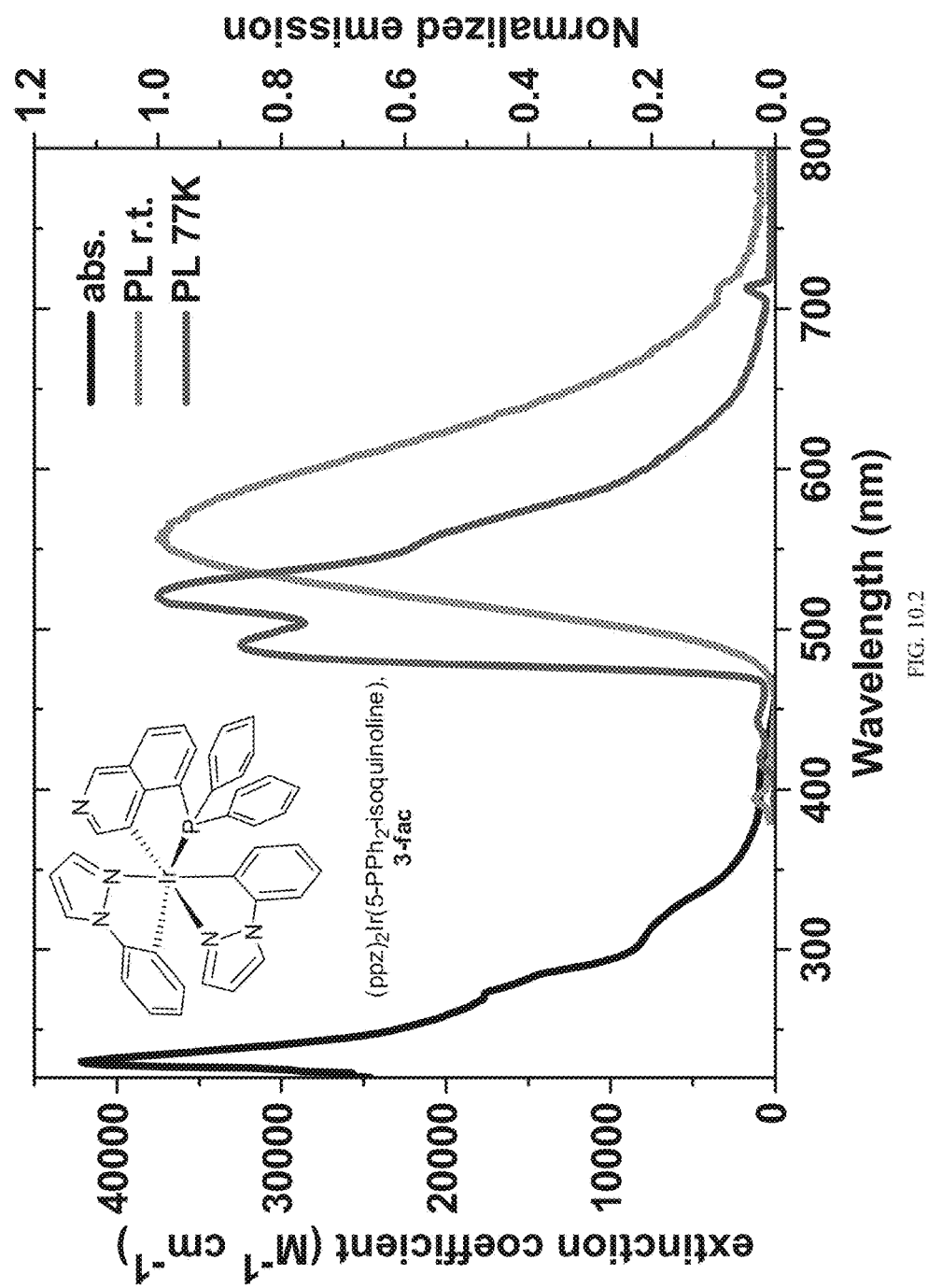
FIG. 10.2

ORGANIC ELECTROLUMINESCENT MATERIALS AND DEVICES

CROSS-REFERENCE TO RELATED APPLICATIONS

This application claims priority to U.S. Provisional Patent Application Ser. No. 61/842,565, filed Jul. 3, 2013, the entire contents of which is incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds for use as emitters and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

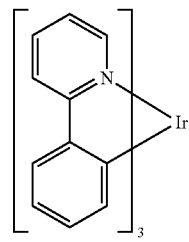

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer.

For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

3

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to one embodiment, a compound comprising a ligand $L_A$ selected from the group consisting of:

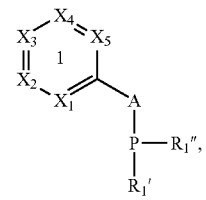
$L_{A1}$

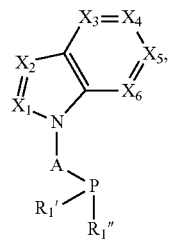
$L_{A2}$

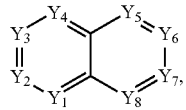
$L_{A3}$

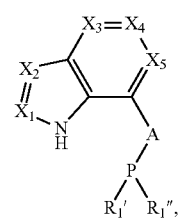
$L_{A4}$

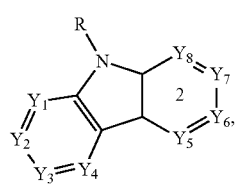
$L_{A5}$

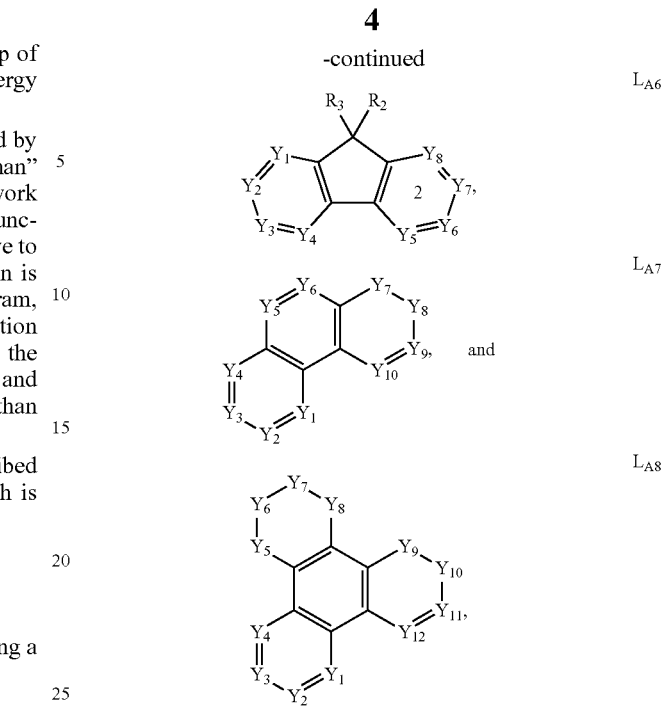
$L_{A6}$ $L_{A7}$ and $L_{A8}$ is disclosed.

In the ligand $L_A$:

$X_1$, $X_2$, $X_3$, $X_4$, $X_5$, and $X_6$ are independently selected from the group consisting of CH and N;

$Y_1$, $Y_2$, $Y_3$, $Y_4$, $Y_5$, $Y_6$, $Y_7$, $Y_8$, $Y_9$, $Y_{10}$, $Y_{11}$, and $Y_{12}$ are independently selected from the group consisting of CH, N, and C-APR$_1$'R$_1$", exactly one of $Y_1$ through $Y_8$ is C-APR$_1$'R$_1$" in $L_{A3}$, $L_{A5}$, and $L_{A6}$;

exactly one of $Y_1$ through $Y_{10}$ is C-APR$_1$'R$_1$" in $L_{A7}$;

exactly one of $Y_1$ through $Y_{12}$ is C-APR$_1$'R$_1$" in $L_{A8}$;

A is selected from the group consisting of a single bond, —CR$_A$R$_B$—, —NR$_A$—, —O—, —S— and —SiR$_A$R$_B$—;

R, R$_1$', R$_1$", R$_2$, R$_3$, R$_A$, and R$_B$ are each independently a substitutent selected from the group consisting of hydrogen, deuterium, alkyl, cycloalkyl, aryl, and combinations thereof;

adjacent substituents of R$_1$, R$_2$ or R$_3$ are optionally joined to form a fused ring;

a P-atom of the ligand $L_A$ is bonded to a metal M having an atomic weight of at least 40; and the ligand $L_A$ is optionally linked with other ligands to comprise a bidentate, tridentate, tetradentate, pentadentate or hexadentate ligand.

According to another embodiment, a first device comprising a first organic light emitting device is also provided. The first organic light emitting device can include an anode, a cathode, and an organic layer, disposed between the anode and the cathode. The organic layer can include a compound that includes the ligand $L_A$. The first device can be a consumer product, an organic light-emitting device, and/or a lighting panel.

According to another embodiments, a formulation containing a compound that includes the ligand $L_A$ is disclosed.

BRIEF DESCRIPTION OF THE DRAWINGS

FIGS. 6.1, 6.2 and 6.3 show wavelength versus absorbance data for photo-isomerisation of Complexes (1-mer→1-fac), (2-mer→2-fac), and (3-mer→3-fac) in acetonitrile.

FIGS. 8.1, 8.2 and 8.3 show absorption and emission spectra of 1-mer (FIG. 8.1) and 1-fac (FIG. 8.2) and 1-Cl (FIG. 8.3).

FIGS. 9.1 and 9.2 show absorption and emission spectra of 2-mer (FIG. 9.1) and 2-fac (FIG. 9.2).

FIGS. 10.1 and 10.2 show absorption and emission spectra of 3-mer (FIG. 10.1) and 3-fac (FIG. 10.2).

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
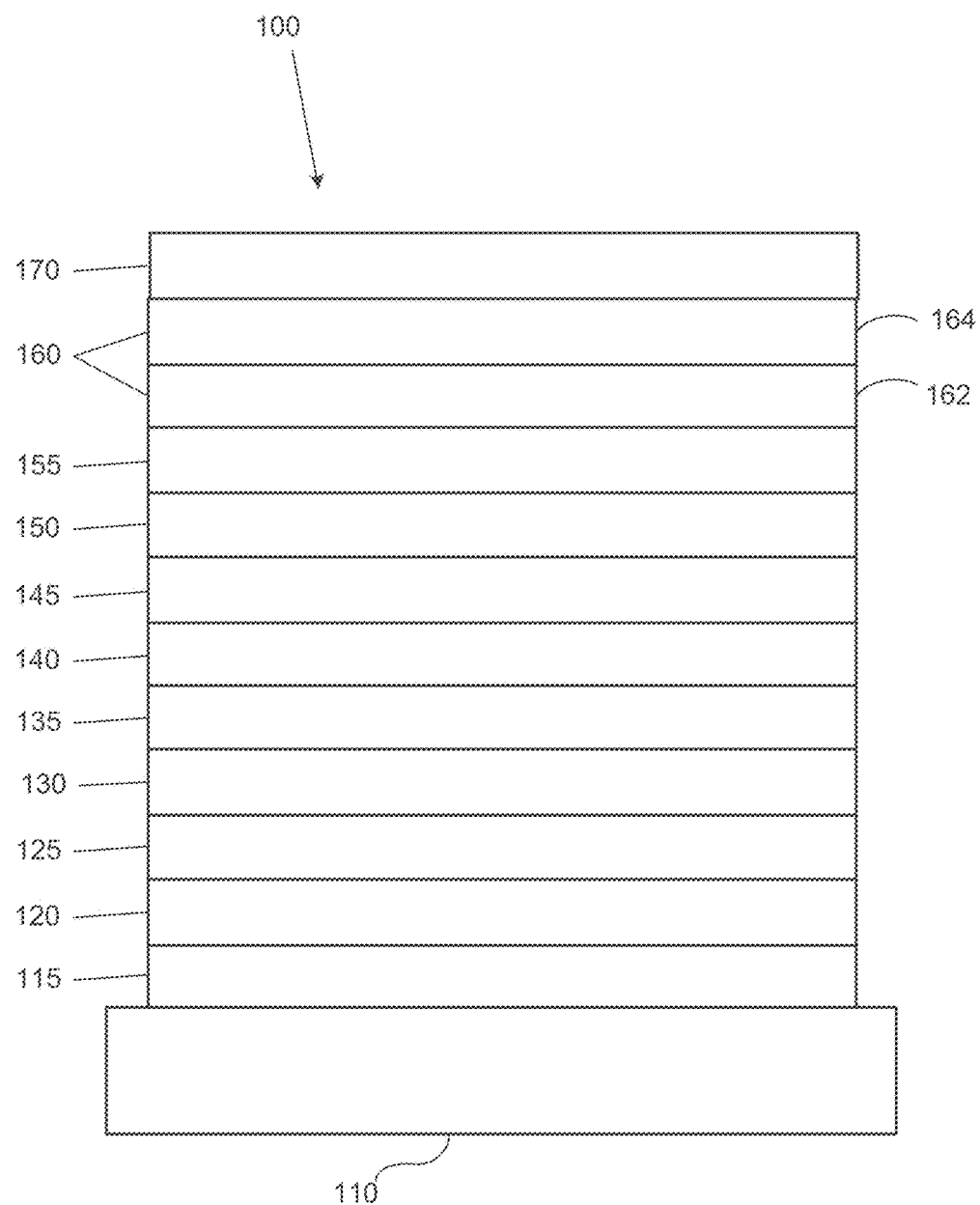
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F$_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
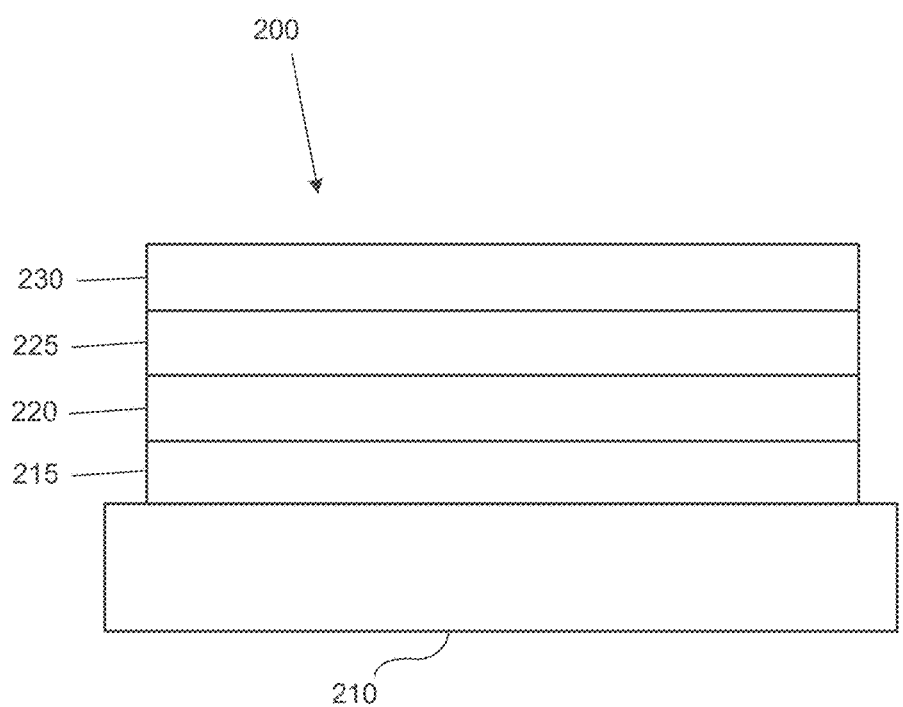
FIG. 2 shows an inverted organic light emitting device that does not have a separate electron transport layer.
Figure 3:
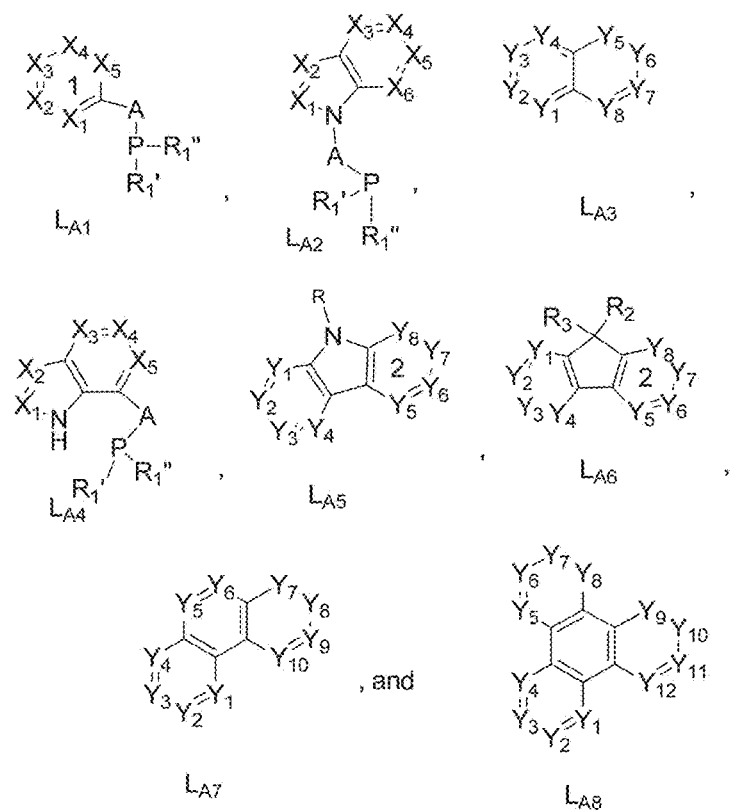
FIG. 3 shows Formula I as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo" or "halogen" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like.

The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[fh]quinoxaline and dibenzo[fh]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. naphthyl, dibenzofuryl) or as if it were the whole molecule (e.g. naphthalene, dibenzofuran). As used herein, these different ways of designating a substituent or attached fragment are considered to be equivalent.

A series of metal complexes (e.g., Ir(III)) containing phosphinoaryl cyclometalates of (C^P) chelates have been developed. While not wishing ot be bound by theory, it is believed that the phosphorescence of the complexes originates from the aryl group in the phosphinoaryl chelates. The C^P ligands can be designed with high or low triplet energies, which give the excited states substantial metal-to-ligand charge-transfer (MLCT) character. This allows turning of the phosphorescence of the metal complexes from deep blue to red. The design of heteroleptic metal complexes with phosphinoaryl ligand of varied triplet energies can lead to RGB phosphors to fulfill the demand of full-color OLED display. As used herein, designations like "C^P" and "C^N" are used to designate the atoms that complex with the metal core.

According to one embodiment, a compound comprising a ligand $L_A$ selected from the group consisting of:

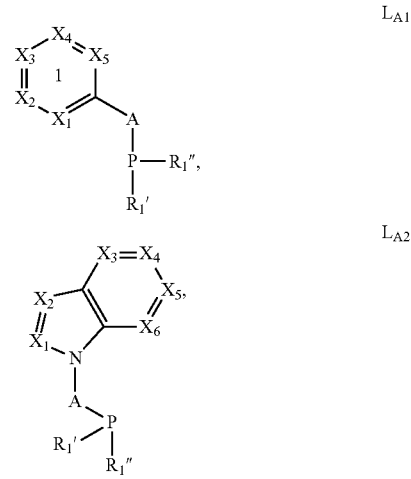

-continued

L_{A3} 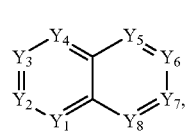

L_{A4} 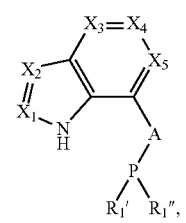

L_{A5} 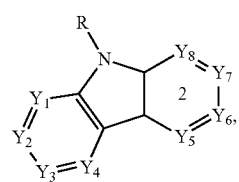

L_{A6} 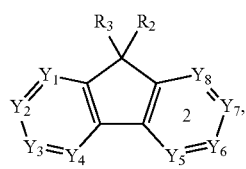

L_{A7} 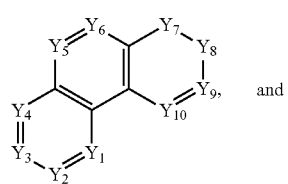

and

L_{A8} 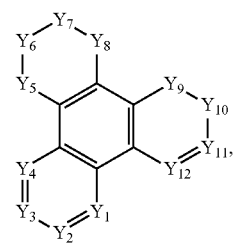

is disclosed.

In the ligand $L_A$:

$X_1$, $X_2$, $X_3$, $X_4$, $X_5$, and $X_6$ are independently selected from the group consisting of CH and N;

$Y_1$, $Y_2$, $Y_3$, $Y_4$, $Y_5$, $Y_6$, $Y_7$, $Y_8$, $Y_9$, $Y_{10}$, $Y_{11}$, and $Y_{12}$ are independently selected from the group consisting of CH, N, and C-APR$_1'$R$_1''$, exactly one of $Y_1$ through $Y_8$ is C-APR$_1'$R$_1''$ in $L_{A3}$, $L_{A5}$, and $L_{A6}$;

exactly one of $Y_1$ through $Y_{10}$ is C-APR$_1'$R$_1''$ in $L_{A7}$;

exactly one of $Y_1$ through $Y_{12}$ is C-APR$_1'$R$_1''$ in $L_{A8}$;

A is selected from the group consisting of a single bond, —CR$_A$R$_B$—, —NR$_A$—, —O—, —S— and —SiR$_A$R$_B$—;

R, R$_1'$, R$_1''$, R$_2$, R$_3$, R$_A$, and R$_B$ are each independently a substitutent selected from the group consisting of hydrogen, deuterium, alkyl, cycloalkyl, aryl, and combinations thereof;

adjacent substituents of R$_1$, R$_2$ or R$_3$ are optionally joined to form a fused ring;

a P-atom of the ligand $L_A$ is bonded to a metal M having an atomic weight of at least 40; and the ligand $L_A$ is optionally linked with other ligands to comprise a bidentate, tridentate, tetradentate, pentadentate or hexadentate ligand.

In embodiments, the ligand $L_A$ is at least bidentate and a second bond between the metal and the ligand $L_A$ is formed by:

any carbon atom of Ring 1 of ligand $L_{A1}$, a carbon atom at position $X_1$ or $X_2$ or $X_6$ of ligand $L_{A2}$, a carbon atom of ligand $L_{A3}$, ligand $L_{A5}$, ligand $L_{A6}$, ligand $L_{A7}$, ligand $L_{A7}$, or ligand $L_{A8}$, or a nitrogen atom in the bicyclic ring of ligand $L_{A4}$.

In some embodiments, the second bond between the metal and ligand $L_{A5}$ or ligand $L_{A6}$ can be formed by any carbon atom of Ring 2. In some embodiments, the ligand is ligand $L_{A5}$ or ligand $L_{A6}$, exactly one of $Y_5$ through $Y_8$ is C-APR$_1'$R$_1''$, and the second bond between the metal and ligand $L_{A5}$ or ligand $L_{A6}$ can be formed by any carbon atom of Ring 2

In a more specific embodiment, a compound comprising a ligand $L_A$ selected from the group consisting of:

L_{A1-1} 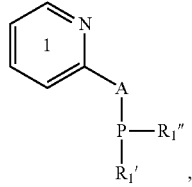

L_{A1-2} 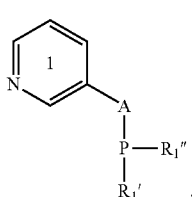

L_{A1-3} 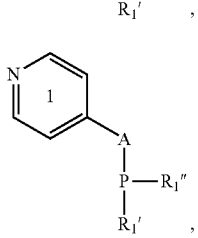

L_{A2-1} 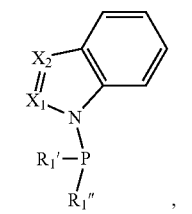

L_{A2-2} 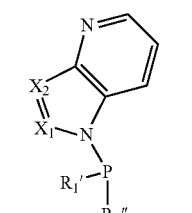

$L_{A2-3}$
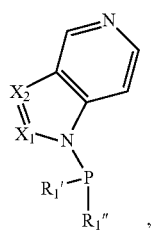

$L_{A2-4}$
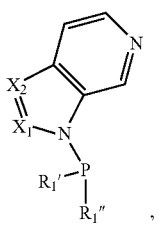

$L_{A3-1}$
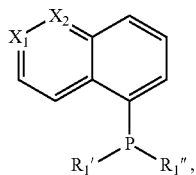

$L_{A4-1}$
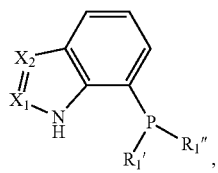

$L_{A4-2}$
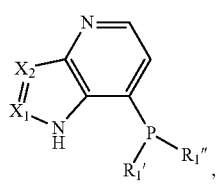

$L_{A4-3}$
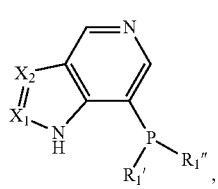

$L_{A4-4}$
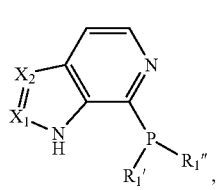

$L_{A5-1}$
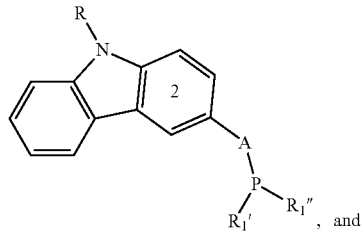

and $L_{A6-1}$
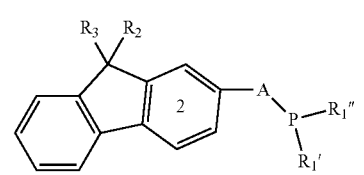

is disclosed.

In the compound, $L_A$ is at least bidentate if the ligand $L_A$ is selected from the group consisting of $L_{A1-1}$, $L_{A1-3}$, $L_{A2-1}$, $L_{A3-1}$, and $L_{A4-1}$.

In some embodiments, $L_A$ is exactly bidentate. In some embodiments, $L_A$ is at least bidentate. In some embodiments, $L_A$ is at least bidentate if the ligand $L_A$ is selected from the group consisting of $L_{A1}$, $L_{A2}$, $L_{A3}$, and $L_{A4}$ In some embodiments, M is selected from the group consisting of Ir, Rh, Re, Ru, Os, Pt, Au, and Cu. In some embodiments, M is Ir.

In some embodiments, $L_A$ is exactly monodentate. In some embodiments, $L_A$ is exactly bidentate, or exactly tridentate, or exactly tetradentate, or exactly pentadentate, or exactly hexadentate ligand. As used herein, "exactly" plus a particular denticity means that the ligand is not further linked to other ligand to produce a ligand of higher denticity.

In some embodiments, the ligand $L_A$ is at least bidentate and a second bond between the metal and the ligand $L_A$ is formed by:

any carbon atom of pyrydinyl Ring 1 of the ligands $L_{A1-1}$, $L_{A1-2}$ and $L_{A1-3}$, a carbon atom at the position $X_1$ or $X_2$ of the ligands $L_{A2-1}$, $L_{A2-2}$, $L_{A2-3}$, and $L_{A2-4}$, a carbon atom para to the position $X_2$ of the ligand $L_{A3-1}$, by a nitrogen atom in the bicyclic ring of the ligands $L_{A4-1}$, $L_{A4-2}$, $L_{A4-3}$, and $L_{A4-4}$, where the nitrogen atom is adjacent to the position $X_1$, or by any carbon atom of Ring 2 of the ligands $L_{A5-1}$ and $L_{A6-1}$.

In some embodiments, the ligand $L_A$ is selected from the group consisting of:

$L_{A5-1}$
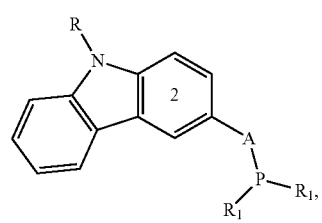

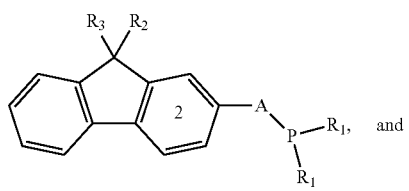

$L_{A6-1}$

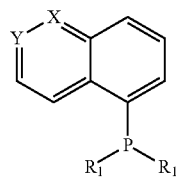

$L_{A3-1}$

In some such embodiments, the ligand $L_A$ is bidentate, and a C-atom of said carbazole group, said fluorene group, or said naphthalene group, is coordinated to a metal M.

In some embodiments, the compound has the formula $M(L_A)_m(L_B)_n$, wherein $L_B$ is a different ligand from $L_A$; m is an integer from 1 to the maximum number of ligands that may be coordinated to the metal M; and m+n is the the maximum number of ligands that may be coordinated to the metal M. In some embodiments, m is 1 and n is 2. In some such embodiments, m is 1 or 2; and the ligand $L_B$ is selected from the group consisting of:

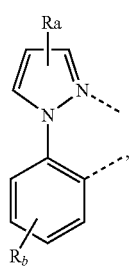

$L_{B1}$

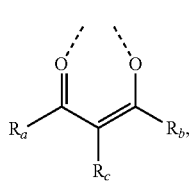

$L_{B2}$

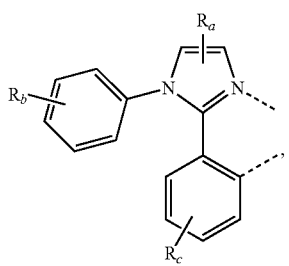

$L_{B3}$

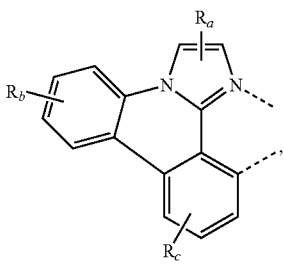

$L_{B4}$

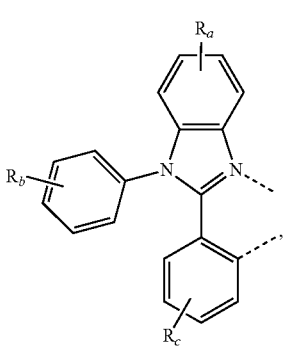

$L_{B5}$

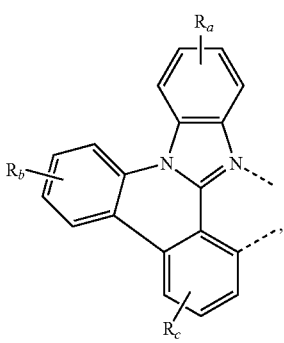

$L_{B6}$

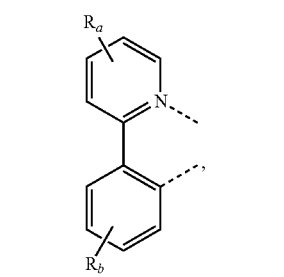

$L_{B7}$

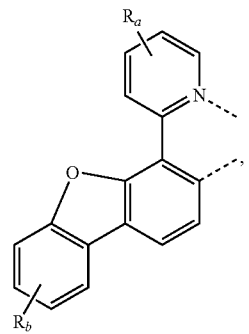

$L_{B8}$

17
-continued
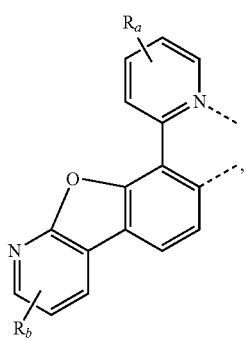
L_B9
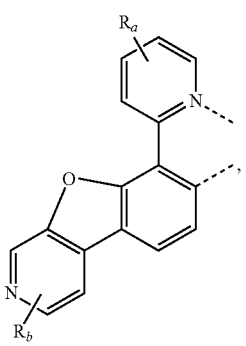
L_B10
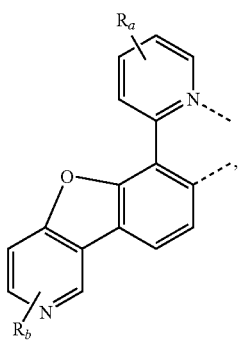
L_B12
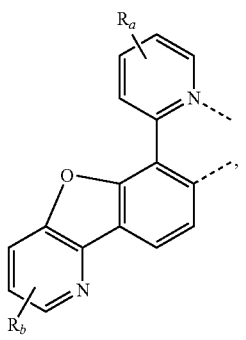
L_B13
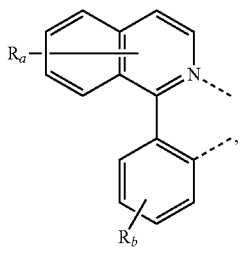
L_B14
18
-continued
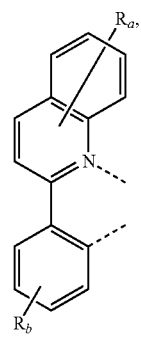
L_B15
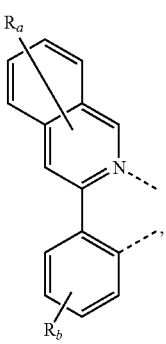
L_B16
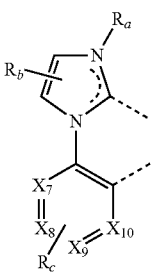
L_B17
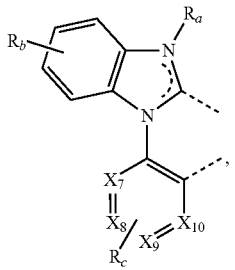
L_B18
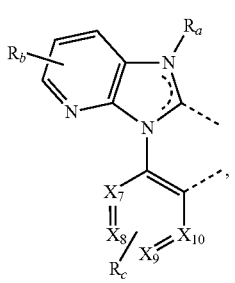
L_B19

-continued

L<sub>B20</sub>
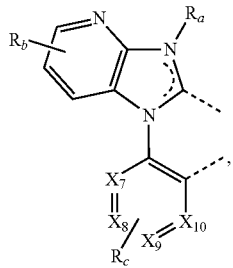

L<sub>B21</sub>
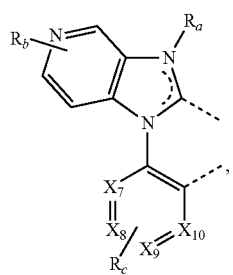

L<sub>B22</sub>
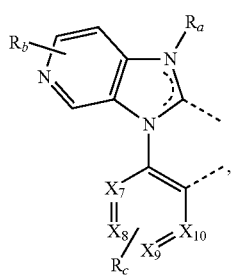

L<sub>B23</sub>
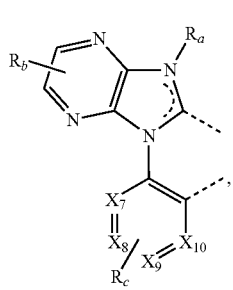

L<sub>B24</sub>
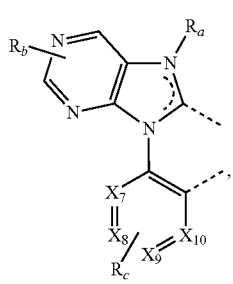

-continued

L<sub>B25</sub>
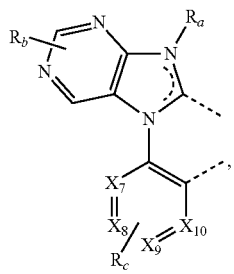

L<sub>B26</sub>
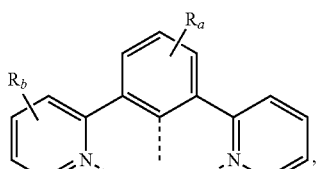

L<sub>B27</sub>
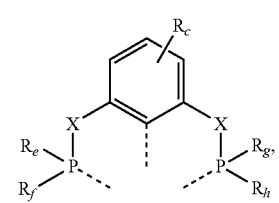

L<sub>B28</sub>
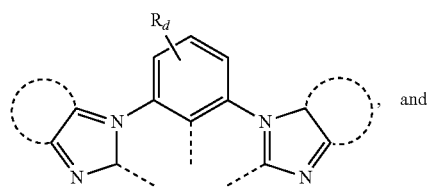, and

L<sub>B29</sub>
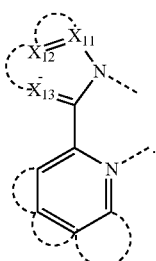

In the formulas of ligand L$_B$:

$X_7$, $X_8$, $X_9$, and $X_{10}$ are independently selected from the group consisting of CH, and N;

$X_{11}$, $X_{12}$, and $X_{13}$ are independently selected from the group consisting of CH, CR', and N;

$R_a$, $R_b$, $R_c$, and $R_d$ may represent mono, di, tri, or tetra substitution, or no substitution;

R', $R_a$, $R_b$, $R_c$, $R_d$, $R_e$, $R_f$, $R_g$, and $R_h$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

two adjacent substituents of $R_a$, $R_b$, $R_c$, and $R_d$ are optionally joined to form a fused ring or form a multidentate ligand;

$R_e$ and $R_f$ or $R_g$ and $R_h$ are optionally joined to form a ring, which can optionally be substituted; and dotted arcs of ligand $L_{B28}$ and ligand $L_{B29}$ represent optional fused rings, which can be cyclic, heterocyclic, aromatic, or heteroaromatic, and which can be further substituted, wherein, when present, each end of each dotted arc is fused to a carbon atom of ring 3.

In some embodiments, each one of $X_7$, $X_8$, $X_9$, and $X_{10}$ is CH. In some embodiments, one, two, three, or four of $X_7$, $X_8$, $X_9$, and $X_{10}$ can be N.

In some embodiments, the ligand $L_B$ is selected from the group consisting of

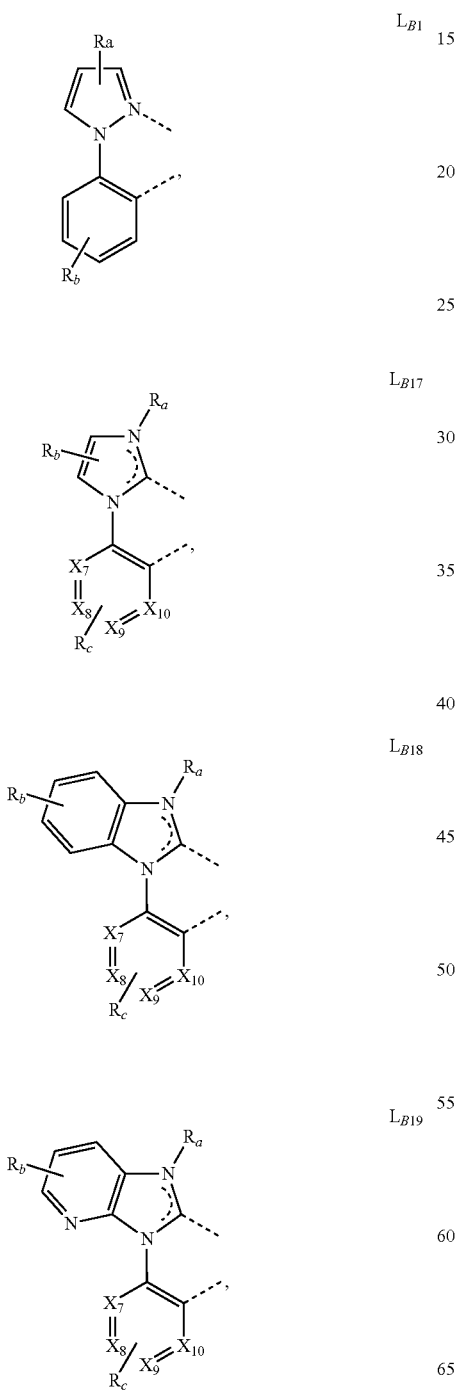

-continued

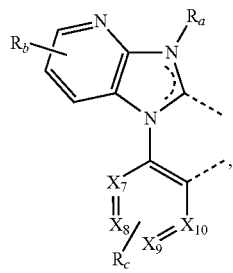

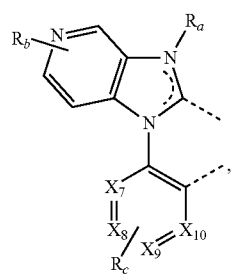

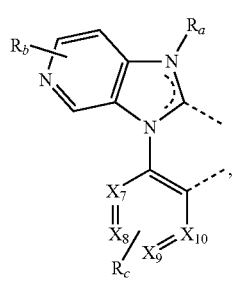

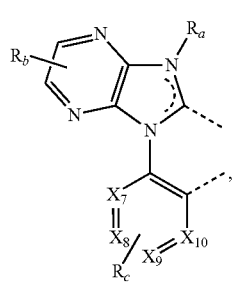

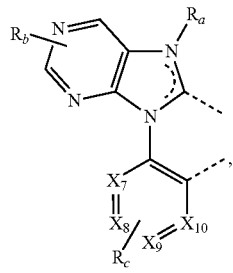

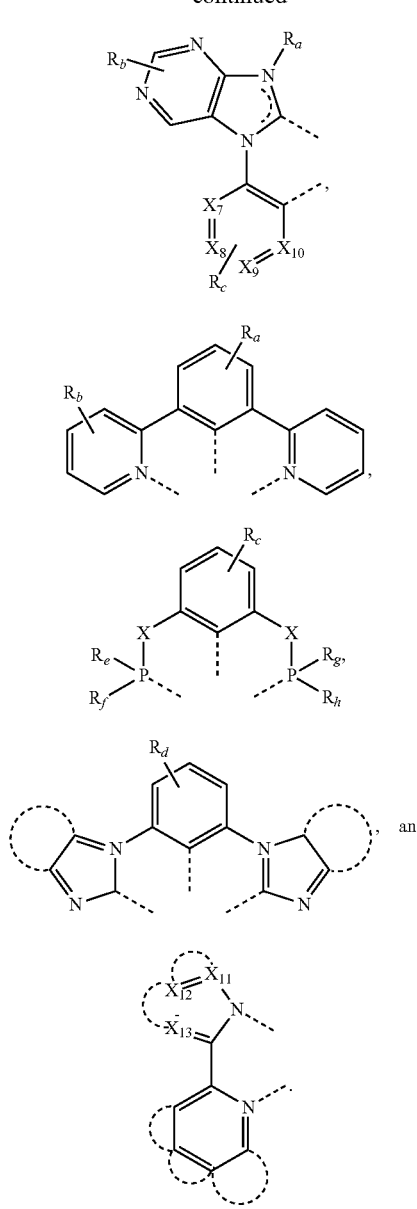

In some embodiments, the compound is homoleptic. In some embodiments, the compound is heteroleptic. In some embodiments, the compound has a facial (fac) configuration. In some embodiments, the compound has a meridional (mer) configuration.

In some embodiments, the compound is selected from the group consisting of:

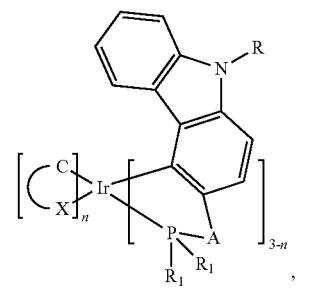

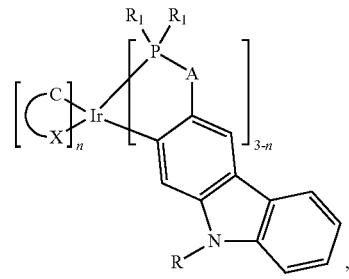

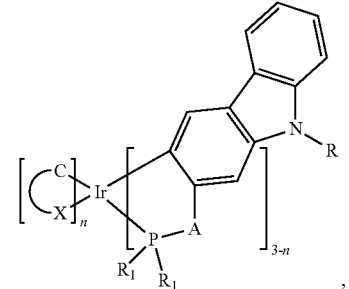

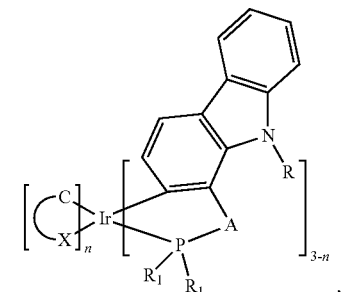

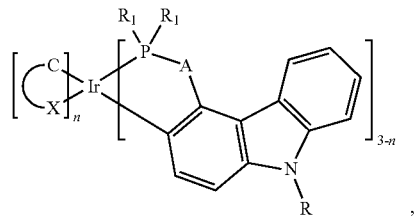

In some embodiments, $R_a$ and $R_b$ are H. In some embodiments, at least one $R_1$ is phenyl. In some embodiments, each $R_1$ is phenyl.

In some embodiments, the compound has the formula $M(L_A)_x(L_B)_y(L_C)_z$. In some embodiments, $L_A$, $L_B$ and $L_C$ are three different ligands; x is 1, or 2; y is 0, 1, or 2; z is 0, 1, or 2; and x+y+z is the oxidation state of the metal M. In some embodiments, z is 1, or 2. In some embodiments, z is 1, or 2, and the ligand $L_C$ is a monodentate ligand. In some embodiments, the ligand $L_C$ is selected from the group consisting of —PR'$_3$, —CO, and a halide (e.g., —F, —Cl, —Br, —I).

Each of the three R's in —PR'$_3$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

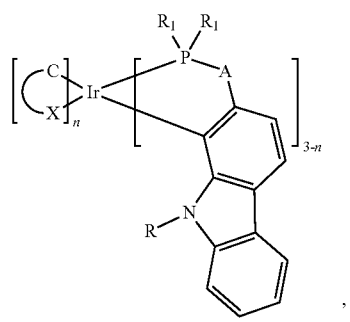

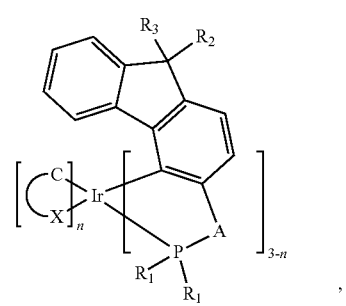

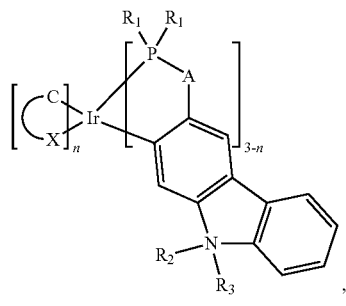

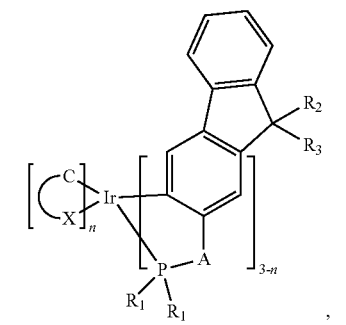

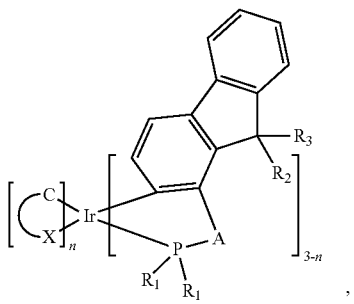

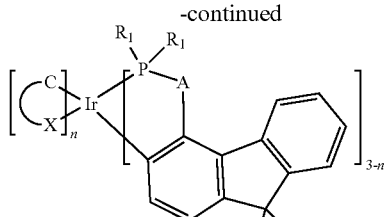

, and

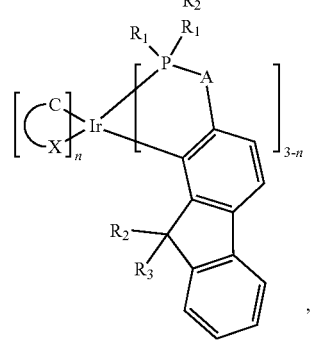

where

is selected from the group consisting of $L_{B1}$ through $L_{B28}$. In some embodiments,

is selected from the group consisting of $L_{B1}$, and $L_{B17}$-$L_{B25}$, and where n is 0, 1, or 2.

According to another aspect of the present disclosure, a first device is also provided. The first device includes a first organic light emitting device, that includes an anode, a cathode, and an organic layer disposed between the anode and the cathode. The organic layer may include a host and a phosphorescent dopant. The organic layer can include a compound that includes the ligand $L_A$, and its variations as described herein. The organic layer can be an emissive layer.

The first device can be one or more of a consumer product, an organic light-emitting device and a lighting panel. The organic layer can be an emissive layer and the compound can be an emissive dopant in some embodiments, while the compound can be a non-emissive dopant in other embodiments.

The organic layer can also include a host. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1$-$Ar_2$, $C_nH_{2n}$—$Ar_1$, or no substitution. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof.

The host can be a compound selected from the group consisting of carbazole, dibenzothiphene, dibenzofuran, dibenzoselenophene, azacarbazole, aza-dibenzothiophene, aza-dibenzofuran, and aza-dibenzoselenophene. The host can include a metal complex. The host can be a specific compound selected from the group consisting of:

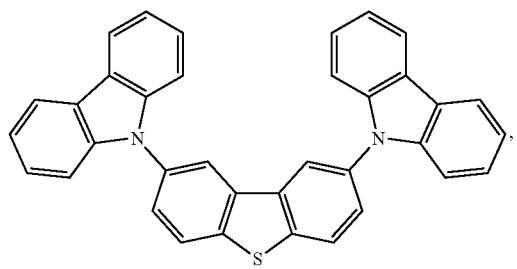

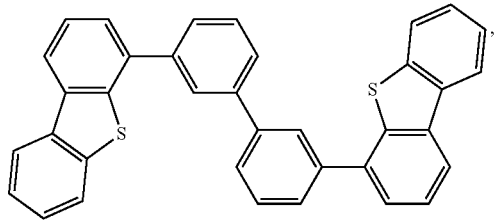

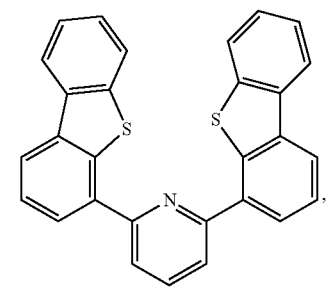

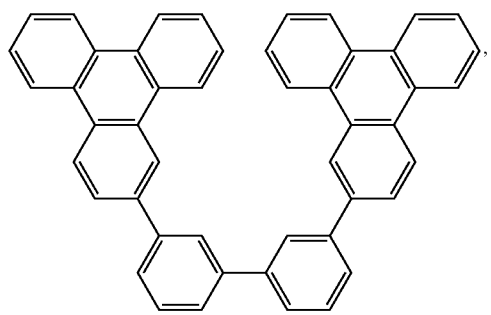

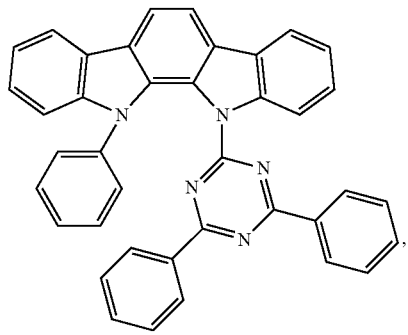

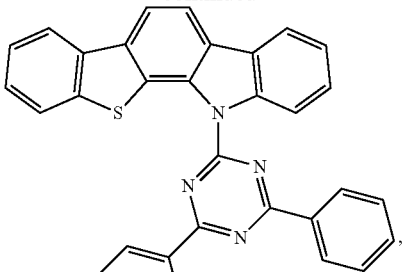

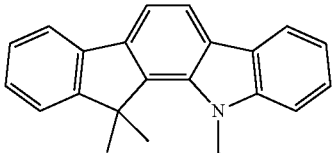

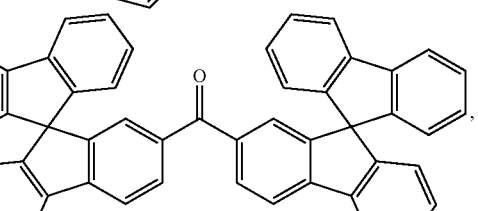

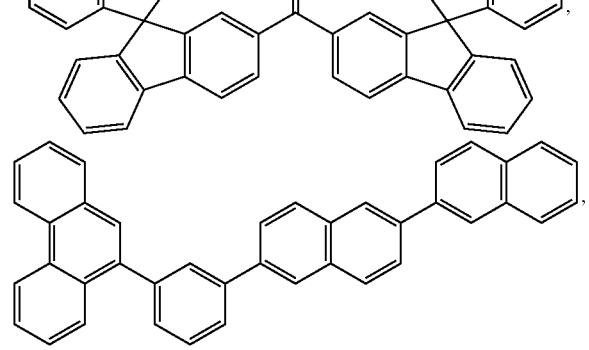

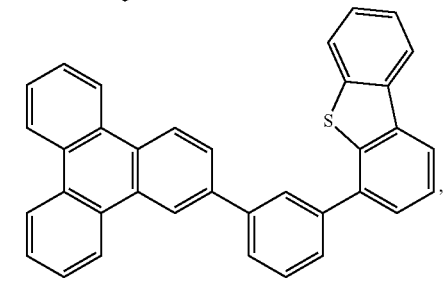

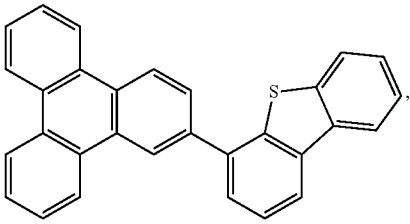 [SMILES: c1ccc2c(c1)sc1c(-c3ccc4c5ccccc5c5ccccc5c4c3)cccc12]

and combinations thereof.

In yet another aspect of the present disclosure, a formulation that comprises a a compound that comprises the ligand $L_A$, and int variations described herein, is described.

The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

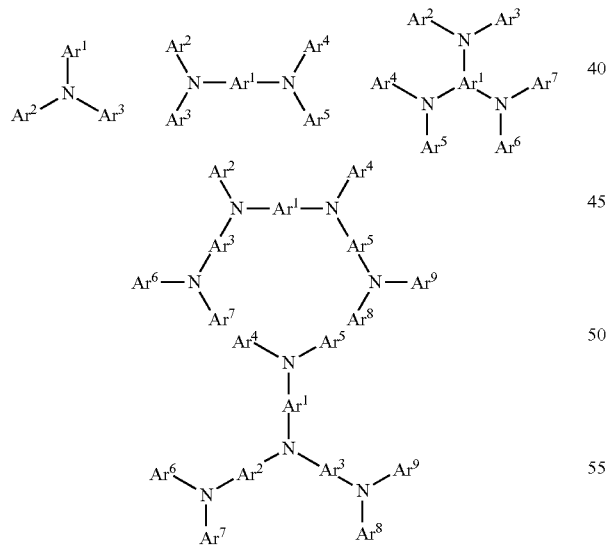

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

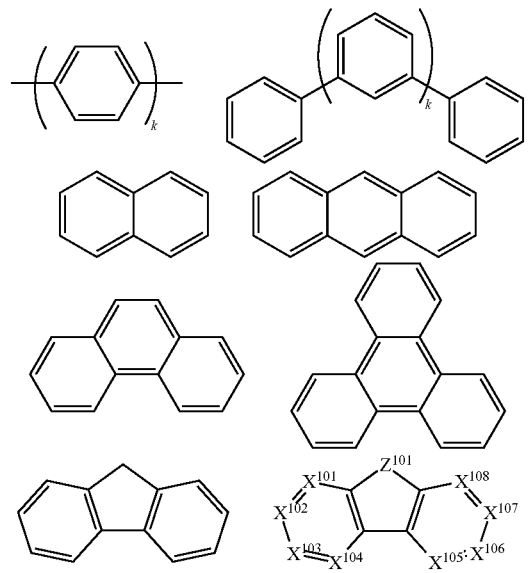

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

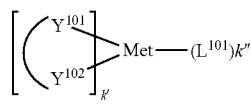

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. Fc+/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

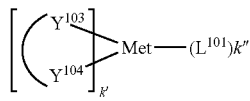

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

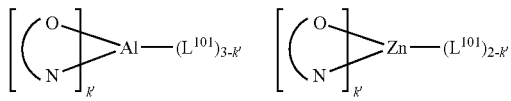

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

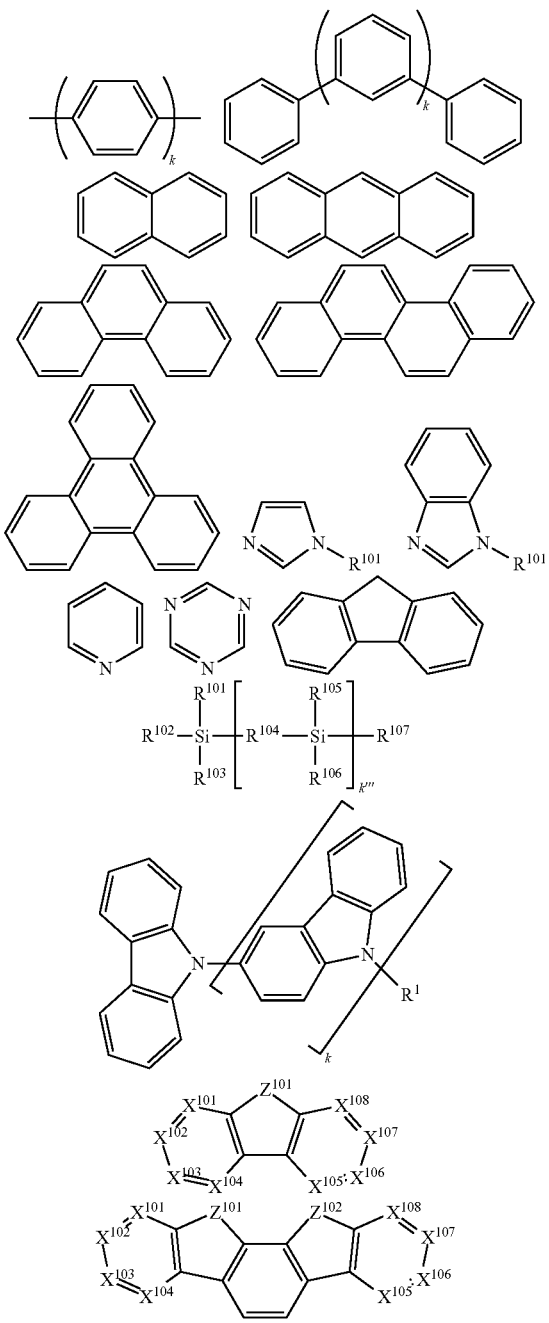

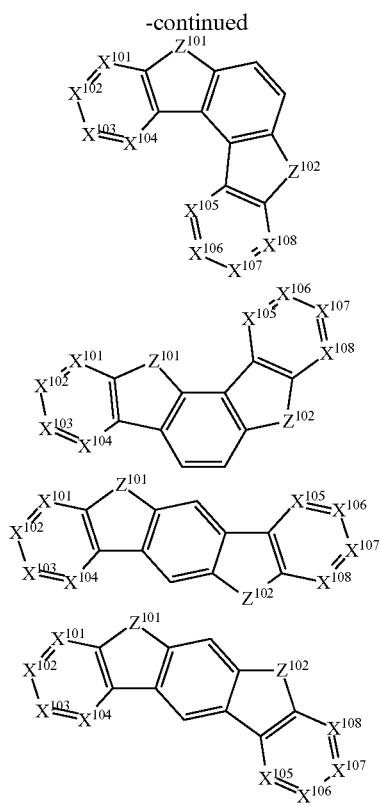

wherein $R_{101}$ to $R_{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR_{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

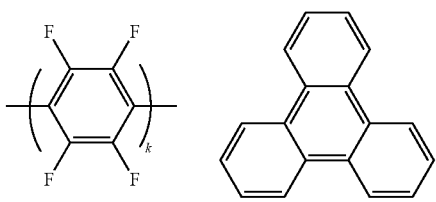

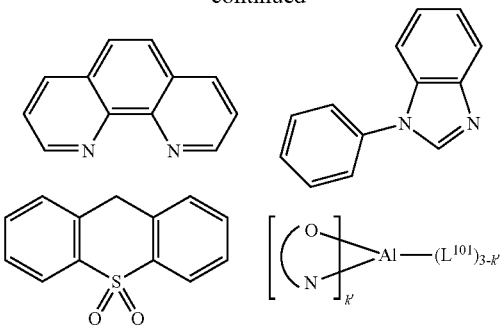

wherein k is an integer from 1 to 20; $L^{101}$ is an another ligand, k' is an integer from 1 to 3.

ETL:

Electron transport layer (ETL) may include a material capable of transporting electrons.

Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

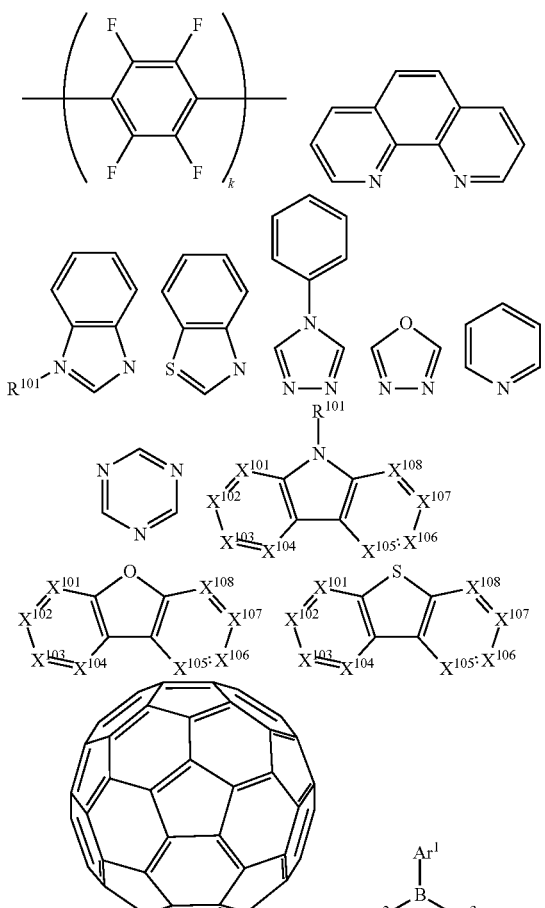

wherein $R_{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

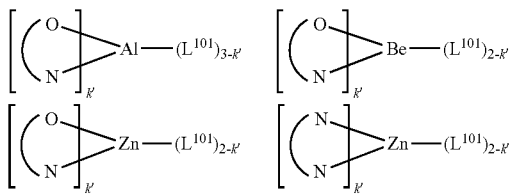

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A

| MATERIAL | EXAMPLES OF MATERIAL | PUBLICATIONS |
|---|---|---|
| Hole injection materials | | |
| Phthalocyanine and porphryin compounds | 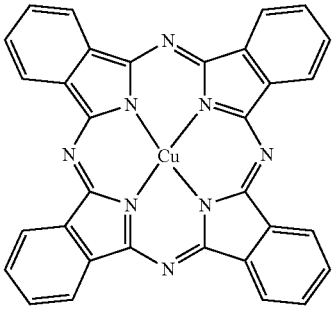 | Appl. Phys. Lett. 69, 2160 (1996) |
| Starburst triarylamines | 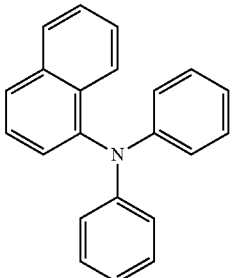 | J. Lumin. 72-74, 985 (1997) |
| $CF_x$ Fluorohydrocarbon polymer | 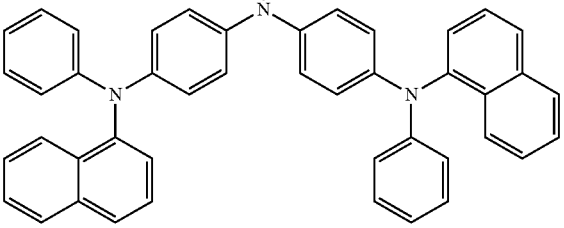 | Appl. Phys, Lett. 78, 673 (2001) |

TABLE A-continued
| MATERIAL | EXAMPLES OF MATERIAL | PUBLICATIONS |
| --- | --- | --- |
| Conducting polymers (e.g., PEDOT:PSS, polyaniline, polythiophene) | 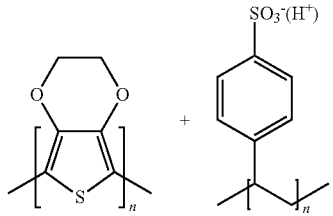 | Synth. Met. 87, 171 (1997)<br>WO2007002683 |
| Phosphonic acid and silane SAMs | 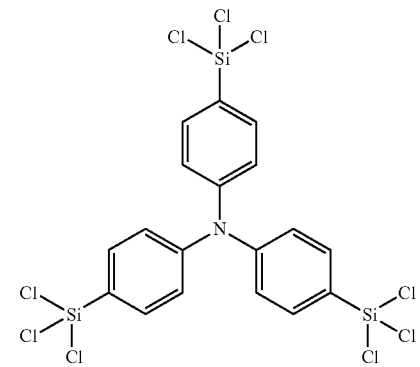 [SMILES: Cl[Si](Cl)(Cl)c1ccc(N(c2ccc([Si](Cl)(Cl)Cl)cc2)c2ccc([Si](Cl)(Cl)Cl)cc2)cc1] | US20030162053 |
| Triarylamine or polythiophene polymers with conductivity dopants | 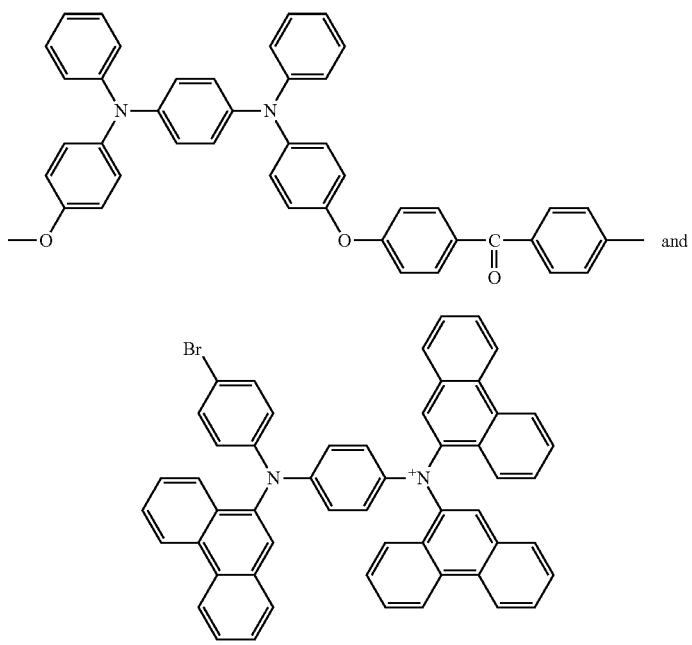 | EP1725079A1 |

TABLE A-continued
| MATERIAL | EXAMPLES OF MATERIAL | PUBLICATIONS |
|---|---|---|
| | 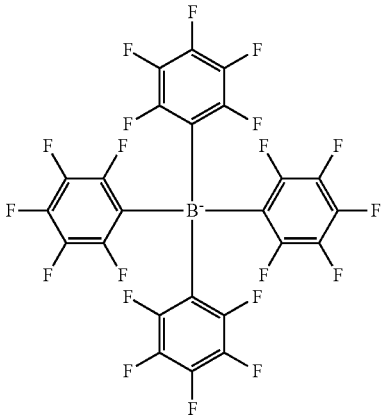 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Organic compounds with conductive inorganic compounds, such as molybdenum and tungsten oxides | 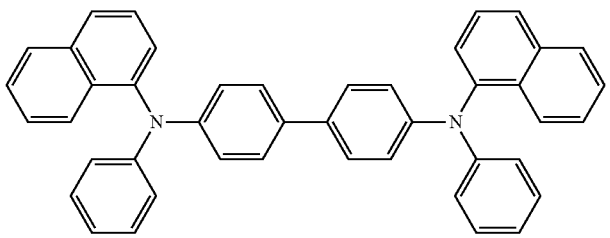 + $MoO_x$ | US20050123751<br>SID Symposium Digest, 37, 923 (2006)<br>WO2009018009 |
| n-type semiconducting organic complexes | 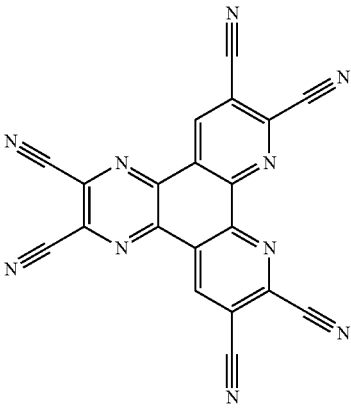 [SMILES: N#Cc1cc2c(nc1C#N)c1nc(C#N)c(C#N)cc1c1nc(C#N)c(C#N)nc21] | US20020158242 |
| Metal organometallic complexes | 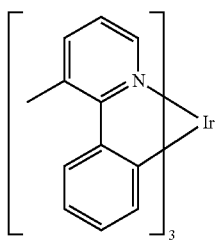 | US20060240279 |

TABLE A-continued

| MATERIAL | EXAMPLES OF MATERIAL | PUBLICATIONS |
| --- | --- | --- |
| Cross-linkable compounds | | US20080220265 |
| Polythiophene based polymers and copolymers | | WO 2011075644<br>EP2350216 |
| Hole transporting materials | | |
| Triarylamines<br>(e.g., TPD, α-NPD) | | Appl. Phys. Lett. 51, 913 (1987) |
| | | US5061569 |

TABLE A-continued
| MATERIAL | EXAMPLES OF MATERIAL | PUBLICATIONS |
|---|---|---|
| | 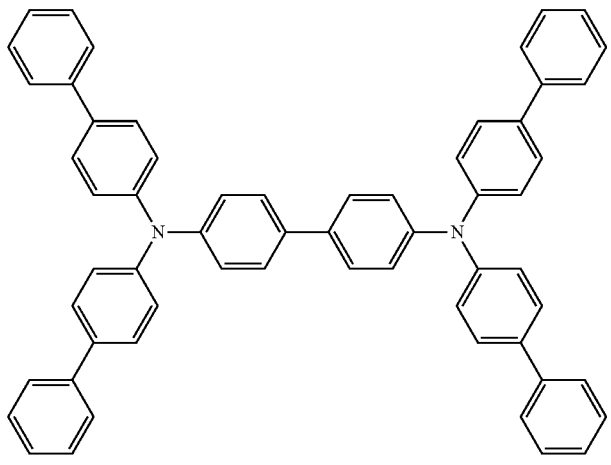 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 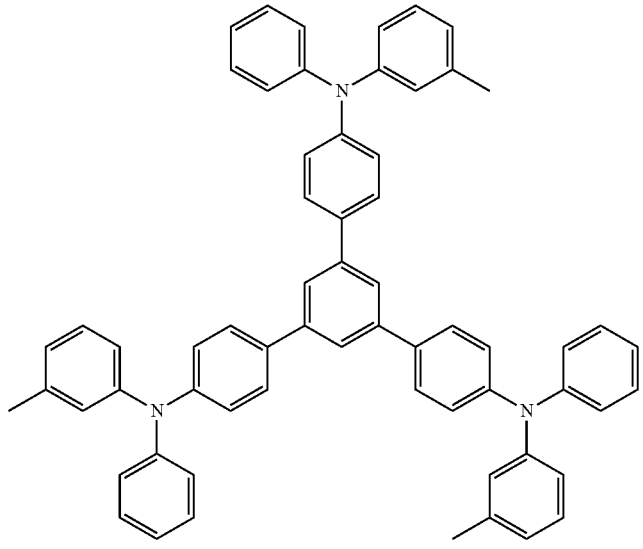 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 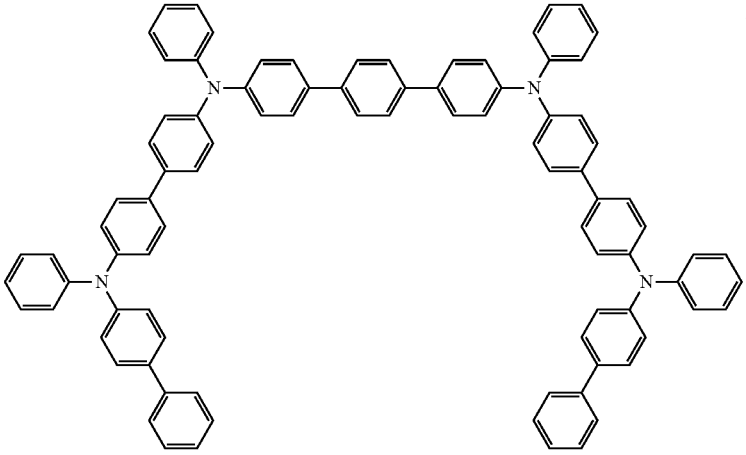 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE A-continued

| MATERIAL | EXAMPLES OF MATERIAL | PUBLICATIONS |
|---|---|---|
| | | Appl. Phys. Lett. 90, 183503 (2007) |
| Triarylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/ (di)benzofuran | | US20070278938, US20080106190 US20110163302 |

TABLE A-continued

| MATERIAL | EXAMPLES OF MATERIAL | PUBLICATIONS |
| --- | --- | --- |
| Indolocarbazoles | | Synth. Met. 111, 421 (2000) |
| Isoindole compounds | | Chem. Mater. 15, 3148 (2003) |
| Metal carbene complexes | | US20080018221 |

Phosphorescent OLED host materials
Red hosts

| | | |
| --- | --- | --- |
| Arylcarbazoles | | Appl. Phys. Lett. 78, 1622 (2001) |

TABLE A-continued

| MATERIAL | EXAMPLES OF MATERIAL | PUBLICATIONS |
| --- | --- | --- |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1,15 (2000) |
| Aromatic fused rings | | WO2009066779, WO2009066778, WO2009063833, US20090045731, US20090045730, WO2009008311, US20090008605, U320090009065 |

TABLE A-continued
| MATERIAL | EXAMPLES OF MATERIAL | PUBLICATIONS |
|---|---|---|
| Zinc complexes | 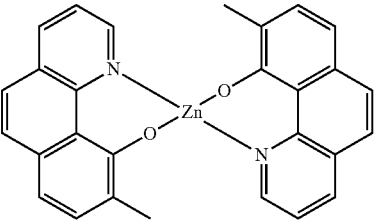 | WO2010056066 |
| Chrysene based compounds | 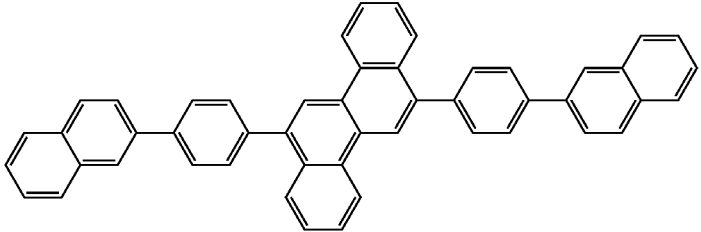 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
Green hosts
| | | |
|---|---|---|
| Arylcarbazoles | 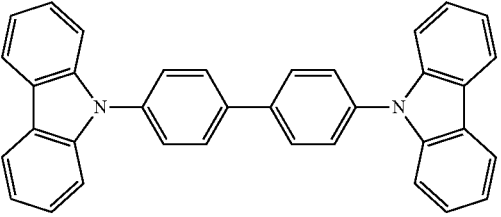 [SMILES: c1ccc2c(c1)c1ccccc1n2-c1ccc(-c2ccc(-n3c4ccccc4c4ccccc43)cc2)cc1] | Appl. Phys, Lett. 78, 1622 (2001) |
| | 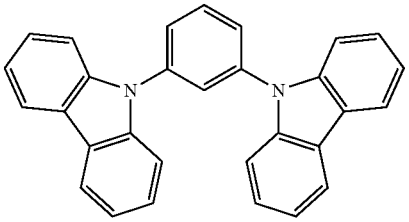 [SMILES: c1cc(-n2c3ccccc3c3ccccc32)cc(-n2c3ccccc3c3ccccc32)c1] | US20030175553 |
| | 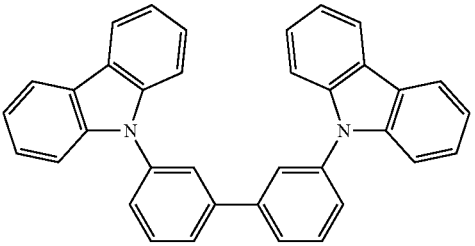 [SMILES: c1cc(-c2cccc(-n3c4ccccc4c4ccccc43)c2)cc(-n2c3ccccc3c3ccccc32)c1] | WO2001039234 |
| Aryltriphenylene compounds | 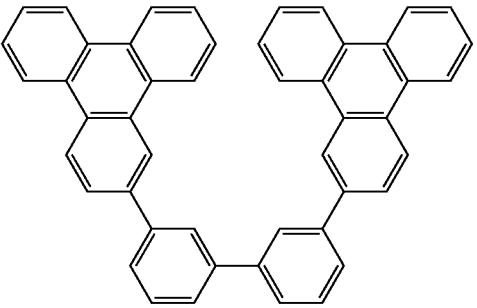 [SMILES: c1cc(-c2cccc(-c3ccc4c5ccccc5c5ccccc5c4c3)c2)cc(-c2ccc3c4ccccc4c4ccccc4c3c2)c1] | US20060280965 |

TABLE A-continued
| MATERIAL | EXAMPLES OF MATERIAL | PUBLICATIONS |
|---|---|---|
| | 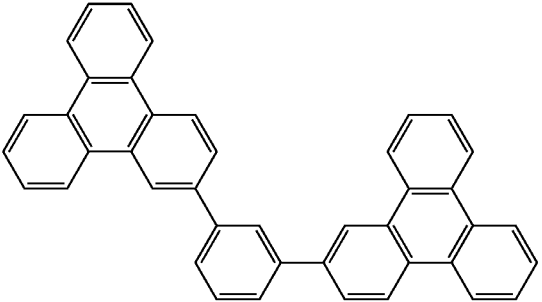 [SMILES: c1cc(-c2ccc3c4ccccc4c4ccccc4c3c2)cc(-c2ccc3c4ccccc4c4ccccc4c3c2)c1] | US20060280965 |
| | 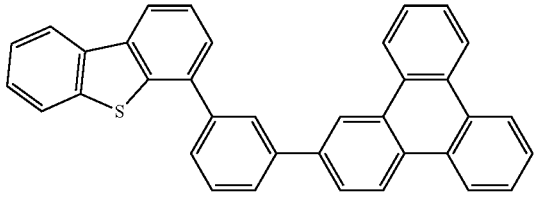 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 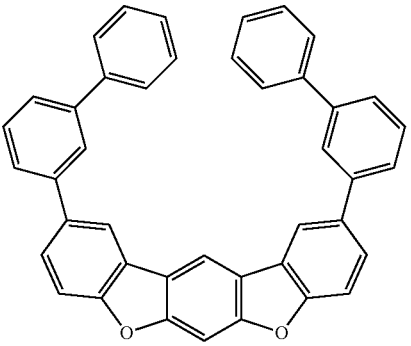 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 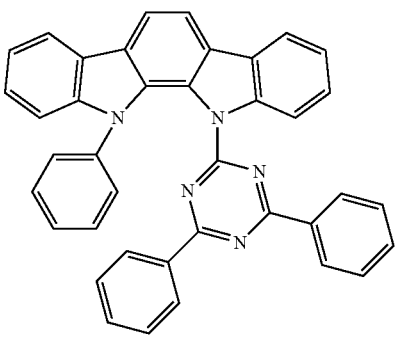 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 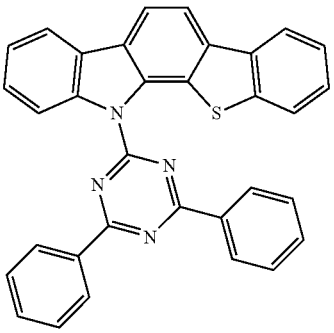 [SMILES: c1ccc(-c2nc(-c3ccccc3)nc(-n3c4ccccc4c4ccc5c6ccccc6sc5c43)n2)cc1] | WO2010107244 |

TABLE A-continued
| MATERIAL | EXAMPLES OF MATERIAL | PUBLICATIONS |
|---|---|---|
| Aza-carbazole/DBT/DBF | 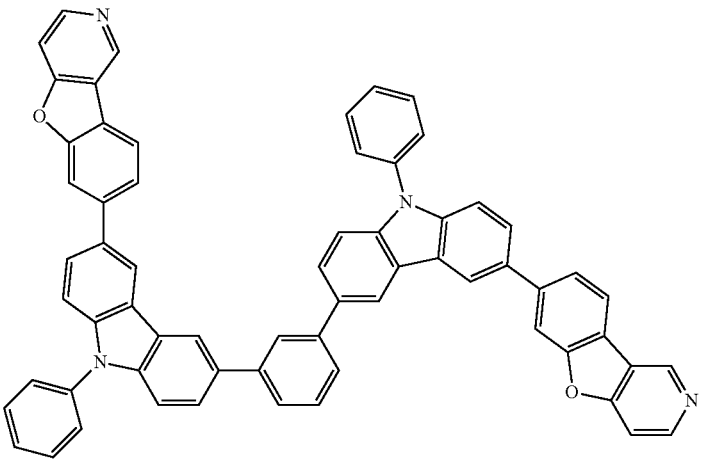 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 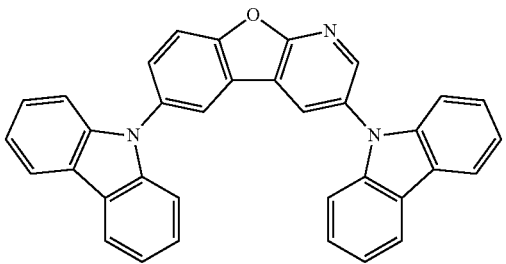 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 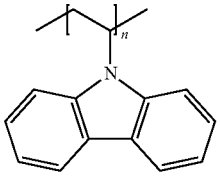 | Appl. Phys. Lett. 77, 2280 (2000) |
| Spirofluorene compounds | 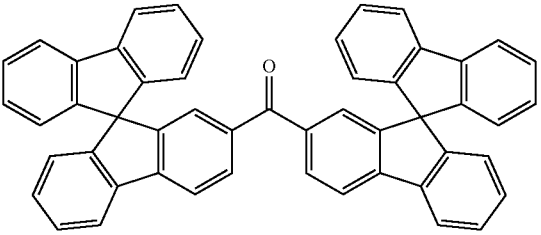 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 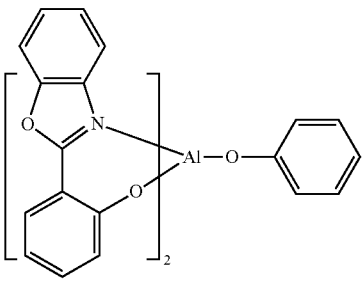 | WO2005089025 |

| MATERIAL | EXAMPLES OF MATERIAL | PUBLICATIONS |
|---|---|---|
| | | WO2006132173 |
| | | JP200511610 |
| Spirofluorene-carbazole compounds | | JP2007254297 |
| | | JP2007254297 |
| Indolocarbazoles | | WO2007063796 |

TABLE A-continued

| MATERIAL | EXAMPLES OF MATERIAL | PUBLICATIONS |
| --- | --- | --- |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |
| Metal phenoxypyridine compounds | | WO2005030900 |

TABLE A-continued

| MATERIAL | EXAMPLES OF MATERIAL | PUBLICATIONS |
| --- | --- | --- |
| Metal coordination complexes (e.g., Zn, Al with N^N ligands) | | US20040137268. US20040137267 |
| Blue hosts | | |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |
| | | WO2009086028 |

TABLE A-continued

| MATERIAL | EXAMPLES OF MATERIAL | PUBLICATIONS |
|---|---|---|
| | | US20090030202, US20090017330 |
| | | US20100084966 |
| Silicon aryl compounds | | US20050238919 |
| | | WO2009003898 |
| Silicon/Germanium aryl compounds | | EP2034538A |
| Aryl benzoyl ester | | WO2006100298 |

TABLE A-continued
| MATERIAL | EXAMPLES OF MATERIAL | PUBLICATIONS |
| --- | --- | --- |
| Carbazole linked by non-conjugated groups | 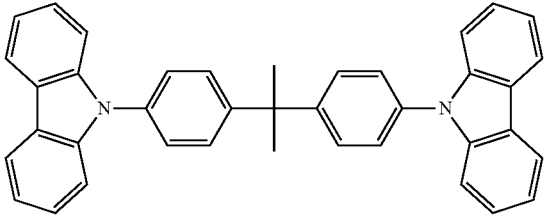 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 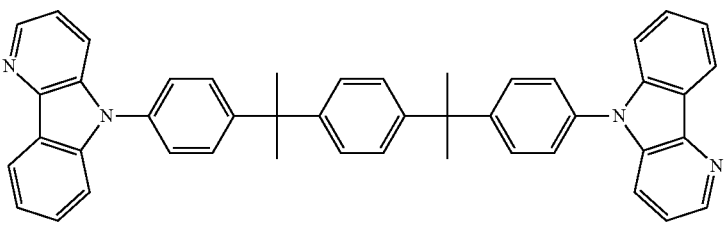 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| High triplet metal organometallic complex | 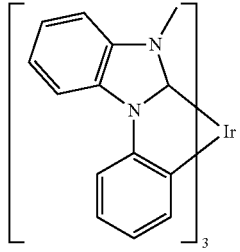 | US7154114 |
| Phosphorescent dopants | | |
| Red dopants | | |
| Heavy metal porphyrins (e.g., PtOEP) | 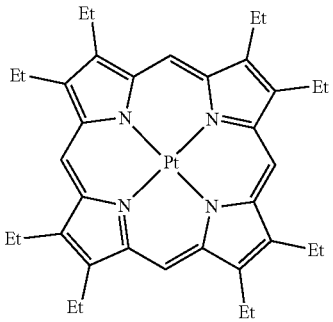 | Nature 395, 151 (1998) |
| Iridium(III) organometallic complexes | 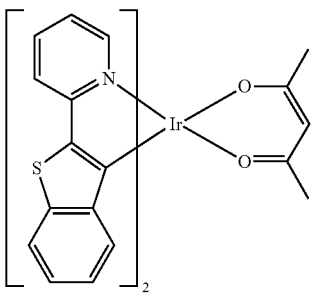 | Appl. Phys. Lett. 78, 1622 (2001) |

TABLE A-continued

| MATERIAL | EXAMPLES OF MATERIAL | PUBLICATIONS |
|---|---|---|
| | | US20030072964 |
| | | US20030072964 |
| | | US20060202194 |
| | | US20060202194 |
| | | US20070087321 |

TABLE A-continued

| MATERIAL | EXAMPLES OF MATERIAL | PUBLICATIONS |
|---|---|---|
| | | US20080261076<br>US20100090591 |
| | | US20070087321 |
| | | Adv. Mater. 19, 739 (2007) |
| | | WO2009100991 |
| | | WO2008101842 |

TABLE A-continued
| MATERIAL | EXAMPLES OF MATERIAL | PUBLICATIONS |
|---|---|---|
| | 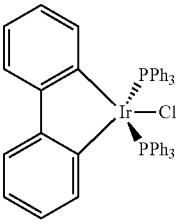 | US7232618 |
| Platinum(II) organometallic complexes | 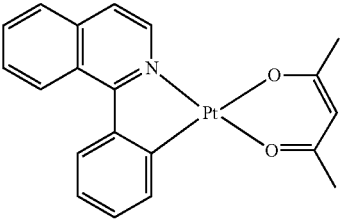 | WO2003040257 |
| | 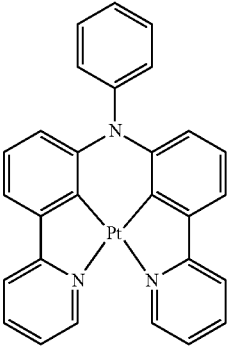 | US20070103060 |
| Osminum(III) complexes | 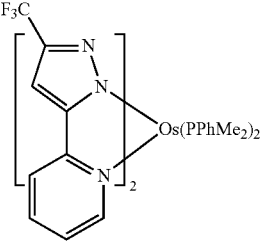 | Chem. Mater. 17, 3532 (2005) |
| Ruthenium(II) complexes | 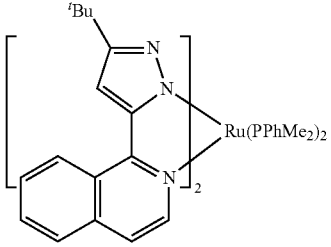 | Adv. Mater. 17, 1059 (2005) |
| Rhenium (I), (II), and (III) complexes | 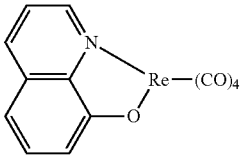 | US20050244673 |

TABLE A-continued
| MATERIAL | EXAMPLES OF MATERIAL | PUBLICATIONS |
|---|---|---|
| | Green dopants | |
| Iridium(III) organometallic complexes | 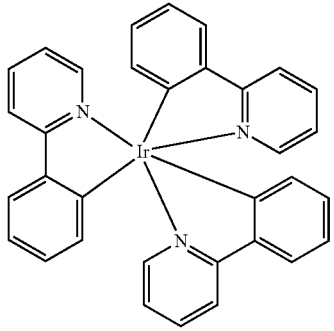<br>and its derivatives | Inorg. Chem. 40, 1704 (2001) |
| | 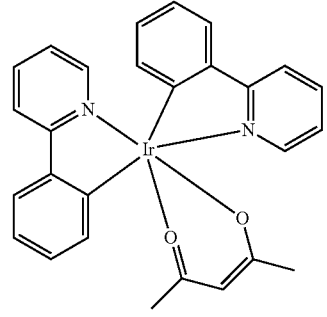 | US20020034656 |
| | 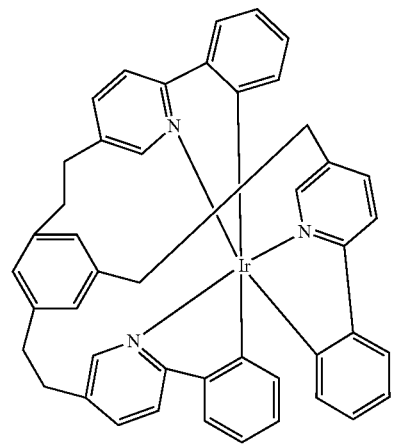 | US7332232 |
| | 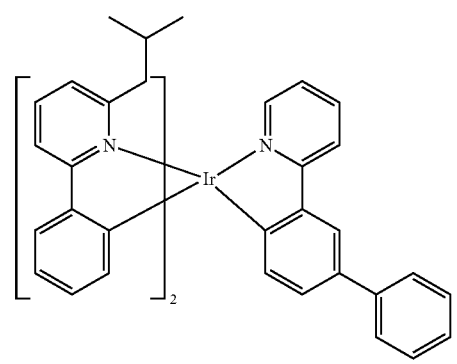 | US20090108737 |

TABLE A-continued

| MATERIAL | EXAMPLES OF MATERIAL | PUBLICATIONS |
| --- | --- | --- |
| | | WO2010028151 |
| | | EP1841834B |
| | | US20060127696 |
| | | US20090039776 |
| | | US6921915 |

TABLE A-continued

| MATERIAL | EXAMPLES OF MATERIAL | PUBLICATIONS |
|---|---|---|
| | | US20100244004 |
| | | US6687266 |
| | | Chem. Mater. 16, 2480 (2004) |
| | | US20070190359 |
| | | US 20060008670<br>JP2007123392 |

TABLE A-continued

| MATERIAL | EXAMPLES OF MATERIAL | PUBLICATIONS |
|---|---|---|
| | | WO2010086089, WO2011044988 |
| | | Adv. Mater. 16, 2003 (2004) |
| | | Angew. Chem. Int. Ed. 2006, 45, 7800 |
| | | WO2009050290 |
| | | US20090165846 |
| | | US20080015355 |

TABLE A-continued

| MATERIAL | EXAMPLES OF MATERIAL | PUBLICATIONS |
|---|---|---|
| | [Ir(bpy)₃](PF₆)₃ complex structure | US20010015432 |
| | Ir complex with bis(pyridyl)borate ligand | US20100295032 |
| Monomer for polymeric metal organometallic compounds | Ir complex with phenylpyridine and acetylacetonate with vinylphenyl substituent | US7250226, US7396598 |
| Pt(II) organometallic complexes, including polydentated ligands | N^C^N-Pt-Cl complex with bis(pyridyl)phenyl ligand | Appl, Phys. Lett. 86, 153505 (2005) |
| | N^C^N-Pt-O-phenyl complex with bis(pyridyl)phenyl ligand | Appl. Phys. Lett. 86, 153505 (2005) |

TABLE A-continued

| MATERIAL | EXAMPLES OF MATERIAL | PUBLICATIONS |
|---|---|---|
| | | Chem. Lett. 34, 592 (2005) |
| | | WO2002015645 |
| | | US20060263635 |
| | | US20060182992<br>US20070103060 |

TABLE A-continued
| MATERIAL | EXAMPLES OF MATERIAL | PUBLICATIONS |
|---|---|---|
| Cu complexes | 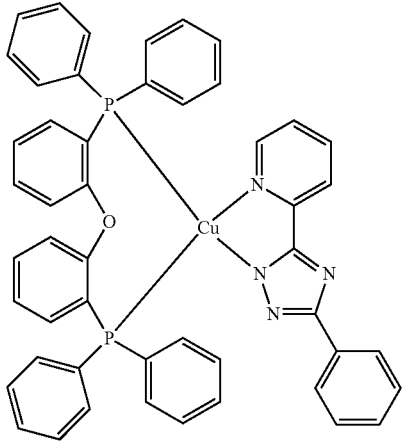 | WO2009000673 |
| | 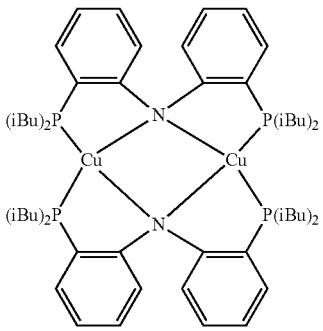 | US20070111026 |
| Gold complexes | 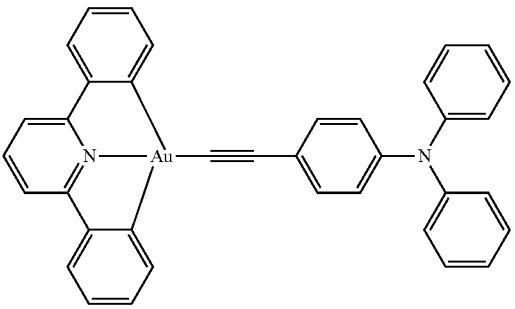 | Chem. Commun. 2906 (2005) |
| Rhenium (III) complexes | 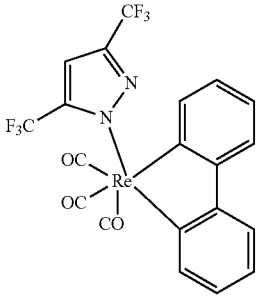 | Inorg. Chem. 42, 1248 (2003) |

TABLE A-continued

| MATERIAL | EXAMPLES OF MATERIAL | PUBLICATIONS |
| --- | --- | --- |
| Osmium(II) complexes | | US7279704 |
| Deuterated organometallic complexes | | US20030138657 |
| Organometallic complexes with two or more metal centers | | US20030152802 |
| | | US7090928 |

TABLE A-continued
| MATERIAL | EXAMPLES OF MATERIAL | PUBLICATIONS |
|---|---|---|
| Blue dopants | | |
| Iridium(III) organometallic complexes | 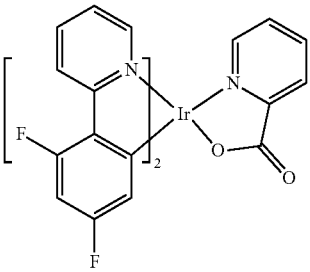 | WO2002002714 |
| | 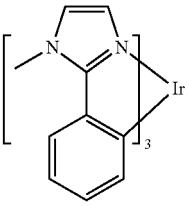 | WO2006009024 |
| | 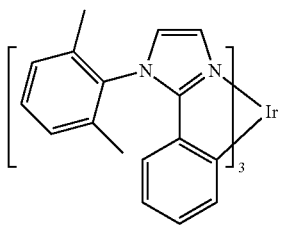 | US20060251923<br>US20110057559<br>US20110204333 |
| | 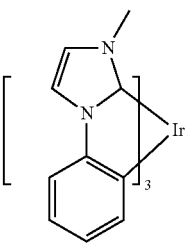 | US7393599,<br>WO2006056418,<br>US20050260441,<br>WO2005019373 |
| | 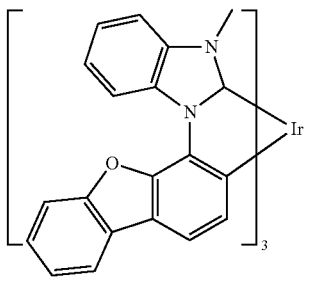 | US7534505 |

TABLE A-continued

| MATERIAL | EXAMPLES OF MATERIAL | PUBLICATIONS |
|---|---|---|
| | | WO2011051404 |
| | | US7445855 |
| | | US20070190359, US20080297033 US20100148663 |
| | | US7338722 |
| | | US20020134984 |

TABLE A-continued

| MATERIAL | EXAMPLES OF MATERIAL | PUBLICATIONS |
|---|---|---|
| | | Angew. Chem. Int. Ed. 47, 4542 (2008) |
| | | Chem. Mater. 18, 5119 (2006) |
| | | Inorg. Chem. 46, 4308 (2007) |
| | | WO2005123873 |
| | | WO2005123873 |

TABLE A-continued
| MATERIAL | EXAMPLES OF MATERIAL | PUBLICATIONS |
|---|---|---|
| | 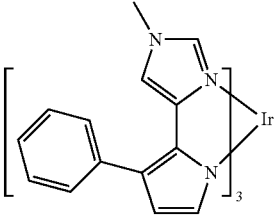 | WO2007004380 |
| | 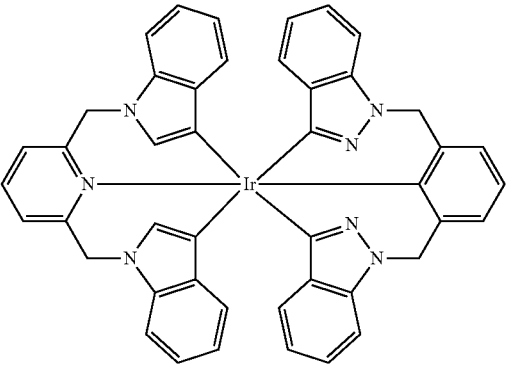 | WO2006082742 |
| Osmium(II) complexes | 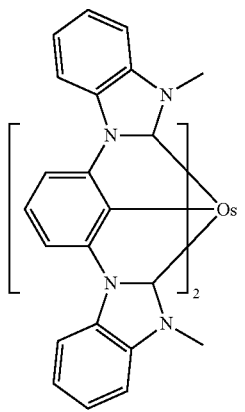 | US7279704 |
| | 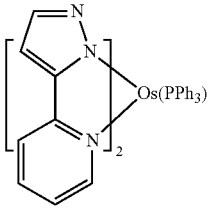 | Organometallics 23, 3745 (2004) |
| Gold complexes | 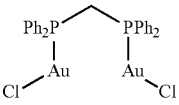 | Appl. Phys. Lett. 74, 1361 (1999) |
| Platinum(II) complexes | 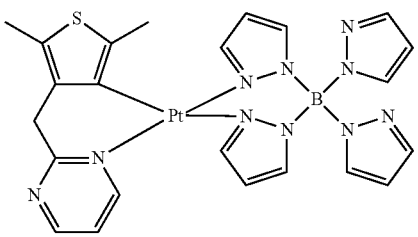 | WO2006098120, WO2006103874 |

TABLE A-continued

| MATERIAL | EXAMPLES OF MATERIAL | PUBLICATIONS |
|---|---|---|
| Pt tetradentate complexes with at least one metal-carbene bond | 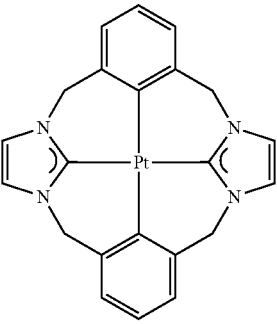 | US7655323 |
| | Exciton/hole blocking layer materials | |
| Bathocuprine compounds (e.g., BCP, BPhen) | 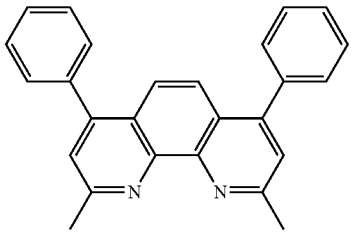 [SMILES: Cc1cc(-c2ccccc2)c2ccc3c(-c4ccccc4)cc(C)nc3c2n1] | Appl. Phys. Lett. 75, 4 (1999) |
| | 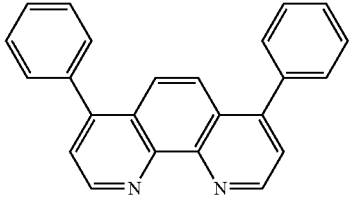 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 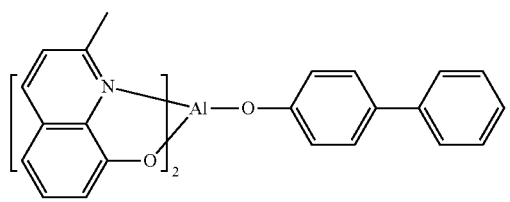 | Appl. Phys. Lett. 81, 162 (2002) |
| 5-member ring electron deficient heterocycles such as triazole, oxadiazole, imidazole, benzoimidazole | 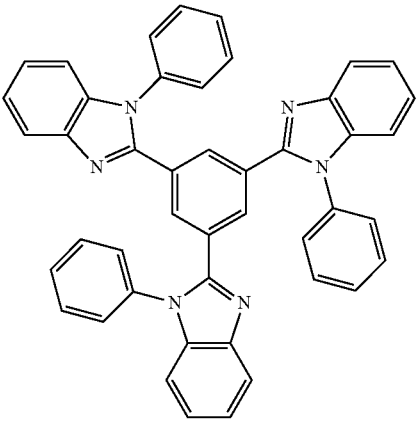 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE A-continued
| MATERIAL | EXAMPLES OF MATERIAL | PUBLICATIONS |
|---|---|---|
| Triphenylene compounds | 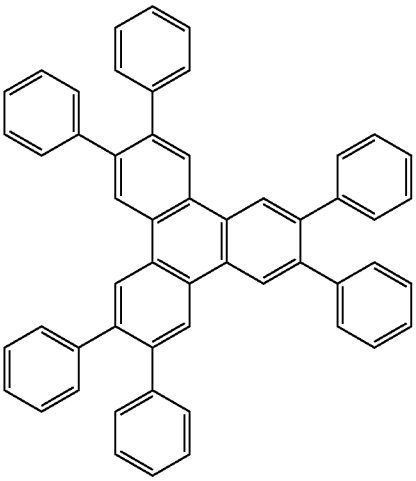 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 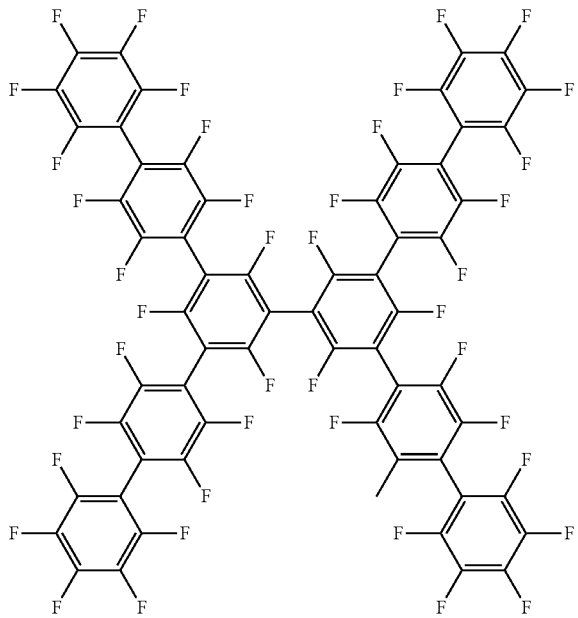 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 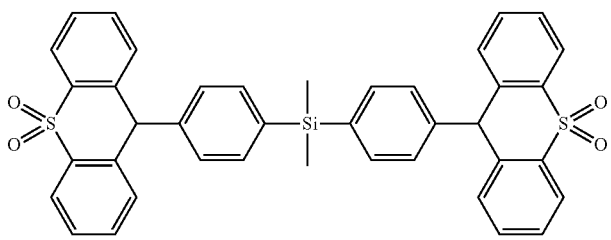 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 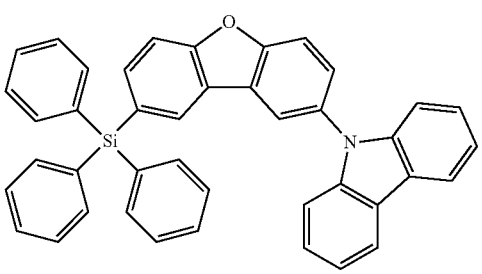 [SMILES: c1ccc([Si](c2ccccc2)(c2ccccc2)c2ccc3oc4ccc(-n5c6ccccc6c6ccccc65)cc4c3c2)cc1] | WO2010079051 |

TABLE A-continued
| MATERIAL | EXAMPLES OF MATERIAL | PUBLICATIONS |
|---|---|---|
| Aza-carbazoles | 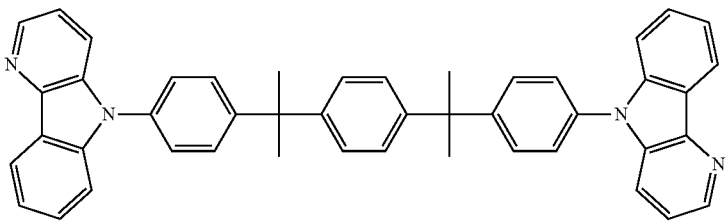 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 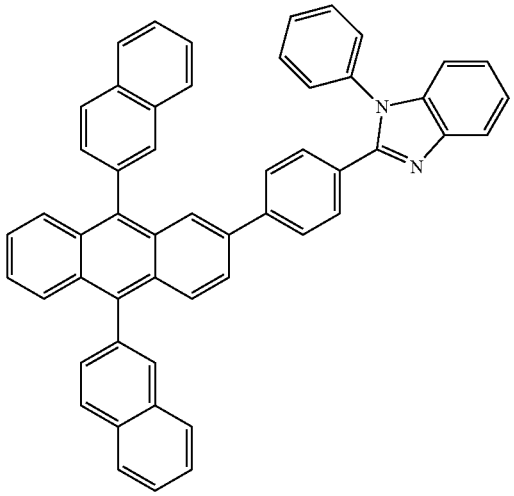 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 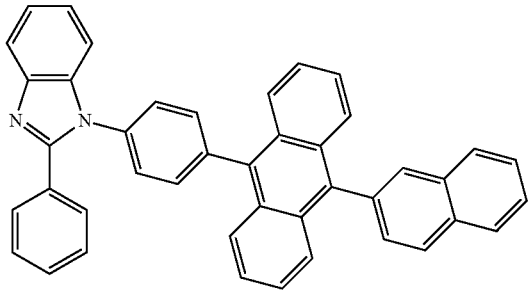 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 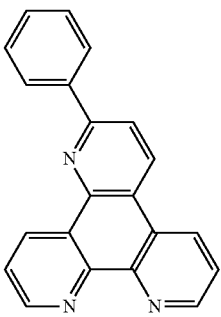 [SMILES: c1ccc(-c2ccc3c4cccnc4c4ncccc4c3n2)cc1] | US20090115316 |
| Anthracene-benzothiazole compounds | 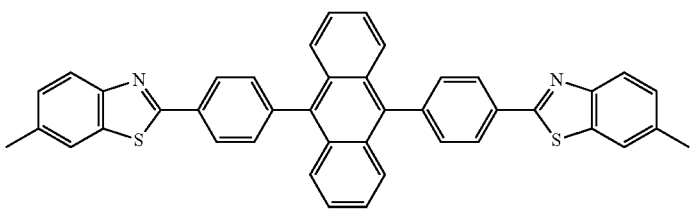 | Appl. Phys. Lett. 89, 063504 (2006) |

TABLE A-continued

| MATERIAL | EXAMPLES OF MATERIAL | PUBLICATIONS |
| --- | --- | --- |
| Metal 8-hydroxyquinolates (e.g., Alq$_3$, Zrq$_4$) | | Appl. Phys. Lett. 51, 913 (1987) US7230107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient Keterocycles (e.g., triazole, oxadiazole, imidazole, benzoimidazole) | | Appl. Phys. Lett. 74, 865 (1999) |
| | | Appl. Phys. Lett. 55, 1489 (1989) |

TABLE A-continued
| MATERIAL | EXAMPLES OF MATERIAL | PUBLICATIONS |
|---|---|---|
| | 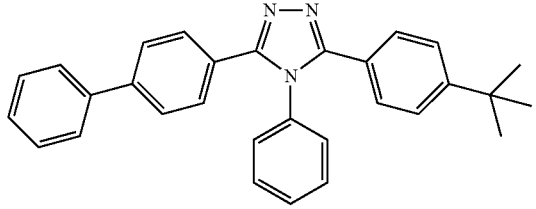 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 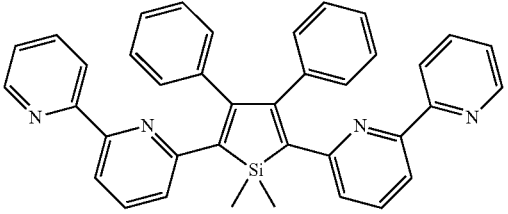 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 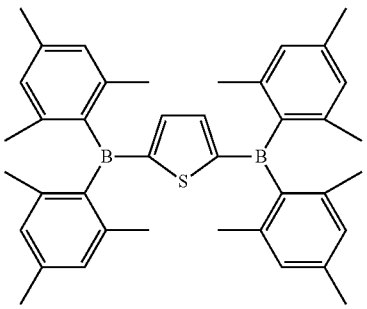 | J. Am. Chem. Soc. 120, 9714 (1998) |
| Fluorinated aromatic compounds | 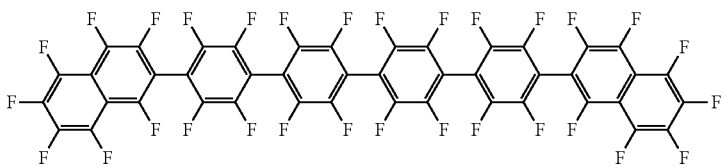 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 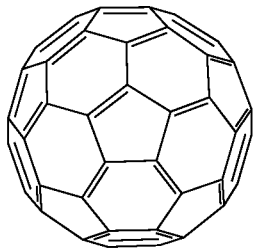 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 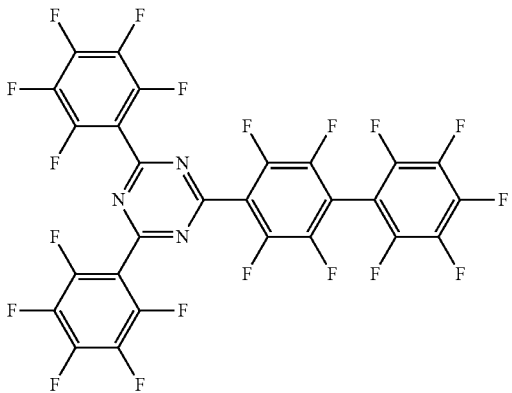 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

TABLE A-continued

| MATERIAL | EXAMPLES OF MATERIAL | PUBLICATIONS |
|---|---|---|
| Zn (N^N) complexes | [Chemical structure of Zn complex with quinoline and SO2-phenyl sulfonamide ligand, shown as [...]2] | US6528187 |

EXPERIMENTAL

Examples of a series of Ir(III) complexes containing phosphinoaryl (aryl=naphthalene, quinoline, and 5-isoquinoline) cyclometalates of (C^P) chelates are evaluated. The examples have two 2-phenylpyrazole (ppz) of (C^N) chelates and one C^P ligand, constructed as [(C^N)$_2$Ir(C^P)]. The complexes show a photo-isomerisation property that is normally detected for homoleptic Ir(III) complexes, and quantum yields that varied up to 50% at room temperature.

The lowest triplet spin density of all complexes is on the aryl part from the phosphinoaryl chelates, while the phosphorescence of all complexes are originated from the aryl group in the phosphinoaryl chelates.

The data shows that the design of heteroleptic Ir(III) complexes with phosphinoaryl ligand of varied lowest triplet energy can lead to RGB phosphors to fulfill the demand of full-color OLED display.

Figure 4:
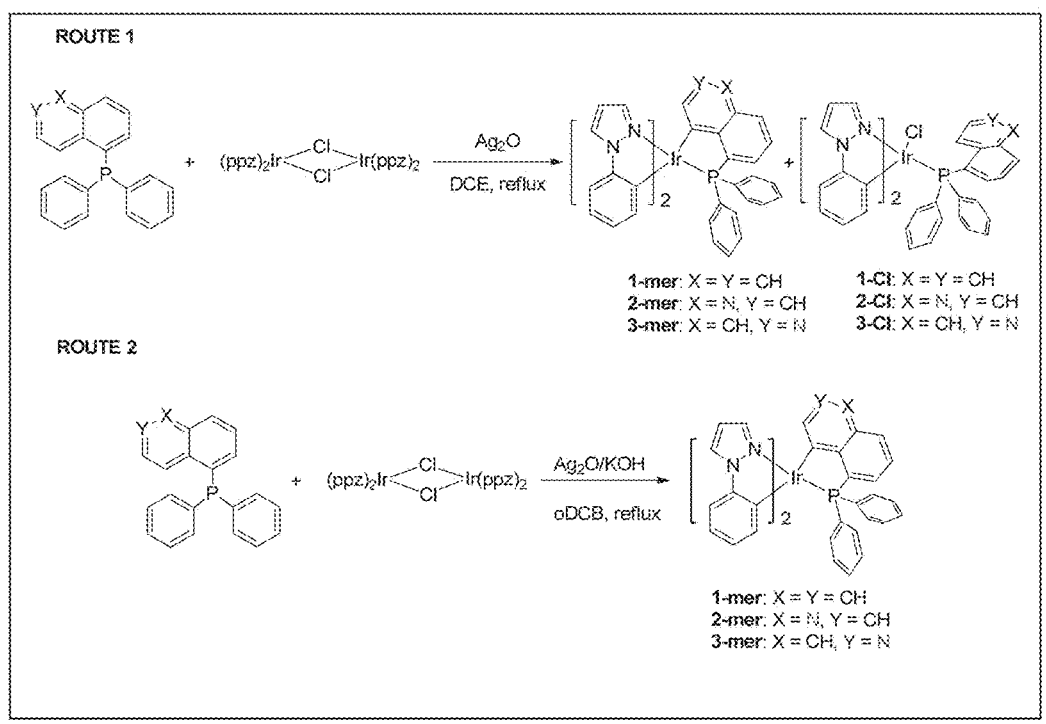
FIG. 4 shows examples of synthetic routes for producing Ir(III) complexes with C^P chelates.
Figure 5:
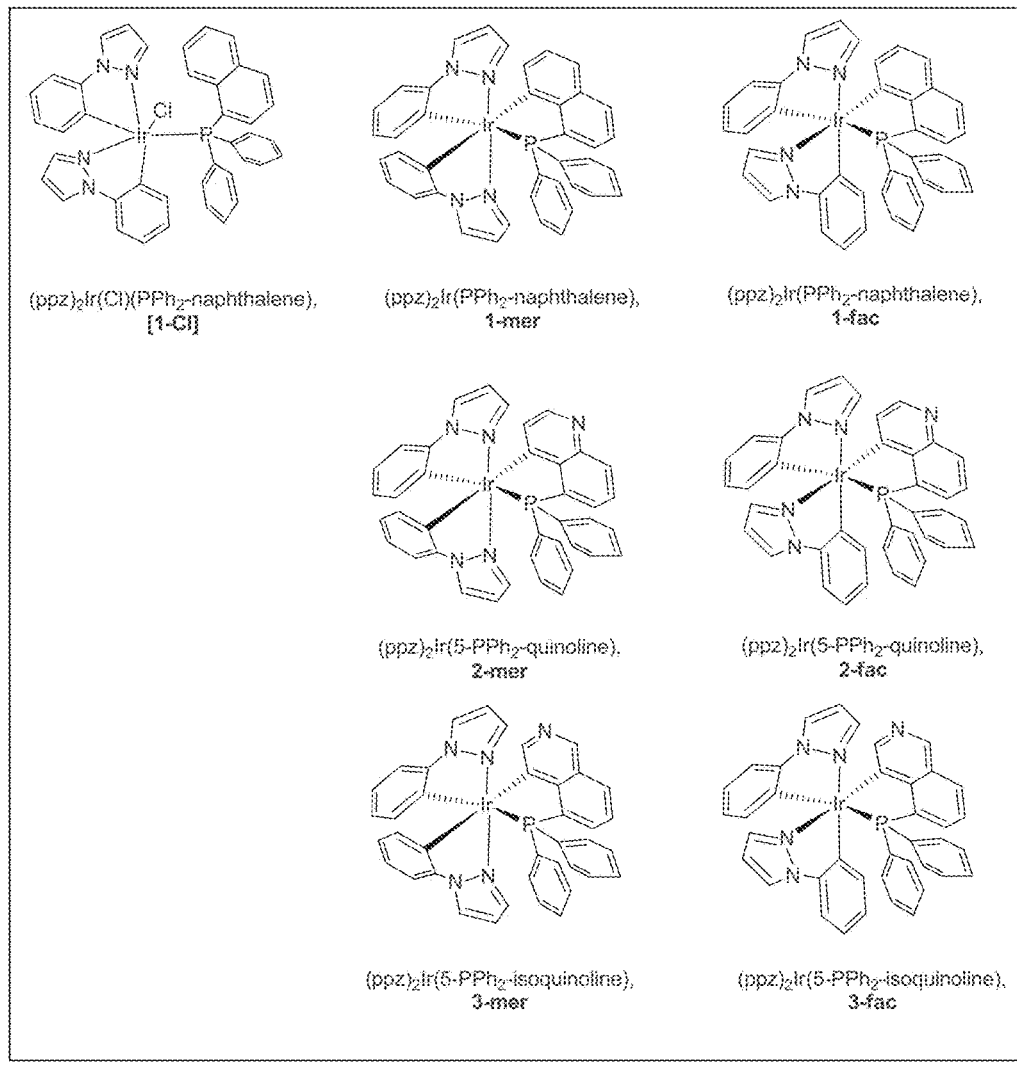
FIG. 5 shows various isomers of Ir(III) complexes complexes with C^P chelates.

Synthesis of (ppz)$_2$Ir(PPh$_2$-naphthalene) (1-mer), (ppz)$_2$Ir (5-PPh$_2$-quinoline) (2-mer), and (ppz)$_2$Ir(5-PPh$_2$-isoquinoline) (3-mer) can be achieved from two synthetic routes shown in FIG. 4. From Route 1, the synthesis started with reflux of a mixture of phosphinoaryl ligand, [(ppz)$_2$Ir(μ-Cl)]$_2$, and silver oxide for 18 h in 1,2-dichloroethane (DCE). The yield of the meridional isomer of complexes (n-mer) (n=1-3) was less than 10%. The major product obtained was the non-cyclometalated complex (n-Cl) (n=1-3) with a Ir—Cl bond remaining. Route 2 shows a newly developed synthetic method for producing meridional complexes 1-3. The reaction of Route 2 was performed with the mixture of phosphinoaryl ligand, silver oxide, KOH, and [(ppz)$_2$Ir(μ-Cl)]$_2$ refluxed in 1,2-dichlorobenzene (oDCB) for 18 h. No formation of the n-Cl (n=1-3) complex was observed. This synthetic route leaded to the formation of only meridional complexes 1-3 with a yield over 70%. The various complexes (n=1-3) are shown in FIG. 5.

Figure 7:
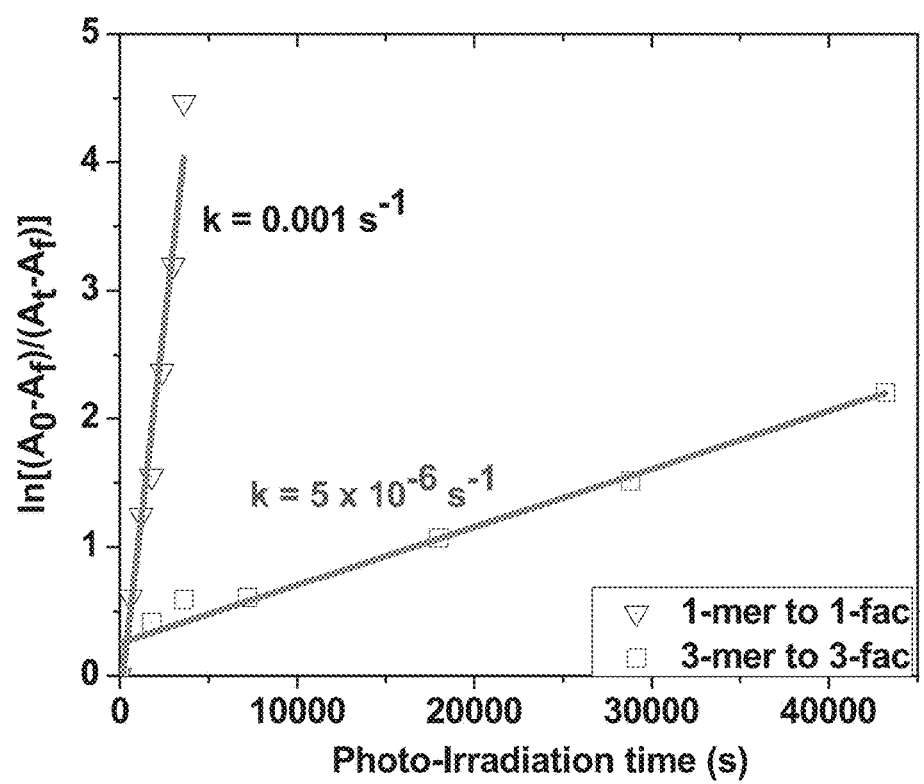
FIG. 7 is a chart showing a comparison of photo-isomerisation rate constant for (1-mer→1-fac) vs. (3-mer→3-fac).

The meridional complexes (n-mer)(n=1-3) are thermally stable, and no isomerisation to the facial complexes n-fac (n=1-3) is observed during high vacuum sublimation at high temperature (250° C.-300° C.), or heating in glycerol at 200° C. On the other hand, as shown in FIGS. 6.1, 6.2 and 6.3, photo-irradiation of the meridional complexes at 375 nm in acetonitrile leads to complete conversion to the facial complexes. The isosbestic points are clearly shown in the UV-Vis spectra. As shown in FIG. 7, the meridional complexes show different photo-isomerisation rate in acetonitrile. Isomerisation of 1-mer→1-fac shows conversion rate of k=0.001 s$^{-1}$. Isomerisation of 2-mer→2-fac shows conversion rate of the same magnitude. Isomerisation of 3-mer→3-fac shows much slower conversion rate of k=5× 10$^{-6}$ s$^{-1}$, as shown in FIG. 7.

For complexes 1-mer, 1-fac, 1-Cl, 2-mer, 2-fac, 3-mer, and 3-fac, the emission at low temperature (77K), room temperature (298 K), radiative rate ($k_r$), non-radiative rate ($k_{nr}$), and quantum yield (Q.Y.) are listed below:

| | Emission 77 k | | Emission 298 k | | | | |
|---|---|---|---|---|---|---|---|
| Complex | $\lambda_{0-0}$ (nm) | τ (μs) | $\lambda_{max}$ (nm) | τ (μs) | $k_r$(s$^{-1}$) | $k_{nr}$(s$^{-1}$) | Q. Y. (%) |
| 1-Cl | 488 | 12300 | 538 | — | — | — | — |
| 1-mer | 518 | 660 | 570 | 171 | — | — | <5 |
| 1-fac | 530 | 350 | 584 | 120 | 1.67 × 10$^3$ | 6.67 × 10$^3$ | 20 |
| 2-mer | 476 | 580 | 518 | 34 | — | — | <1.7 |
| 2-fac | 484 | 380 | 526 | 78 | 3.08 × 10$^3$ | 9.74 × 10$^3$ | 24 |
| 3-mer | 530 | 232 | 590 | 76 | 1.05 × 10$^3$ | 1.21 × 10$^4$ | 8 |
| 3-fac | 490 | 39 | 556 | 4.2 | 1.18 × 10$^5$ | 1.21 × 10$^5$ | 49.5 |

The absorption and emission spectra of all complexes are recorded in CH$_2$Cl$_2$ at room temperature. The emission spectra of the complexes at low temperature (77K) are recorded in the glass composed of 2-methyltetrahydrofuran (2-MeTHF) and dropwise of CH$_2$Cl$_2$. FIGS. 8.1, 8.2 and 8.3 show the absorption and emission spectra of compounds 1-mer, 1-fac, and 1-Cl, while FIGS. 9.1 and 9.2 show the absorption and emission spectra of compounds 2-mer, and 2-fac. FIGS. 10.1 and 10.2 show the absorption and emission spectra of compounds 3-mer, and 3-fac. In summary, both meridional and facial isomers of complexes 1, 2 and 3 show intensive highly structured emission at 77K in the glass of 2-MeTHF and drops of dichloromethane.

The absorption spectra of these complexes show intense bands in the ultraviolet part of the spectra below 300 nm. The bands are assigned to the ligand attributed (π→π*) transitions. These bands are accompanied by weaker and broader bands at lower wavelength from 300 to 450 nm. The relatively weak extinction coefficient of around $10^4$ $M^{-1}$ $cm^{-1}$ indicates the mixing from both metal-to-ligand charge transfer transitions (MLCT) and spin-allowed transitions of the ligand. In general, shoulders in the absorption spectra of the complexes n-fac (n=1-3) at around 350 nm indicates that facial isomers show stronger MLCT transitions than the meridional isomers.

At room temperature, the phosphorescent emission from complex 1-Cl and meridional complexes n-mer (n=1-3) in solution show broad band emission with rough vibronic features consistent with emission from naphthalene and (iso)quinoline. Comparing with the non-cyclometalated complex 1-Cl, the cyclometalated complexes 1-mer and 1-mer show less featured and red-shifted emission bands (See FIGS. 8.1, 8.2 and 8.3). As shown in FIGS. 9.1 and 9.2, cyclometalated complexes 2 also show featured emission band. FIGS. 10.1 and 10.2 show that the 3-complexes exhibit the least structured emission band, indicating more MLCT character of the molecules. The quantum yield of the meridional complexes 1-mer and 2-mer is less than 5%, and the actual quantum efficiency is difficult to determine since the meridional isomers start photoisomerisation when exposed to a xenon lamp. Complex 3-mer exhibits a stronger phosphorescent emission of 8% quantum yield. The facial isomer of the complexes shows significantly higher quantum yield than the meridional isomers. For complex 3-mer, the non-radiative rate is an order of magnitude higher than its radiative rate. The non-radiative rates of the facial complexes are in the same order of magnitude as their radiative rate.

Figure 11:
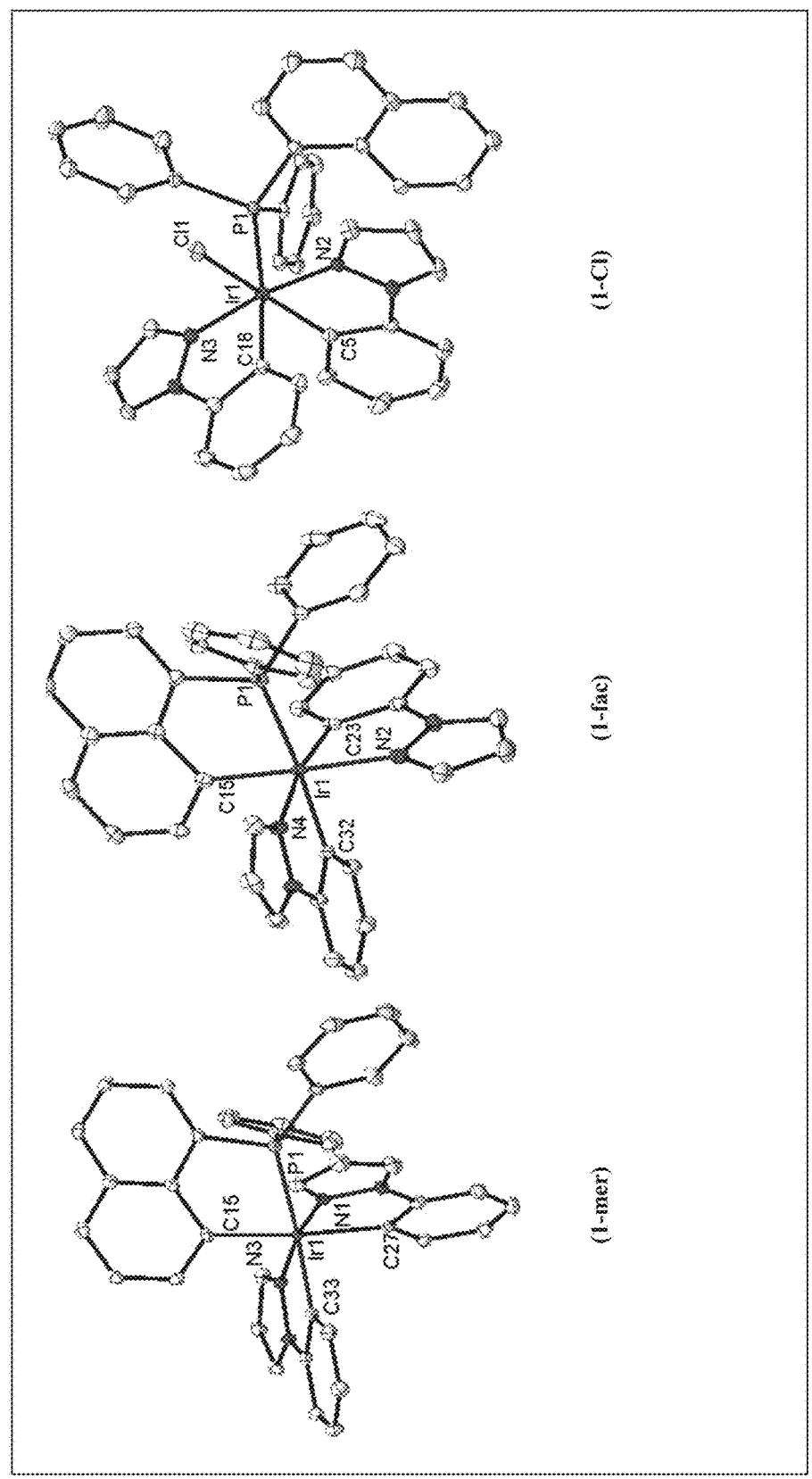
FIG. 11 shows Oak Ridge Thermal Ellipsoid Plot (OR-TEP) drawings of 1-mer, 1-fac, and 1-Cl shown in 50% probability thermal ellipsoids, with the hydrogen atoms omitted for clarity.

Single crystals of compounds 1-mer, 1-fac, and 1-Cl were grown from dichloromethane/hexane bilayer solution and characterized using X-Ray crystallography. All three complexes have the coordinated ligand arranged in qseudo-octahedral geometry. The Ir—N bond lengths in complex1-mer (Ir1-N1=2.0153(2) Å, Ir1-N3=2.0447(2) Å) are similar as those in the non-cyclometallated complex 1-Cl (Ir1-N2=2.016(2) Å, Ir1-N3=2.032(2) Å); but are shorter than those in complex 1-fac (Ir1-N2=2.1078(2) Å, Ir1-N3=2.1202(2) Å). Ir1-P1 bond length is shorten in the cyclometallated complexes 1-mer (2.3109(4) Å) and 1-fac (2.3011(5) Å), comparing with that of the complex 1-Cl (2.4164(6) Å). Due to the trans-phenyl effect, Ir—C bond lengths of 1-mer(Ir1-C15=2.111(2) Å, Ir1-C27=2.090(2) Å, Ir1-C33=2.0590(2) Å) are longer than those of 1-fac (Ir1-C15=2.0551(2) Å, Ir1-C23=2.0354(2) Å, Ir1-C32=2.0740(2) Å) and 1-Cl (Ir1-C18=2.046(2) Å, Ir1-C5=2.027(2) Å). FIG. 11 shows ORTEP drawings of the 1-mer, 1-fac, and 1-Cl complexes.

Although not wishing to be bound by theory, it is believed that the enhanced emission efficiencies for the 2 and 3-complexes is due to the larger degree of MLCT character in the excited states of these complexes, relative to the 1-complexes. The increase in MLCT character is believed to be due to the higher electron accepting property of the quinolone and isoquinoline ligands, relative to a naphthyl ligand. This explanation is consistent with the low emission efficiencies reported for known iridium C^P complexes. For those cases where the emission is clearly from the Iridium C^P, the C^P ligand contains arene or 4-quinoline groups, that do not lead to MLCT character in the excited state, which is requisite for efficient phosphorescence.

The emission spectra for the 1-, 2-, and 3-complexes are consistent with emissions from an excited state that has substantial ligand character, i.e. naphthalene, quinolone or isoquinoline. The relatively low triplet energies of these organic fragments limit the emission of the iridium C^P complexes to the yellow-to-orange part of the spectrum. If is believed that it is possible to generate C^P ligands with high triplet energies which give the excited states substantial MLCT character. Such high triplet energy ligands are expected to give emission in the blue end of the electromagnetic spectrum, with high emission efficiency.

Figure 12:
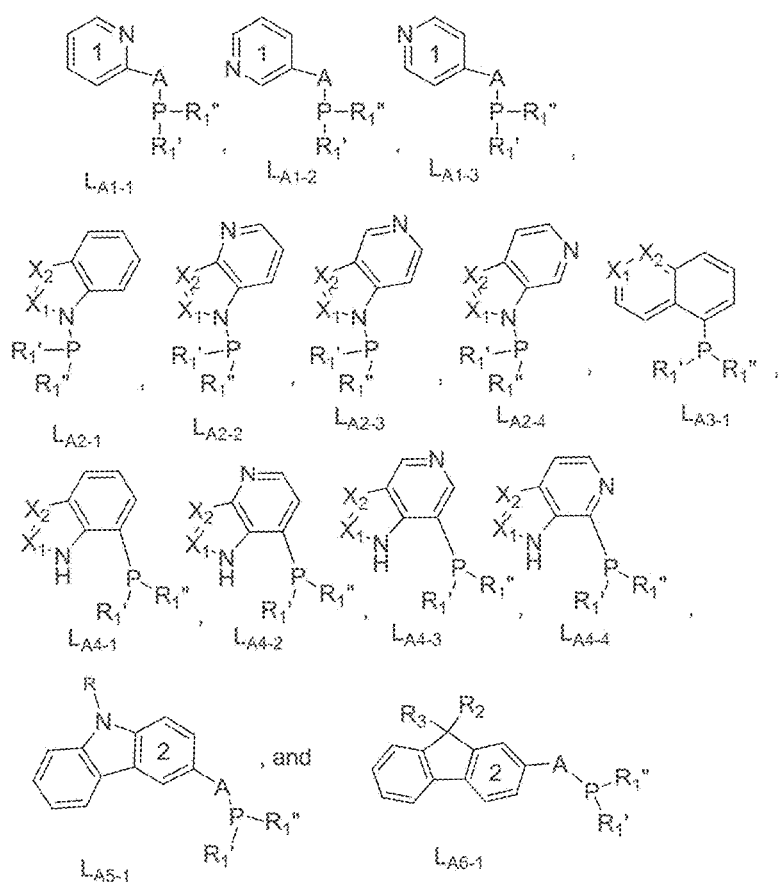
FIG. 12 shows examples of carbon-phosphine (C^P) ligands with high triplet energies.
Figure 13:
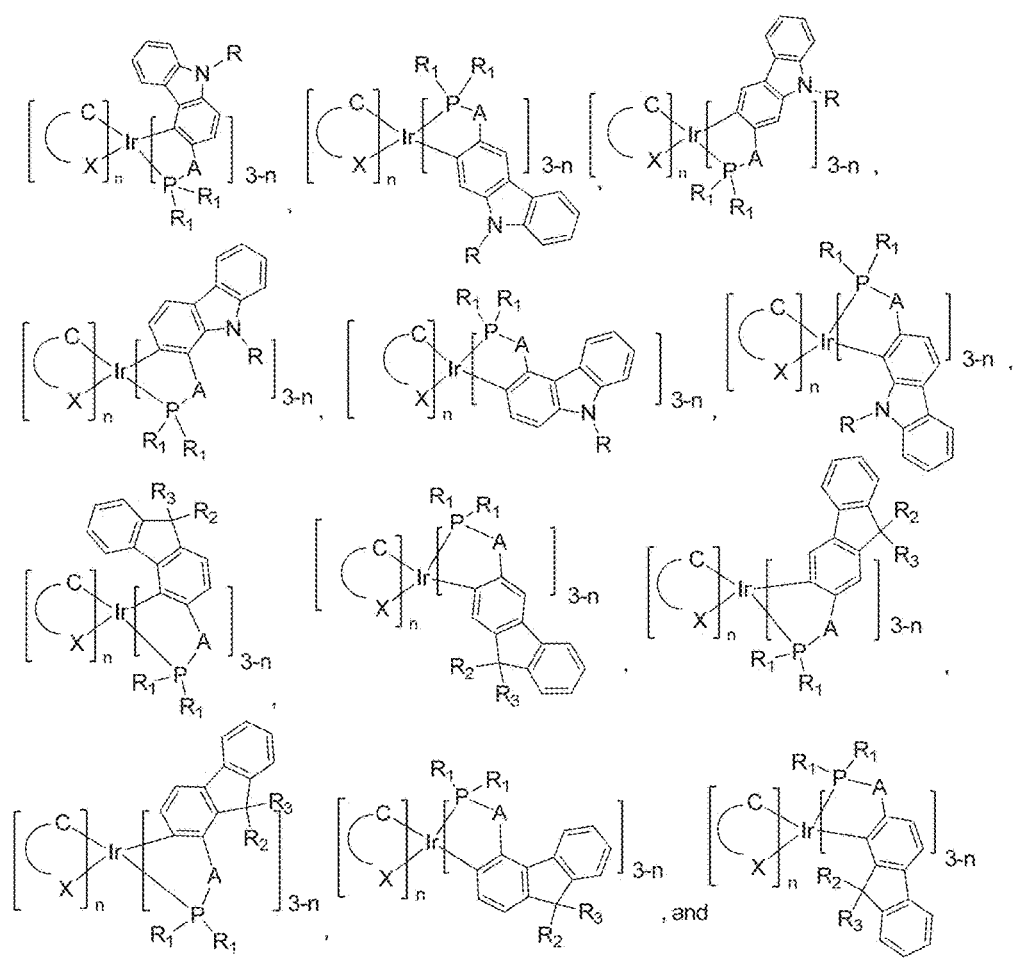
FIG. 13 shows examples of Ir(III) complexes with C^P ligands, where n=0, 1, 2.

Examples of useful C^P ligands are shown in FIG. 12. Examples of Ir(III) complexes including C^P ligands are found in FIG. 13. While the Ir(III) complexes are shown with phenylpyrazole (ppz) ligands, the ppz ligands can be replaced with any high triplet energy C^N or N^N ligand.

Synthetic Examples

All chemicals, reagents, and solvents were used as received from commercial sources without further purification. The syntheses were carried out under a nitrogen atmosphere using standard Schlenk techniques. The $^1H$ NMR and $^{31}P$ NMR spectra were measured by Varian 400 and 500NMR Spectrometer. The chemical shifts were referenced to a deuterated solvent. Elemental analyses (CHN) were performed at the Microanalysis Laboratory at the University of Illinois, Urbana-Champaign, Ill. The diphenylphosphinoaryl ligand and [(ppz)$_2$Ir(μ-Cl)]$_2$ complex were synthesized following previously reported procedures.

Evaluations of n-Mer Compounds

General Synthesis Procedure for n-Mer (n=1-3) Compounds

A mixture of [(ppz)$_2$Ir(μ-Cl)]$_2$(1 equiv), diphenylphosphinoaryl ligand (2.4 equiv), Ag$_2$O (10 equiv), and KOH pellets (20 equiv) were dissolved in 40 ml of 1,2-dichlorbenzene (oDCB), fully degassed under N$_2$, and then heated at 120° C. in dark for 18 hours. The oDCB was removed at 80° C. under low pressure. Dichloromethane was added, and the solution was filtered with a celite plug to remove the insoluble salts. The filtrate was collected and concentrated using a rotary evaporator. The crude product of n-mer(n=1-3) was purified by silica gel column chromatography eluting with hexane and ethyl acetate. For compound 3, 5 mL of ethoxyethanol was added to the oDCB solution prior to heating. The yield of compound 1-mer, 2-mer, and 3-mer were 85%, 75% and 90% respectively.

Spectra Data for Compound 1-Mer

Figure 14:
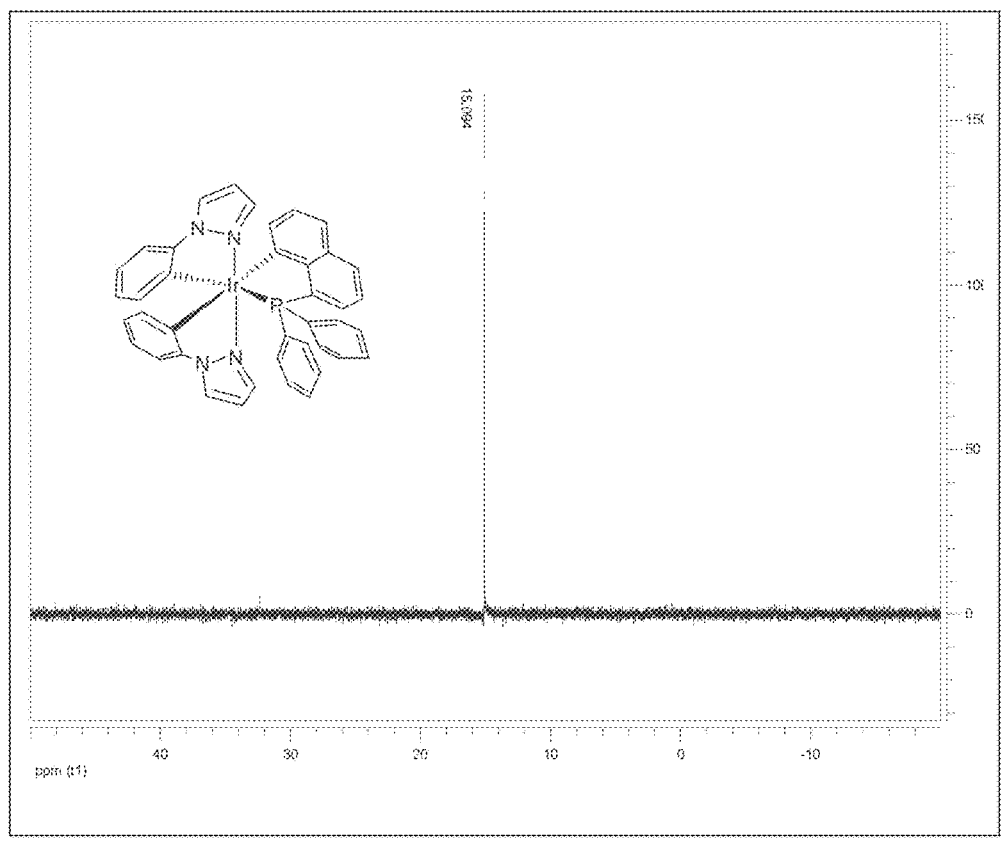
FIG. 14 is a $^{31}$P NMR (162 MHz, CDCl$_3$) spectra of compound 1-mer.

FIG. 14 shows the $^{31}P$ NMR spectra for compound 1-mer. The peaks for the $^{31}P$ NMR (202 MHz, CDCl$_3$, 298 K) spectra was at δ=15.09 (s).

Figure 15:
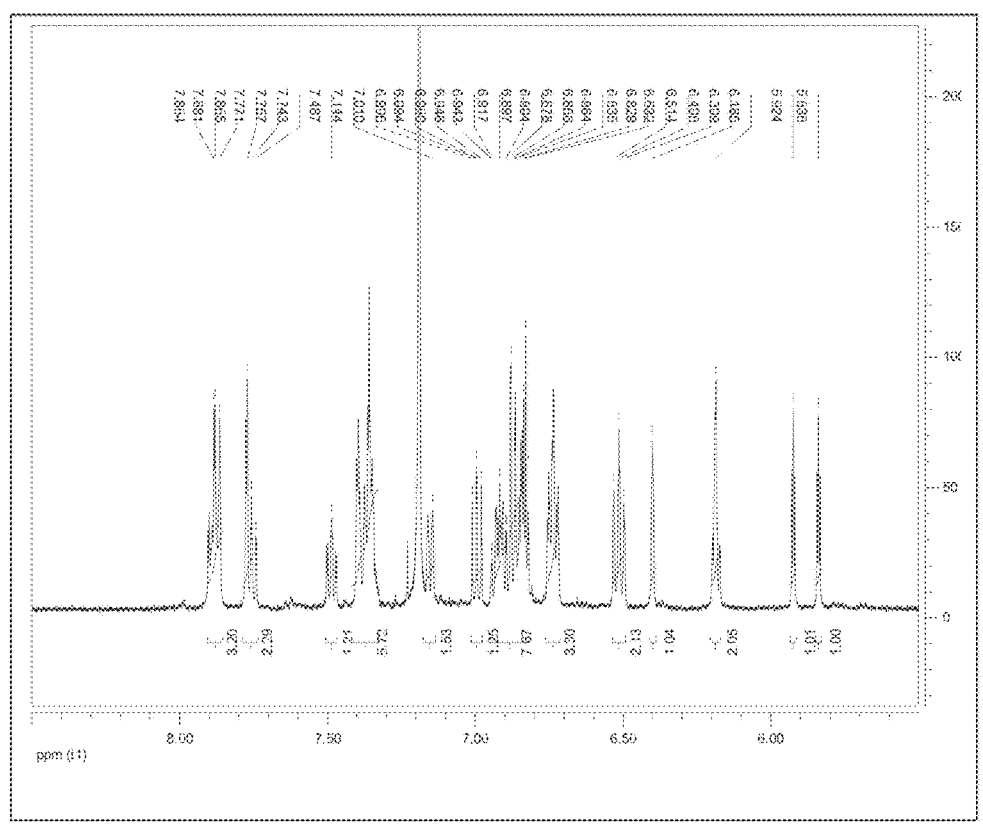
FIG. 15 is a $^1$H NMR (500 MHz, CDCl$_3$) spectra of compound 1-mer.

FIG. 15 shows the $^1H$ NMR spectra for compound 1-mer. The peaks for the $^1HNM$ (500 MHz, CDCl$_3$, 298 K) spectra were at δ=7.88-7.90 (m, 2H), 7.86 (d, J=3 Hz, 1H), 7.77 (d, J=2.7 Hz, 1H), 7.75 (dt, $J_1$=1.3 Hz, $J_2$=8.5 Hz, 1H), 7.49 (ddd, $J_1$=1.8 Hz, $J_2$=7.0 Hz, $J_3$=8.1 Hz, 1H), 7.34-7.40 (m, 5H), 7.15 (dt, $J_1$=1.2 Hz, $J_2$=7.7 Hz, 1H), 6.99 (td, $J_1$=1.2 Hz, $J_2$=7.0 Hz, H), 6.82-6.95 (m, 7H), 6.72-6.76 (m, 3H), 6.51 (ddd, $J_1$=1.2 Hz, $J_2$=8.0 Hz, $J_3$=9.3 Hz, 2H), 6.40 (m, 1H), 6.17-6.20 (m, 2H), 5.92 (t, J=2.6 Hz, 1H), 5.84 (t, J=2.7 Hz, 1H).

Figure 16:
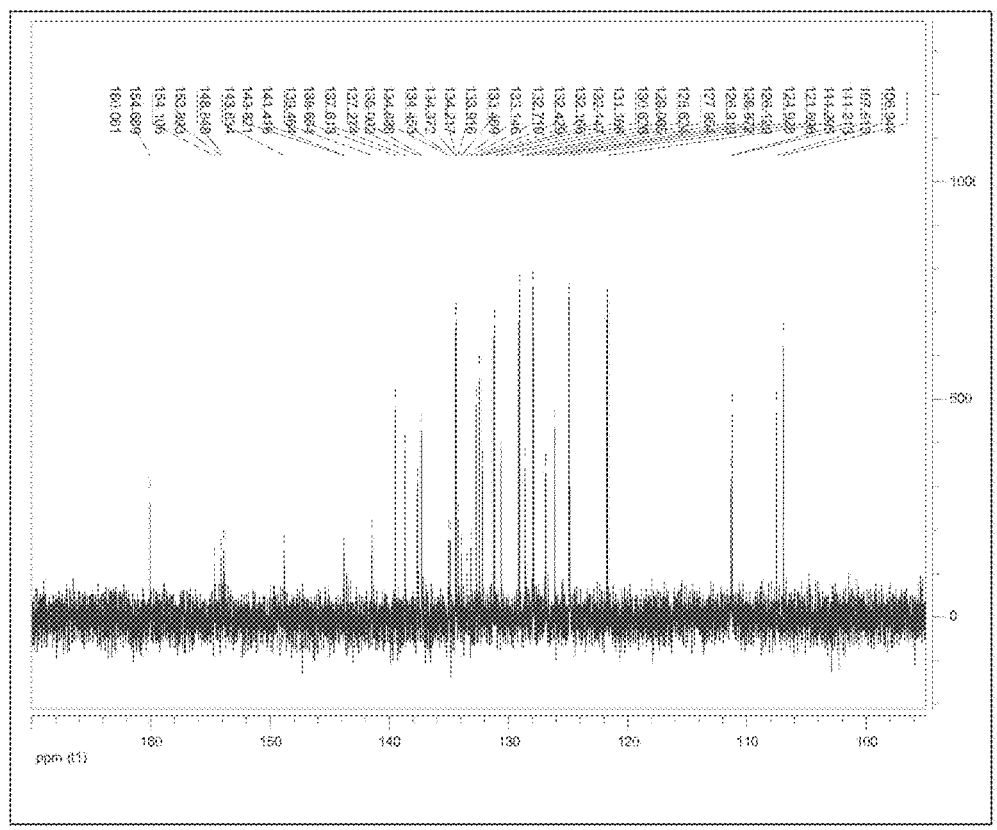
FIG. 16 is a $^{13}$C NMR (126 MHz, CDCl$_3$) spectra of compound 1-mer.

FIG. 16 shows the $^{13}C$ NMR spectra for compound 1-mer. The peaks for the $^{13}C$ NMR (126 MHz, 298 K) spectra were at δ=160.1 (s), 154.6 (s), 154.1 (s), 153.9 (s), 148.8 (s), 143.8 (d), 141.4 (d), 139.4 (d), 138.6 (d), 137.6 (d), 137.2 (d), 135.0 (s), 134.8 (s), 134.4 (d), 134.2 (s), 133.9 (s), 133.4 (s), 133.1 (s), 132.7 (d), 132.4 (d), 132.1 (d), 131.2 (d), 130.6 (d), 129.0 (d), 128.6 (d), 127.9 (d), 127.8 (d), 126.9

(d), 126.1 (d), 124.9 (d), 124.8 (d), 121.7 (d), 111.3 (d), 111.2 (d), 107.5 (d), 106.9 (d).

Analysis using liquid chromatography-mass spectroscopy (LC-MS) with electrospray ionization (ESI) indicated in a mass to charge (m/z) ratio of 791.25 ([M+1]$^+$, calcd: 790.18). The analytically calculated chemical formula was $C_{40}H_{30}IrN_4P$ (Calculated: C, 60.82; H, 3.83; N, 7.09. Found: C, 61.36; H, 3.79; N, 7.15).

Spectra Data for Compound 2-Mer

Figure 22:
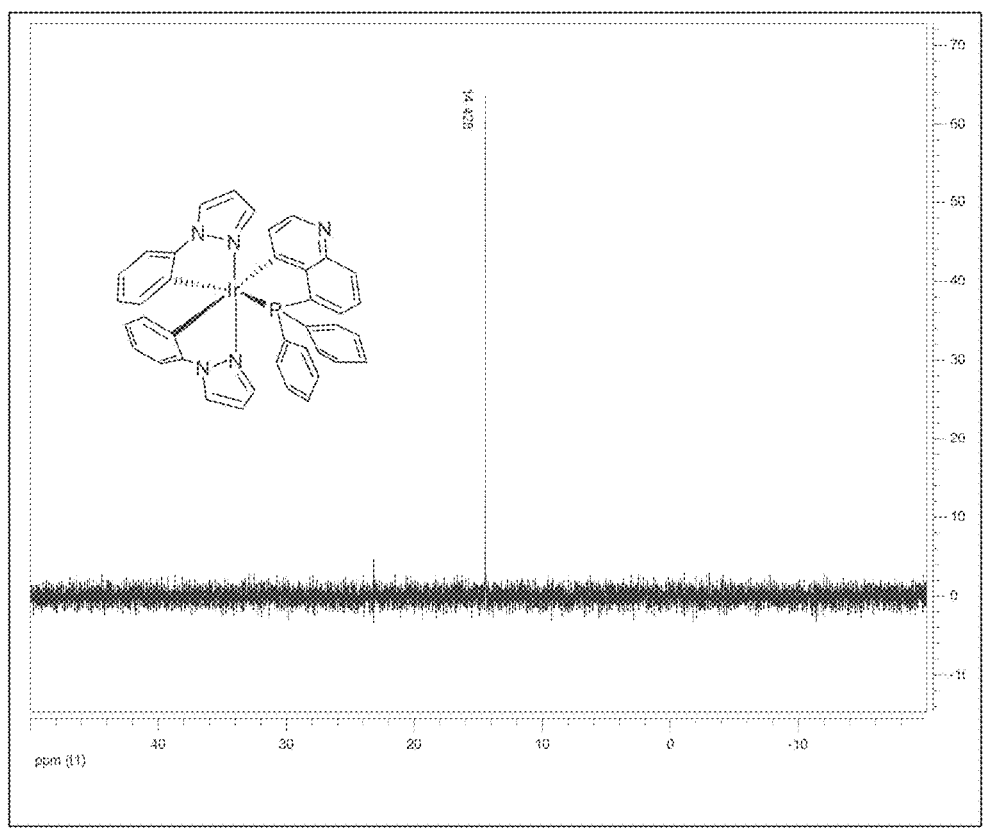
FIG. 22 is a $^{31}$P NMR (162 MHz, CDCl$_3$) spectra of compound 2-mer.

FIG. 22 shows the $^{31}P$ NMR spectra for compound 2-mer. The peak for the $^{31}P$ NMR (202 MHz, CDCl$_3$, 298 K) spectra was at δ=14.43 (s).

Figure 23:
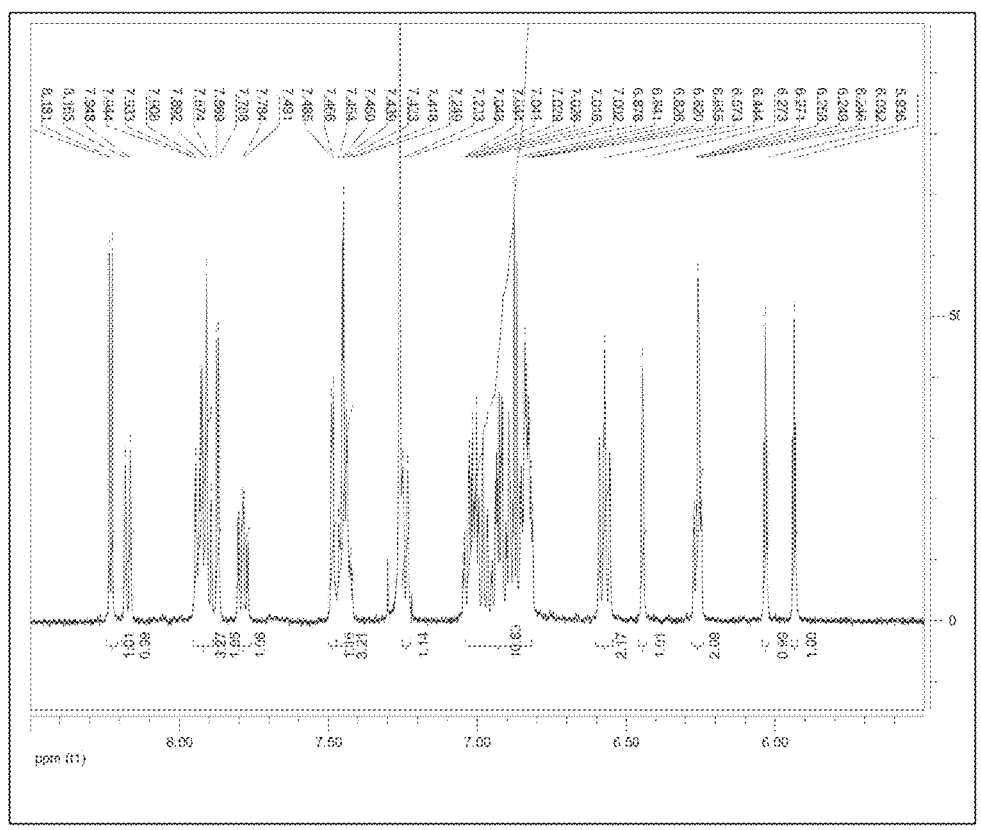
FIG. 23 is a $^1$H NMR (500 MHz, CDCl$_3$) spectra of compound 2-mer.

FIG. 23 shows the $^1H$ NMR spectra for compound 2-mer. The peaks for the $^1HNMR$ (500 MHz, CDCl$_3$, 298 K) spectra were at δ=8.23 (d, J=4.4 Hz, 1H), 8.17 (dt, J$_1$=1.5 Hz, J$_2$=8.2 Hz, 1H), 7.89-7.95 (m, 3H), 7.87 (d, J=2.9 Hz, 1H), 7.79 (ddd, J$_1$=2.3 Hz, J$_2$=5.6 Hz, J$_3$=7.1 Hz, 1H), 7.49 (d, J=2.9 Hz, 1H), 7.41-7.47 (m, 3H), 7.24 (dt, J$_1$=1.0 Hz, J$_2$=7.9 Hz, 1H), 6.81-7.05 (m, 10H), 6.57 (ddd, J$_1$=1.0 Hz, J$_2$=8.0 Hz, J$_3$=9.5 Hz, 2H), 6.57 (m, 1H), 6.24-6.27 (m, 2H), 6.03 (t, J=2.6 Hz, 1H), 5.94 (t, J=2.6 Hz, 1H).

Figure 24:
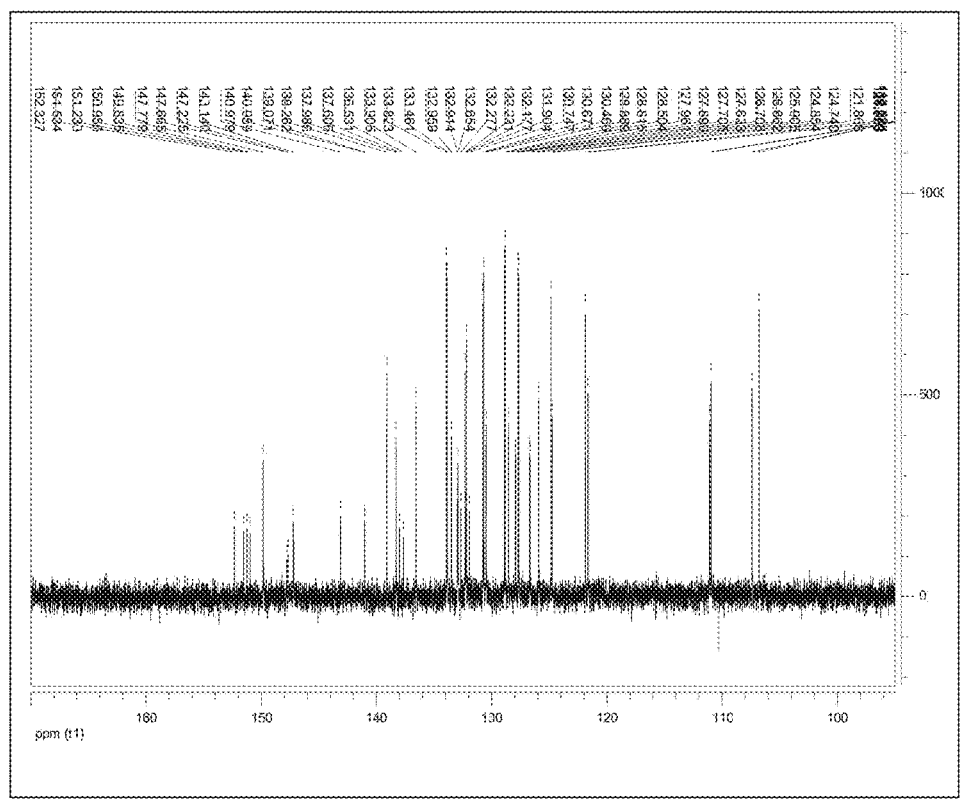
FIG. 24 is a $^{13}$C NMR (126 MHz, CDCl$_3$) spectra of compound 2-mer.

FIG. 24 shows the $^{13}C$ NMR spectra for compound 2-mer. The peaks for the $^{13}C$ NMR (126 MHz, CDCl$_3$, 298 K) spectra were at δ=152.3 (s), 151.5 (s), 151.2 (s), 150.9 (s), 149.8 (d), 147.6 (d), 147.2 (d), 143.1 (d), 140.9 (d), 139.1 (d), 138.3 (d), 137.9 (d), 137.6 (d), 136.5 (d), 133.9 (d), 133.5 (d), 133.0 (s), 132.3 (d), 132.2 (s), 132.1 (d), 131.9 (s), 130.7 (d), 130.5 (d), 129.4 (d), 128.8 (d), 128.5 (d), 127.9 (d), 127.7 (d), 126.7 (d), 125.9 (d), 124.9 (d), 124.7 (d), 121.9 (d), 121.7 (d), 121.7 (d), 111.1 (d), 110.9 (d), 107.4 (d), 106.8 (d).

Analysis using LC-MS with ESI indicated in a mass to charge (m/z) ratio of 791.20 ([M], calcd: 791.18). The analytically calculated chemical formula was $C_{39}H_{29}IrN_5P$ (Calculated: C, 59.23; H, 3.7; N, 8.86. Found: C, 58.78; H, 3.51; N, 8.58).

Spectra Data for Compound 3-mer

Figure 28:
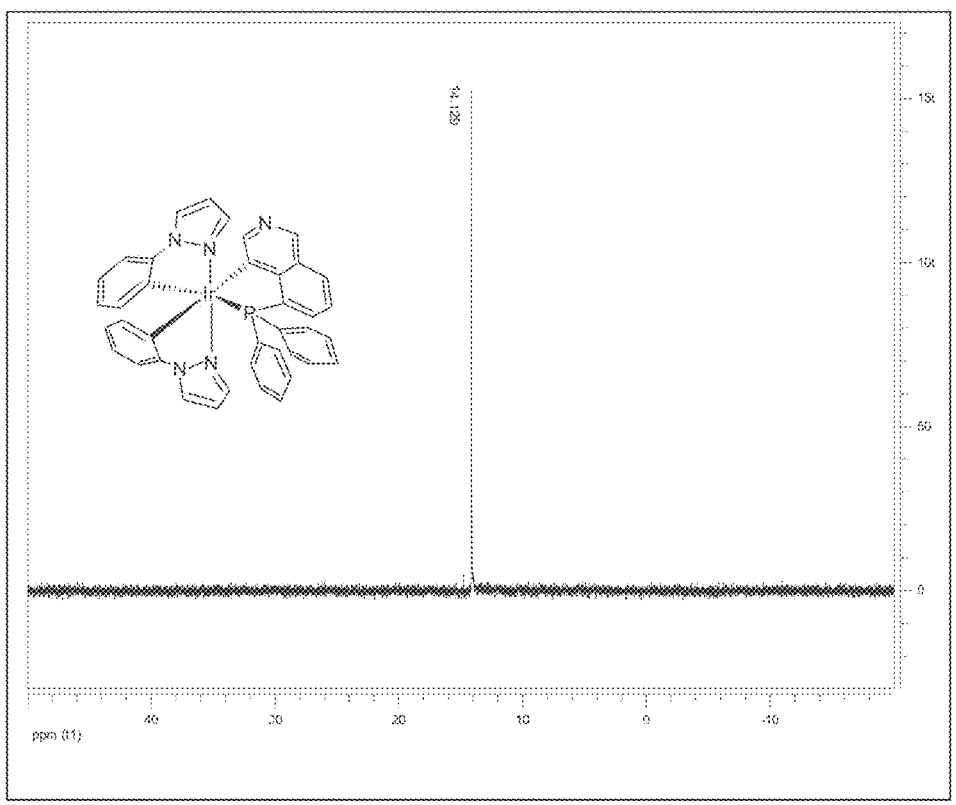
FIG. 28 is a $^{31}$P NMR (162 MHz, CDCl$_3$) spectra of compound 3-mer.

FIG. 28 shows the $^{31}P$ NMR spectra for compound 3-mer. The peak for the $^{31}P$ NMR (162 MHz, CDCl$_3$, 298 K) spectra was at δ=14.13 (s).

Figure 29:
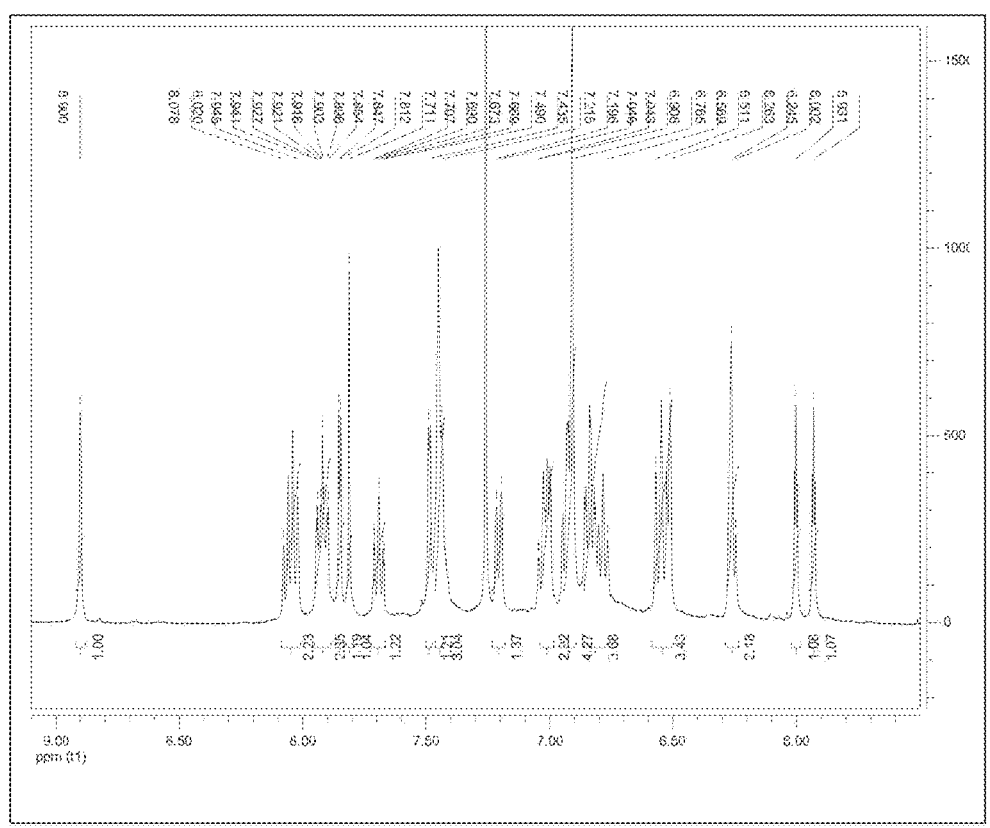
FIG. 29 is a $^1$H NMR (500 MHz, CDCl$_3$) spectra of compound 3-mer.

FIG. 29 shows the $^1H$ NMR spectra for compound 3-mer. The peaks for the $^1H$ NMR (400 MHz, CDCl$_3$, 298 K) were at δ=8.90 (s, 1H), 8.02-8.08 (m, 2H), 7.89-7.95 (m, 2H), 7.85 (d, J=2.8 Hz, 1H), 7.81 (s, 1H), dt, 7.69 (J$_1$=1.5 Hz, J$_2$=8.0 Hz, 1H), 7.43-7.49 (m, 4H), 7.21 (d, J=8.0 Hz, 1H), 6.76-7.04 (m, 9H), 6.51-6.57 (m, 3H), 6.24-6.27 (m, 2H), 6.00 (t, J=2.5 Hz, 1H), 5.93 (t, J=2.5 Hz, 1H).

Figure 30:
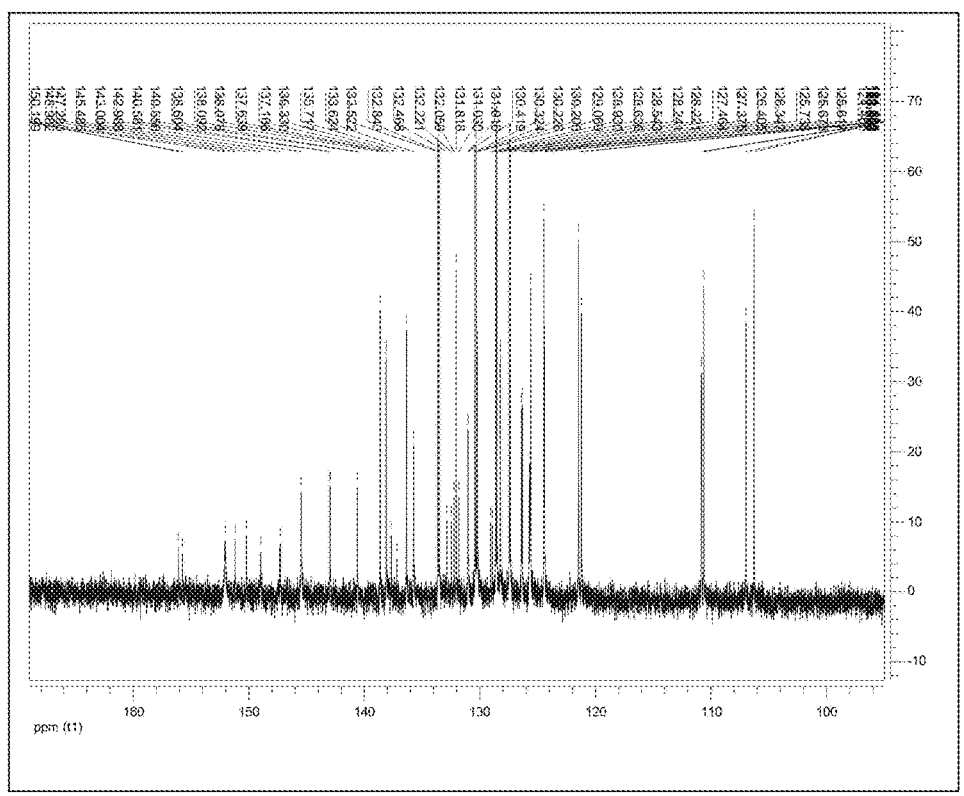
FIG. 30 is a $^{13}$C NMR (126 MHz, CDCl$_3$) spectra of compound 3-mer.

FIG. 30 shows the $^{13}C$ NMR spectra for compound 3-mer. The peaks for the $^{13}C$ NMR (101 MHz, CDCl$_3$, 298 K) were at δ=156.0 (s), 155.7 (s), 152.0 (d), 151.2 (d), 150.2 (s), 148.9 (d), 147.2 (d), 145.5 (d), 143.0 (d), 140.5 (d), 138.6 (d), 138.0 (d), 136.3 (d), 135.7 (d), 133.6 (d), 132.8 (s), 132.4 (s), 132.2 (s), 132.0 (d), 131.8 (s), 131.0 (d), 130.4 (d), 130.2 (d), 129.1 (s), 128.9 (s), 128.6 (d), 128.2 (d), 127.4 (d), 126.4 (d), 125.7 (d), 125.6 (d), 124.5 (d), 124.4 (d), 121.5 (d), 121.2 (d), 110.8 (d), 111.6 (d), 106.9 (d), 106.3 (d).

Maldi-MS analysis indicated in a mass to charge (m/z) ratio of 791.86 ([M]$^+$, calculated: 791.18).

Evaluations of 1-Cl Compound

Synthesis of Compound 1-Cl

The [(ppz)$_2$Ir(μ-Cl)]$_2$ (1 equiv), Ag$_2$O (10 equiv), and PPh$_2$-naphthalene ligand (2.2 equiv) were refluxed under N2 atmosphere in 40 mL of 1,2-dichlorethane (DCE) for 18 h. After the mixture was cooled to room temperature, a celite plug was used to remove any insoluble salts in the solution mixture. Then, the DCE was removed via rotavap. The crude product was chromatographed on silica gel with hexane and ethyl acetate (6:4) as the eluents to yield 70% pure 1-C$_1$.

Spectra Data for Compound 1-Cl

Figure 20:
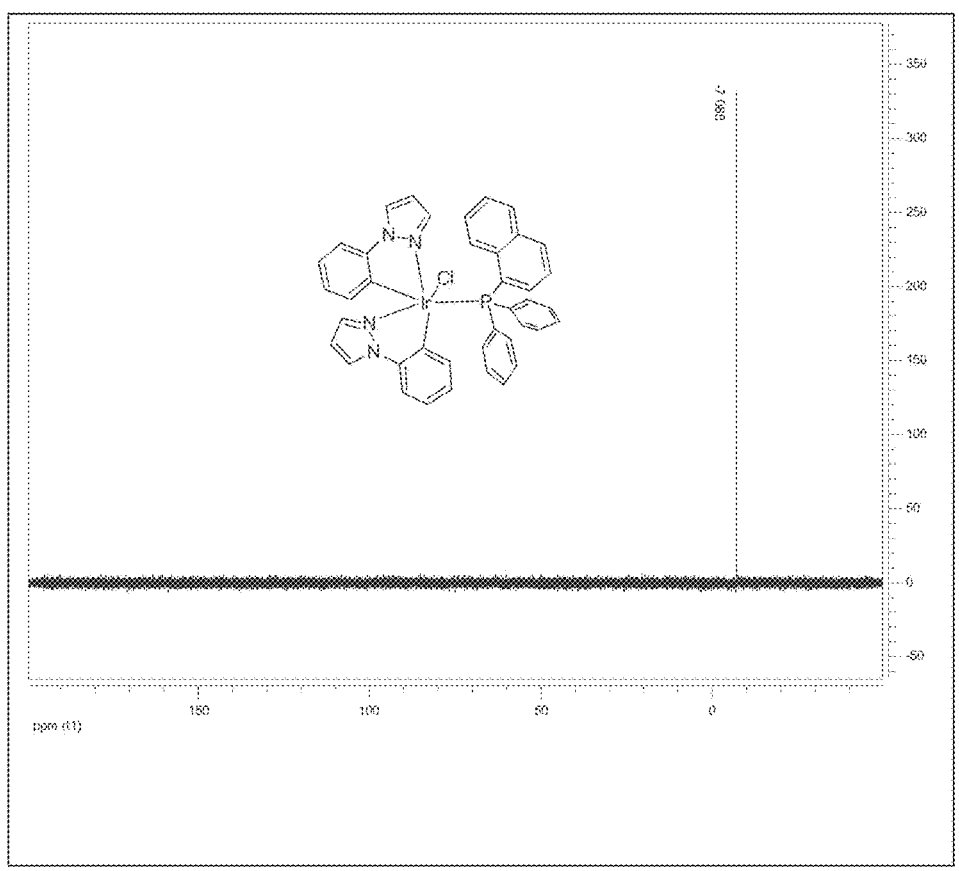
FIG. 20 is a $^{31}$P NMR (162 MHz, CD$_2$Cl$_2$) spectra of compound 1-Cl.

FIG. 20 shows the $^{31}C$ NMR spectra for compound 1-Cl. The peaks for the $^{31}P$ NMR (162 MHz, CD$_2$Cl$_2$, 298 K) spectra were at δ=−7.9 (s).

Figure 21:
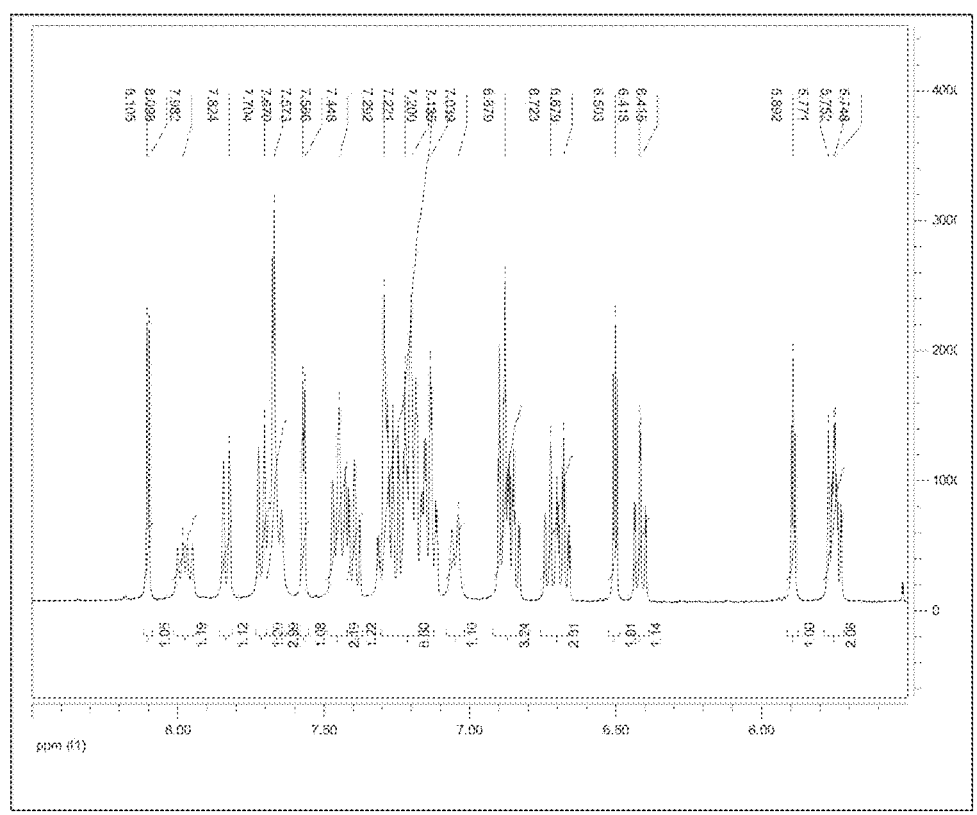
FIG. 21 is a $^1$H NMR (400 MHz, CD$_2$Cl$_2$) spectra of compound 1-Cl.

FIG. 21 shows the $^1H$ NMR spectra for compound 1-Cl. The peaks for the $^1H$ NMR (400 MHz, CD$_2$Cl$_2$, 297 K) spectra were at δ=8.10 (d, J=2.9 Hz, 1H), 7.97 (dd, J$_1$=7.2 Hz, J$_2$=13.0 Hz, 1H), 7.83 (d, J=8.2 Hz, 1H), 7.65-7.72 (m, 4H), 7.57 (dt, J$_1$=1.0 Hz, J$_2$=3.0 Hz, 1H), 7.37-7.47 (m, 3H), 7.11-7.31 (m, 9H), 7.05 (d, J=8.5 Hz, 1H), 6.83-6.90 (m, 3H), 6.65-6.74 (m, 3H), 6.42 (dt, J$_1$=1.2 Hz, J$_2$=7.5 Hz, 1H), 5.89 (t, J=2.5 Hz, 1H), 5.72-5.77 (m, 2H).

Compound 1-Cl was evaluated using $^{13}C$ NMR. The peaks for the $^{13}C$ NMR (101 MHz, CD$_2$Cl$_2$, 298 K) spectra were at δ=145.2 (s), 143.7 (d), 142.6 (d), 142.2 (s), 139.3 (d), 137.2 (d), 135.8 (d), 134.7 (s), 134.6 (s), 134.5 (d), 134.4 (d), 134.3 (d), 134.1 (s), 134.0 (s), 133.9 (s), 133.5 (s), 132.7 (d), 132.1 (d), 130.4 (s), 130.2 (d), 129.3 (d), 129.2 (d), 127.8 (s), 127.7 (d), 127.4 (d), 127.0 (d), 126.1 (d), 125.9 (d), 125.4 (t), 123.6 (d), 122.2 (d), 111.8 (d), 111.0 (d), 108.4 (d), 107.1 (d).

Analysis using LC-MS with ESI indicated in a mass to charge (m/z) ratio of 791.25 ([M-Cl]$^+$, calcd: 826.16). The analytically calculated chemical formula was $C_{40}H_{31}ClIrN_4P$ (Calculated: C, 58.14; H, 3.78; N, 6.78. Found: C, 55.79; H, 3.65; N, 6.39).

Evaluations of n-Fac Compounds

General Synthesis Procedure for n-Fac (n=1-3) Compounds

An acetonitrile solution of 200 mg of the meridional complex n-mer (n=1-3) was fully degassed under N2, and then stirred in a UV reactor with irradiation at wavelength of 375 nm for 15 h. The solution was then dried. Chromatography was done on silica gel using hexane and ethyl acetate (6:4) as the eluent to yield >95% of the facial complex n-fac (n=1-3).

Spectra Data for Compound 1-fac

Figure 17:
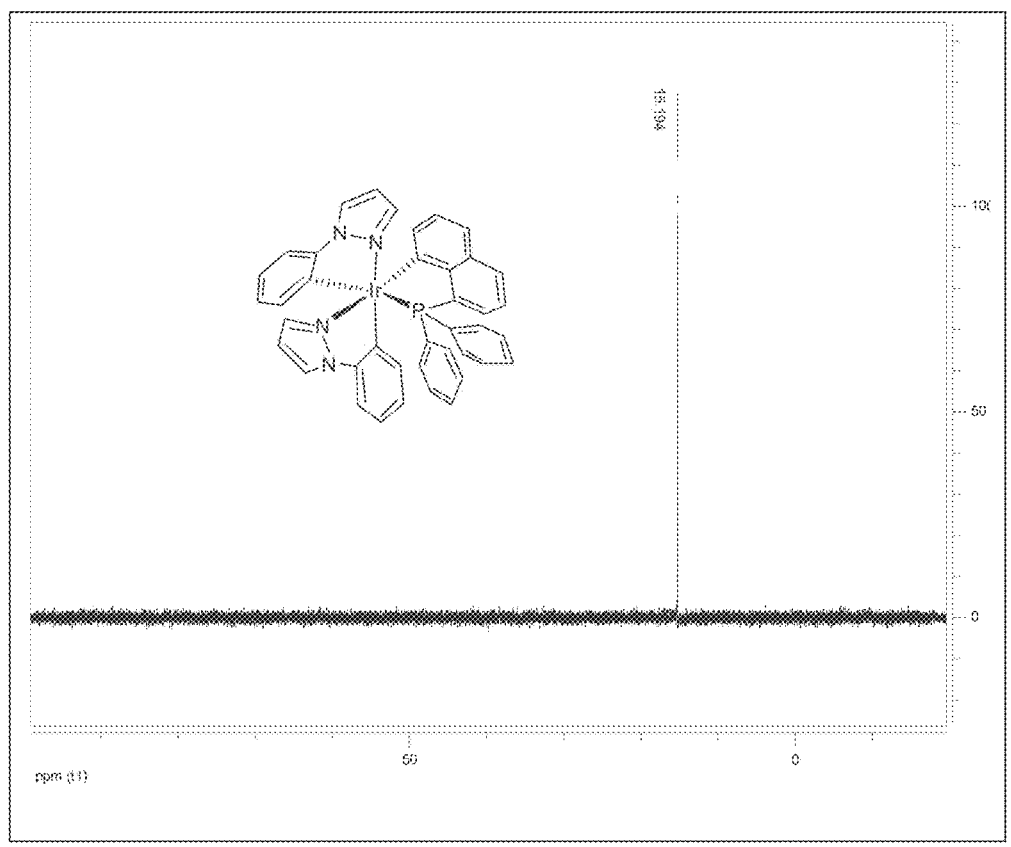
FIG. 17 is a $^{31}$P NMR (162 MHz, CDCl$_3$) spectra of compound 1-fac.

FIG. 17 shows the $^{31}P$ NMR spectra for compound 1-fac. The peak for the $^{31}P$ NMR (162 MHz, CDCl$_3$, 298 K) spectra was at δ=15.19 (s).

Figure 18:
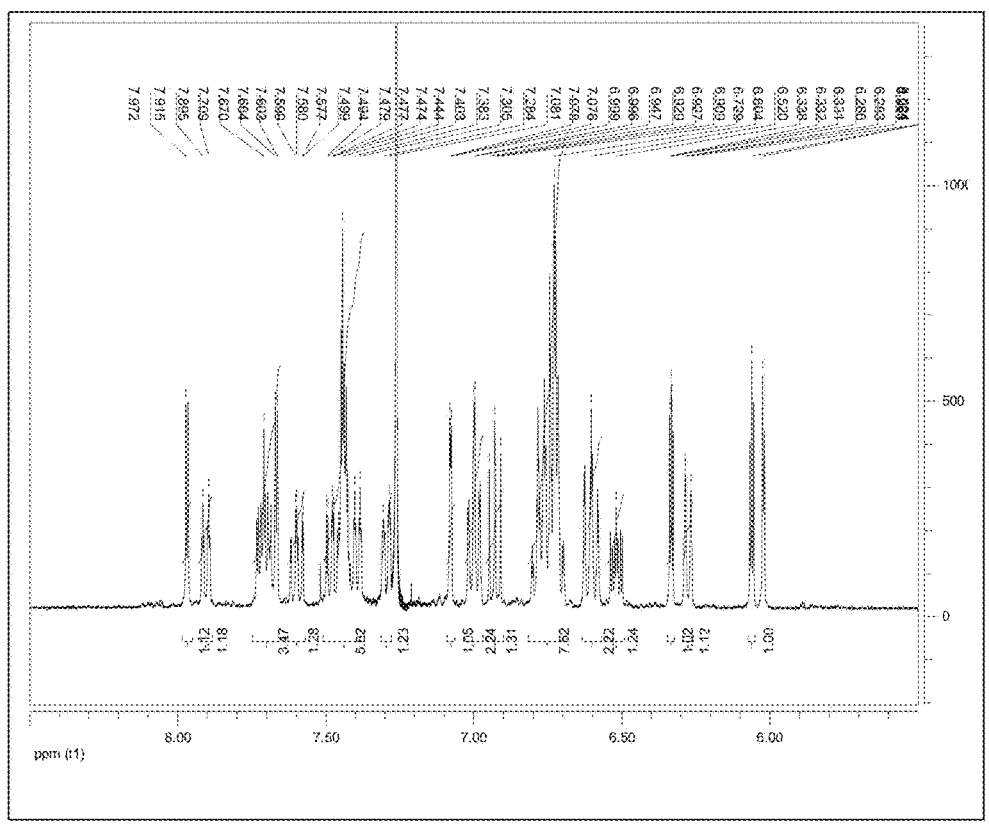
FIG. 18 is a $^1$H NMR (400 MHz, CDCl$_3$) spectra of compound 1-fac.

FIG. 18 shows the $^1H$ NMR spectra for compound 2-fac. The peaks for the $^1H$ NMR (500 MHz, CDCl$_3$, 298 K) spectra were at δ=7.97 (d, J=2.7 Hz, 1H), 7.90 (dt, J$_1$=1.4 Hz, J$_2$=8.0 Hz, 1H), 7.71 (m, 2H), 7.67 (d, J=2.7 Hz, 1H), 7.60 (ddd, J$_1$=1.2 Hz, J$_2$=7.0 Hz, J$_3$=8.2 Hz, 1H), 7.43-7.50 (m, 4H), 7.39 (dt, J$_1$=1.3 Hz, J$_2$=8.0 Hz, 1H), 7.29 (dt, J$_1$=1.4 Hz, J$_2$=8.0 Hz, 1H), 7.08 (m, 1H), 7.00 (ddd, J$_1$=1.5 Hz, J$_2$=7.0 Hz, J$_3$=8.3 Hz, 2H), 6.93 (dd, J$_1$=7.2 Hz, J$_2$=8.0 Hz, 1H), 6.70-6.80 (m, 7H), 6.60 (ddd, J$_1$=1.2 Hz, J$_2$=8.4 Hz, J$_3$=9.8 Hz, 2H), 6.52 (ddd, J$_1$=2.7 Hz, J$_2$=5.8 Hz, J$_3$=7.6 Hz, 1H), 6.33 (t, J=2.5 Hz, 1H), 6.28 (m, 1H), 6.06 (t, J=2.5 Hz, 1H), 6.02 (d, J=2.2 Hz, 1H).

Figure 19:
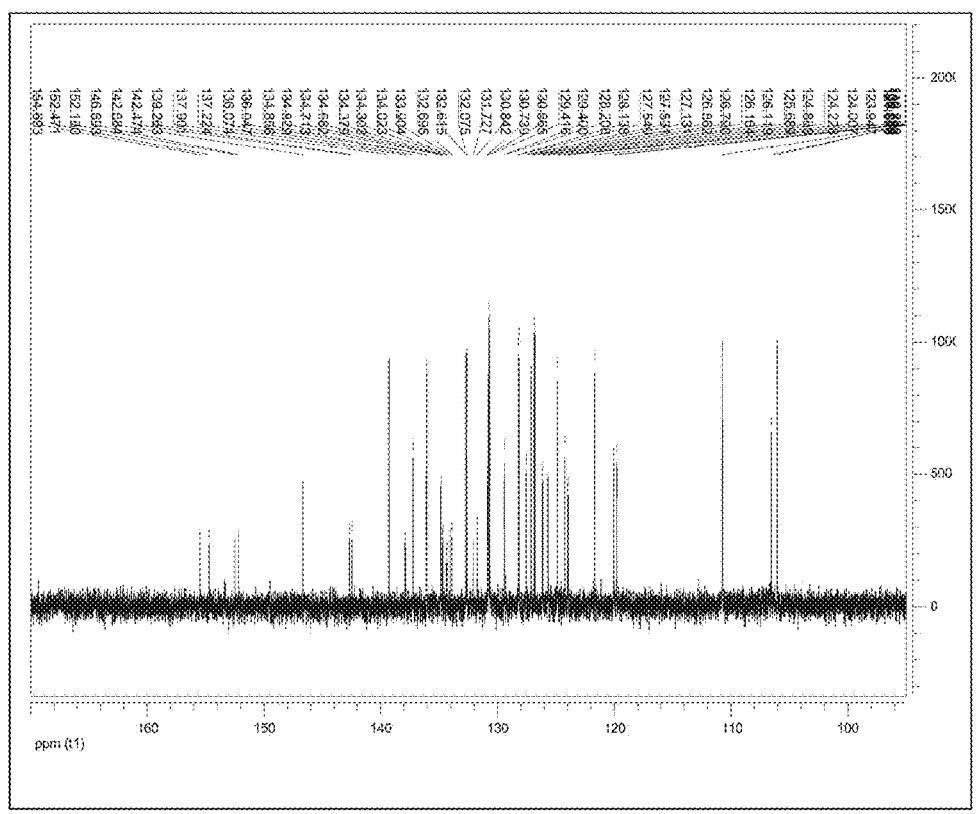
FIG. 19 is a $^{13}$C NMR (126 MHz, CDCl$_3$) spectra of compound 1-fac.

FIG. 19 shows the $^{13}C$ NMR spectra for compound 3-fac. The peaks for the $^{13}C$ NMR (126 MHz, CDCl$_3$, 298 K) were at δ=155.5 (s), 154.7 (s), 152.4 (s), 152.1 (s), 146.7 (d), 142.6 (d), 142.4 (d), 139.2 (d), 137.9 (d), 137.2 (d), 136.1 (d), 136.0 (d), 134.8 (d), 134.7 (d), 134.4 (s), 134.3 (s), 134.0 (d), 133.9 (s), 132.6 (d), 132.0 (s), 131.7 (s), 130.8 (s), 130.7 (d), 130.6 (d), 129.4 (d), 128.2 (d), 127.5 (d), 127.1

(d), 126.8 (d), 126.1 (d), 125.7 (d), 124.9 (d), 124.2 (d), 124.0 (d), 121.7 (d), 120.0 (d), 119.8 (d), 110.7 (d), 106.5 (d), 106.0 (d).

Analysis using LC-MS with ESI indicated in a mass to charge (m/z) ratio of 791.20 ([M+1]$^+$, calcd: 790.18). The analytically calculated chemical formula was $C_{40}H_{30}IrN_4P$ (Calculated: C, 60.82; H, 3.83; N, 7.09. Found: C, 59.33; H, 3.49; N, 6.74).

Spectra Data for Compound 2-fac

Figure 25:
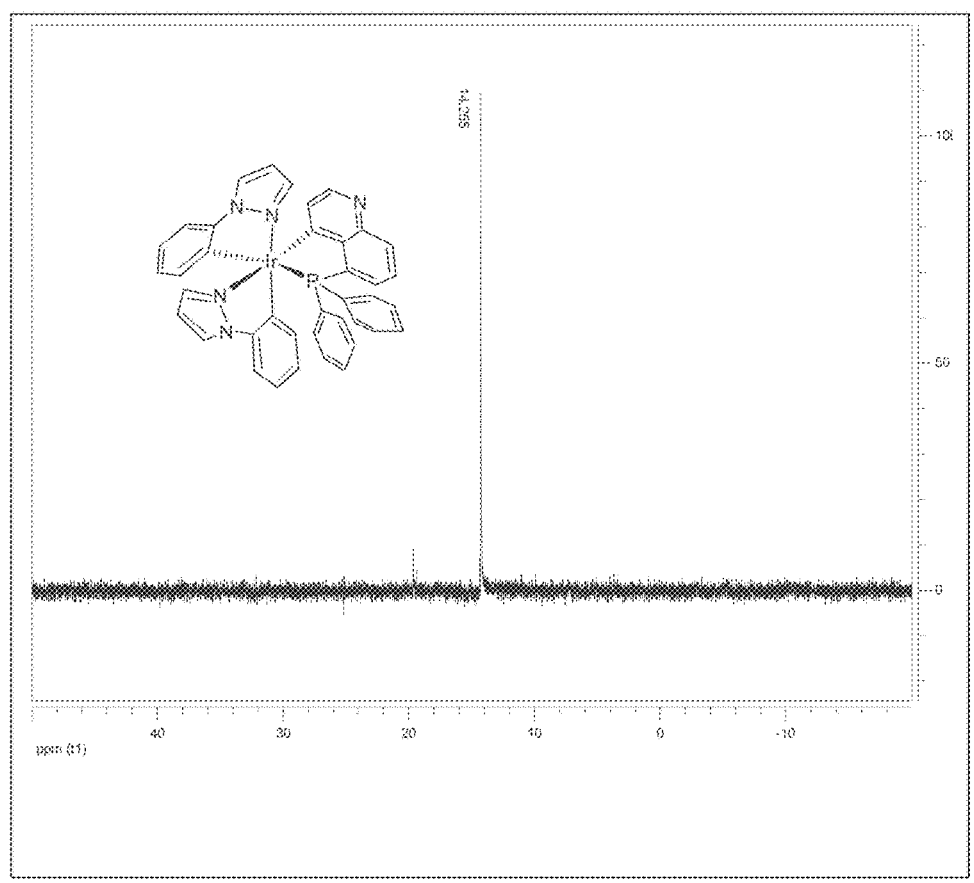
FIG. 25 is a $^{31}$P NMR (162 MHz, CDCl$_3$) spectra of compound 2-fac.

FIG. 25 shows the $^{31}$P NMR spectra for compound 2-fac. The peak for the $^{31}$P NMR (162 MHz, $CDCl_3$, 298 K) spectra was at δ=14.25 (s).

Figure 26:
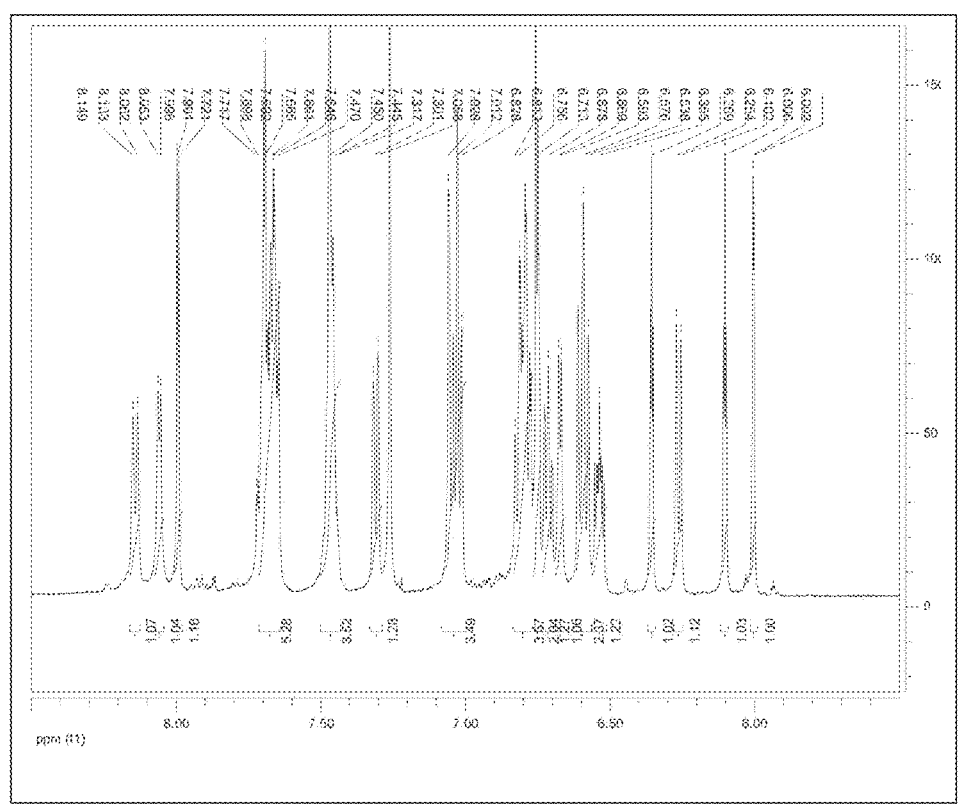
FIG. 26 is a $^1$H NMR (500 MHz, CDCl$_3$) spectra of compound 2-fac.

FIG. 26 shows the $^1$H NMR spectra for compound 2-fac. The peaks for the $^1$H NMR (400 MHz, $CDCl_3$, 298 K) spectra were at δ=8.14 (d, J=7.9 Hz, 1H), 8.06 (d, J=4.4 Hz, 1H), 7.99 (d, J=2.7 Hz, 1H), 7.64-7.72 (m, 5H), 7.44-7.48 (m, 3H), 7.31 (d, J=8.0 Hz, 1H), 7.01-7.06 (m, 3H), 6.66-6.83 (m, 7H), 6.57-6.62 (m, 2H), 6.54 (ddd, $J_1$=3.1 Hz, $J_2$=5.3 Hz, $J_3$=7.9 Hz, 1H), 6.35 (t, J=2.3 Hz, 1H), 6.26 (d, J=7.5 Hz, 1H), 6.10 (t, J=2.4 Hz, 1H), 6.00 (d, J=2.0 Hz, 1H).

Figure 27:
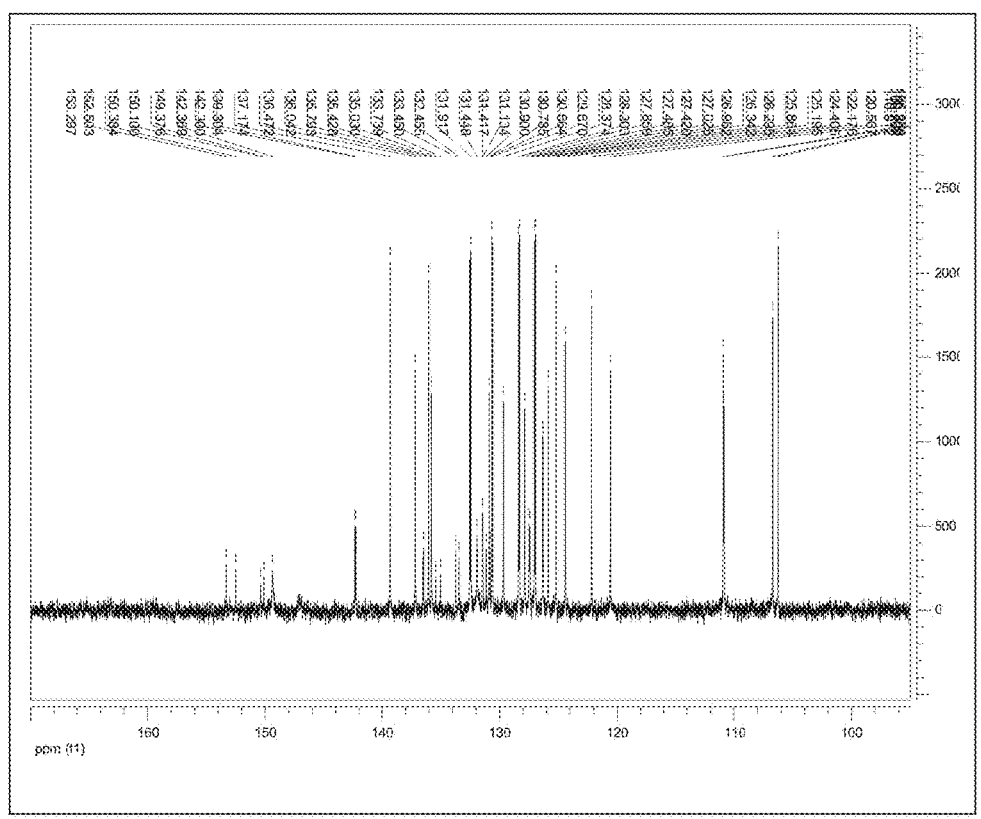
FIG. 27 is a $^{13}$C NMR (126 MHz, CDCl$_3$) spectra of compound 2-fac.

FIG. 27 shows the $^{13}$C NMR spectra for compound 2-fac. The peaks for the $^{13}$C NMR (101 MHz, 297 K) spectra were at δ=153.3 (s), 152.5 (s), 150.4 (s), 150.1 (s), 149.4 (d), 142.4 (d), 139.3 (d), 137.2 (d), 136.5 (d), 136.0 (d), 135.8 (d), 135.4 (s), 135.0 (s), 133.7 (s), 133.4 (s), 132.4 (s), 131.9 (d), 131.4 (d), 131.1 (s), 130.9 (s), 130.8 (s), 130.6 (d), 129.7 (d), 128.3 (d), 127.8 (d), 127.5 (d), 127.0 (d), 126.3 (d), 125.9 (d), 125.2 (d), 124.4 (d), 122.2 (d), 120.6 (d), 110.9 (d), 110.8 (d), 106.7 (d), 106.3 (d).

Analysis using liquid chromatography-mass spectroscopy (LC-MS) with electrospray ionization (ESI) indicated in a mass to charge (m/z) ratio of 791.20 ([M], calcd: 791.18). The analytically calculated chemical formula was $C_{39}H_{29}IrN_5P$ (Calculated: C, 59.23; H, 3.7; N, 8.86. Found: C, 59.49; H, 3.89; N, 8.09).

Spectra Data for Compound 3-fac

Figure 31:
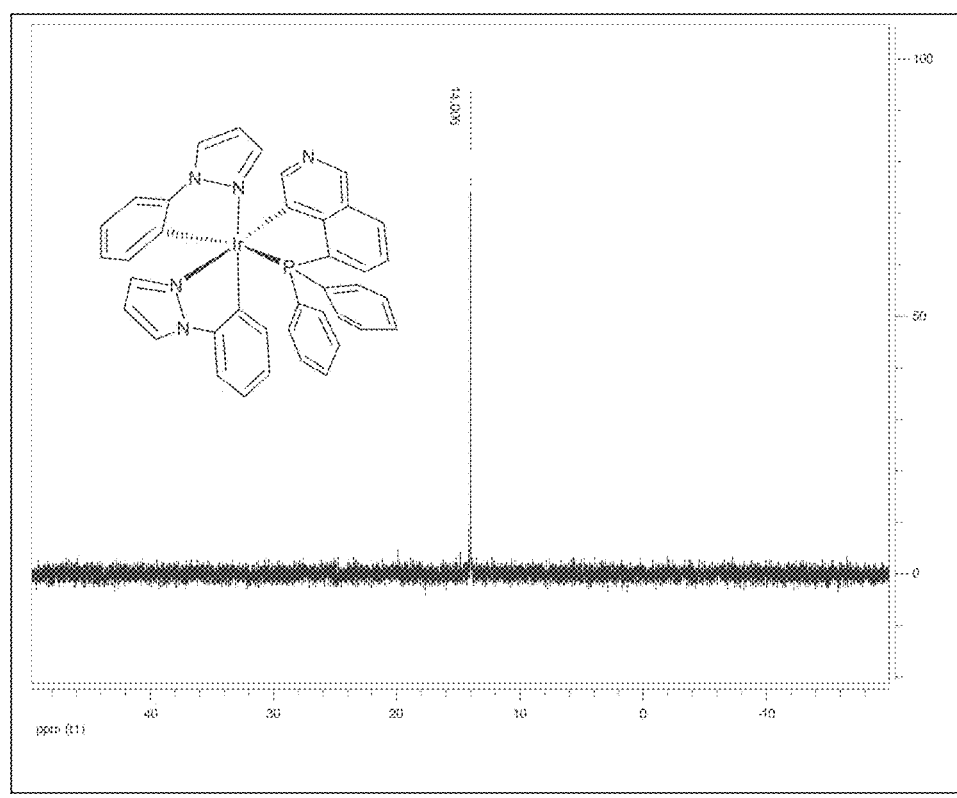
FIG. 31 is a $^{31}$P NMR (202 MHz, CD$_2$Cl$_2$) spectra of compound 3-fac.

FIG. 31 shows the $^{31}$P NMR spectra for compound 3-fac. The peak for the $^{31}$P NMR (162 MHz, $CD_2Cl_2$, 298 K) spectra was at δ=14.00 (s).

Figure 32:
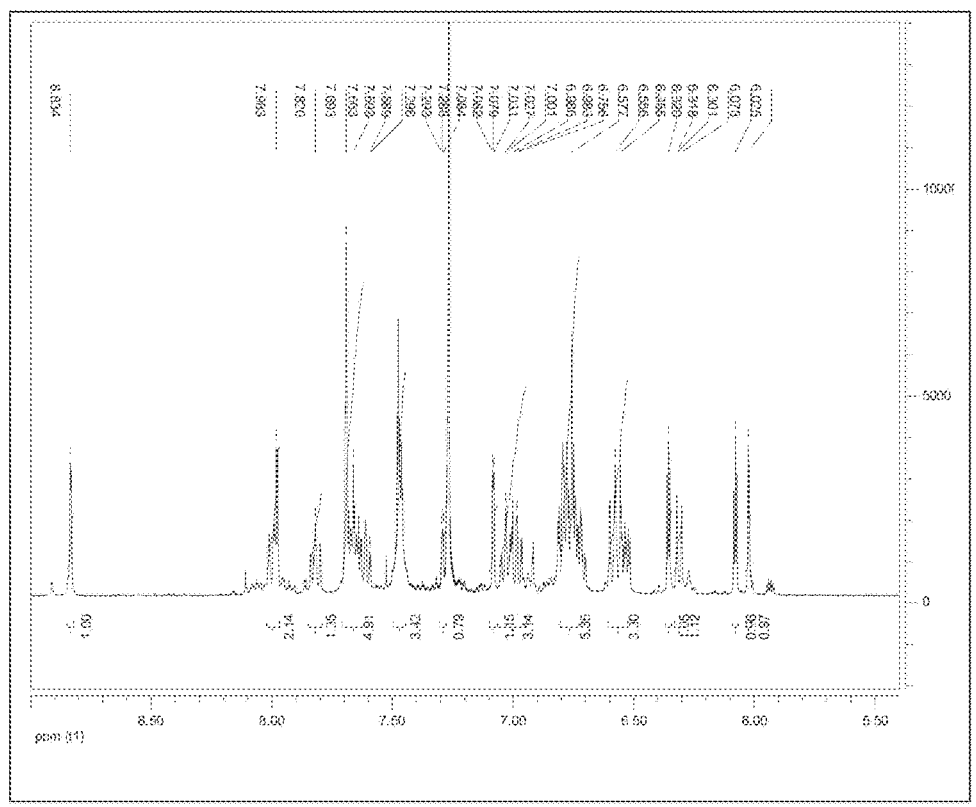
FIG. 32 is a $^1$H NMR (500 MHz, CD$_2$Cl$_2$) spectra of compound 3-fac.

FIG. 32 shows the $^1$H NMR spectra for compound 3-fac. The peaks for the $^1$H NMR (400 MHz, $CD_2Cl_2$, 298 K) spectra were at δ=8.83 (m, 1H), 7.99 (m, 2H), 7.82 (m, 1H) 7.59-7.69 (m, 5H), 7.46-7.48 (m, 3H), 7.30 (m, 1H), 6.96-7.03 (m, 3H), 6.72-6.81 (m, 5H), 6.52-6.60 (m, 3H), 6.36 (t, J=2.2 Hz, 1H), 6.31 (m, 1H), 6.08 (t, J=2.3 Hz, 1H), 6.03 (d, J=2.2 Hz, 1H).

Maldi-MS analysis indicated in a mass to charge (m/z) ratio of 791.23 ([M]$^+$, calculated: 791.18).

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound comprising a metal and a ligand $L_A$ selected from the group of ligands consisting of:

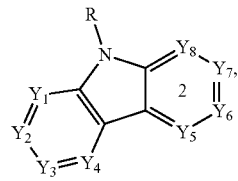

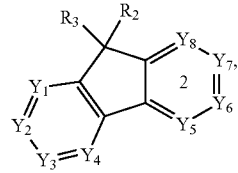

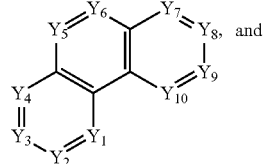

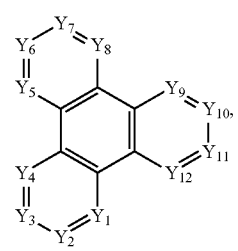

wherein $Y_1$, $Y_2$, $Y_3$, $Y_4$, $Y_5$, $Y_6$, $Y_7$, $Y_8$, $Y_9$, $Y_{10}$, $Y_{11}$, and $Y_{12}$ are independently selected from the group consisting of CH, C bonded to metal M, N, and C-APR$_1$'R$_1$", and the ligand $L_A$ is bidentate with a first bond to the metal M formed with the P-atom of the C-APR$_1$'R$_1$" and a second bond to the metal M formed with a ring carbon of ligand $L_{A5}$, ligand $L_{A6}$, ligand $L_{A7}$, or ligand $L_{A8}$; wherein the metal M has an atomic weight of at least 40;

wherein exactly one of $Y_1$ through $Y_8$ is C-APR$_1$'R$_1$" in $L_{A5}$ and $L_{A6}$, and exactly one of $Y_1$ through $Y_8$ is the ring carbon bonded to the metal;

wherein exactly one of $Y_1$ through $Y_{10}$ is C-APR$_1$'R$_1$" in $L_{A7}$, and exactly one of $Y_1$ through $Y_{10}$ is the ring carbon bonded to the metal;

wherein exactly one of $Y_1$ through $Y_{12}$ is C-APR$_1$'R$_1$" in $L_{A8}$, and exactly one of $Y_1$ through $Y_{12}$ is the ring carbon bonded to the metal;

wherein A is selected from the group consisting of a single bond, —CR$_A$R$_B$—, —NR$_A$—, —O—, —S— and —SiR$_A$R$_B$—;

wherein R, R$_1$', R$_1$", R$_2$, R$_3$, R$_4$, and R$_B$ are each independently selected from the group consisting of hydrogen, deuterium, alkyl, cycloalkyl, and aryl.

2. The compound of claim 1, wherein M is a metal selected from the group consisting of Ir, Rh, Re, Ru, Os, Pt, Au, and Cu.

3. The compound of claim 1, wherein R$_1$' and R$_1$" are each phenyl.

4. The compound of claim 1, wherein the compound has the formula M(L$_A$)$_m$(L$_B$)$_n$, wherein the ligand L$_B$ is a different ligand from the ligand L$_A$;

wherein m is an integer from 1 to the maximum number of ligands that may be coordinated to the metal M; and m+n is the maximum number of ligands that may be coordinated to the metal M, and the ligand $L_B$ is selected from the group of ligands consisting of:
$L_{B1}$
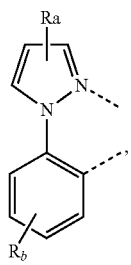
$L_{B2}$
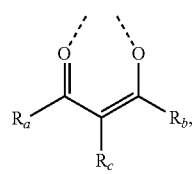
$L_{B3}$
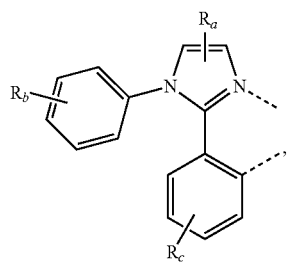
$L_{B4}$
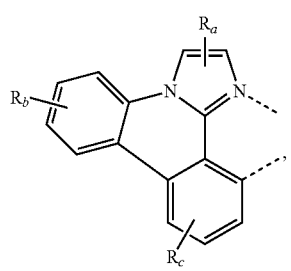
$L_{B5}$
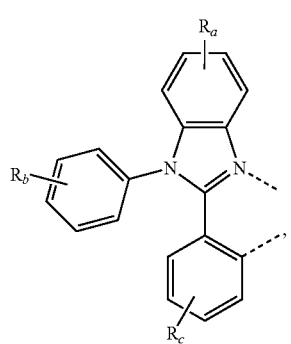
$L_{B6}$
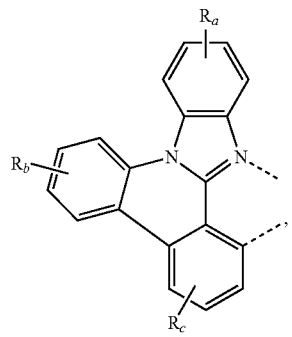
$L_{B7}$
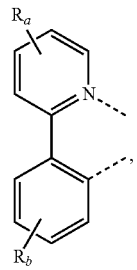
$L_{B8}$
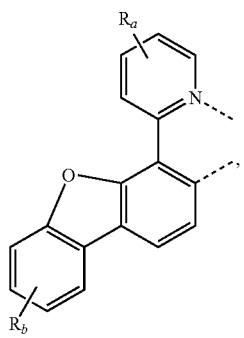
$L_{B9}$
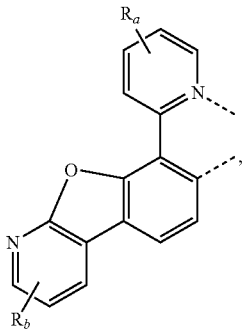
$L_{B10}$ -continued
L<sub>B12</sub>
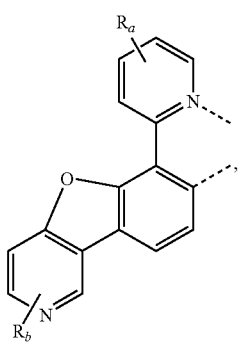
L<sub>B13</sub>
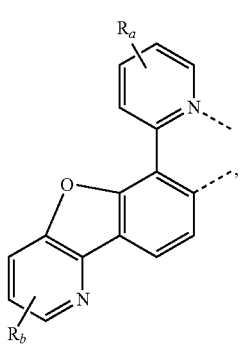
L<sub>B14</sub>
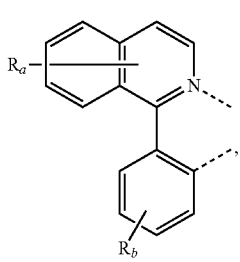
L<sub>B15</sub>
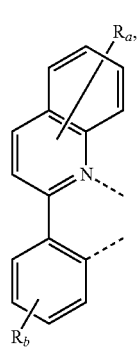
L<sub>B16</sub>
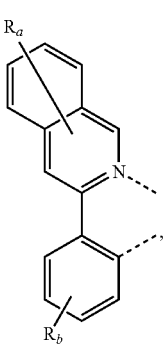
-continued
L<sub>B17</sub>
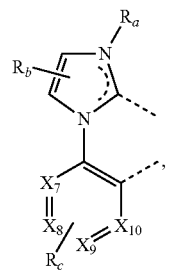
L<sub>B18</sub>
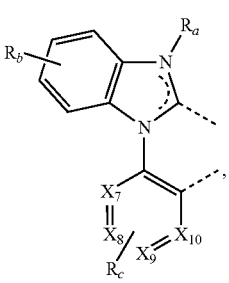
L<sub>B19</sub>
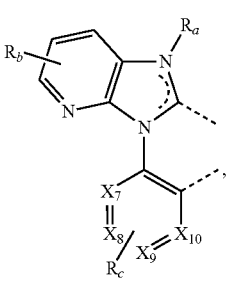
L<sub>B20</sub>
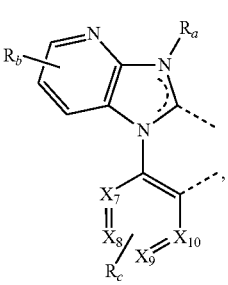
L<sub>B21</sub>
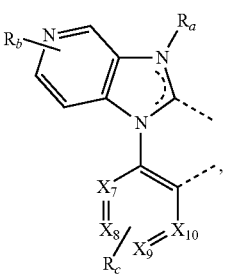

-continued

L$_{B22}$ 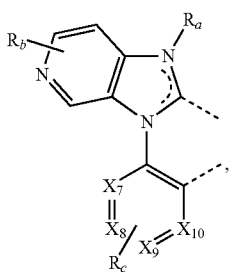

L$_{B23}$ 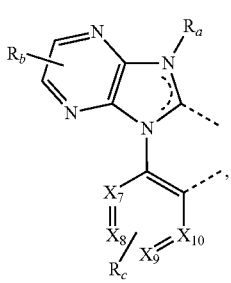

L$_{B24}$ 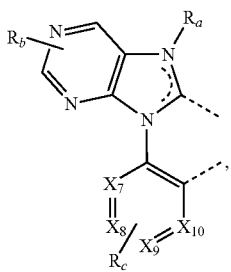

L$_{B25}$ 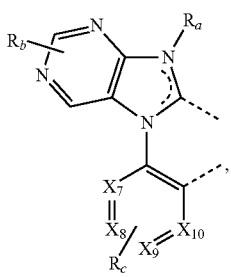

L$_{B26}$ 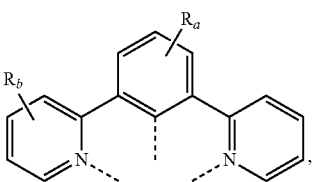

L$_{B28}$ 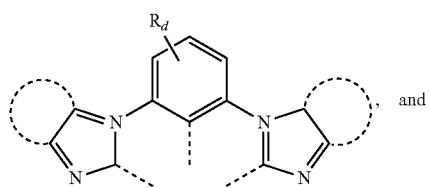 and

-continued

L$_{B29}$ 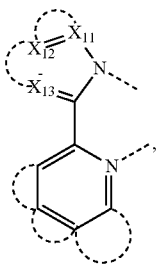

wherein:
$X_7$, $X_8$, $X_9$, and $X_{10}$ are independently selected from the group consisting of CH, and N;

$X_{11}$, $X_{12}$, and $X_{13}$ are independently selected from the group consisting of CH, CR', and N;

$R_a$, $R_b$, and $R_c$, may represent mono, di, tri, or tetra substitution, or no substitution;

$R_d$ may represent mono, di, or tri substitution, or no substitution;

R', $R_a$, $R_b$, $R_c$, $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, carboxylic acids, ester, nitrile, isonitrile, and phosphino; and two adjacent substituents of $R_a$, $R_b$, $R_c$, and $R_d$ are optionally joined to form a fused ring;

wherein dotted arcs of ligand L$_{B28}$ and ligand L$_{B29}$ represent optional fused rings, which can be cyclic, heterocyclic, aromatic, or heteroaromatic, and which can be further substituted; and if present, each end of each dotted arc is fused to a carbon atom.

5. The compound of claim 1, wherein the compound has the formula M(L$_A$)$_x$(L$_B$)$_y$(LC)$_z$, wherein the ligands L$_A$, L$_B$ and L$_C$ are three different ligands, and L$_C$ is a monodentate ligand;

x is 1, or 2;

y is 0, 1, or 2;

z is 0, 1, or 2; and wherein x+y+z is the oxidation state of the metal M.

6. The compound of claim 1, wherein the compound is homoleptic.

7. The compound of claim 6, wherein the compound has a facial configuration.

8. The compound of claim 6, wherein the compound has a meridional configuration.

9. The compound of claim 1, wherein ligand L$_A$ is selected from the group consisting of:

L$_{A5-1}$ 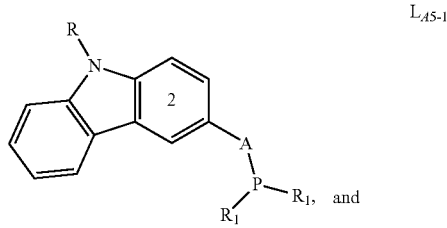

-continued

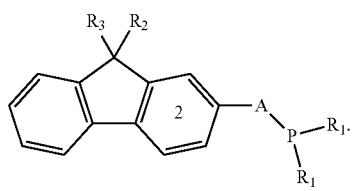
$L_{A6-1}$

10. The compound of claim 9, wherein the second bond between the metal and the ligand $L_A$ is formed by:
a carbon atom of Ring 2 of the ligands $L_{A5-1}$ and $L_{A6-1}$.

11. The compound of claim 1, wherein the compound has the formula $M(L_A)_m(L_B)_n$, wherein the ligand $L_B$ is a different ligand from the ligand $L_A$;
wherein m is an integer from 1 to the maximum number of ligands that may be coordinated to the metal M; and m+n is the maximum number of ligands that may be coordinated to the metal M, and the ligand $L_B$ is selected from the group of ligands consisting of:

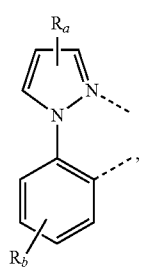
$L_{B1}$

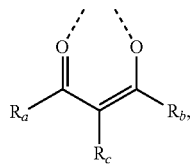
$L_{B2}$

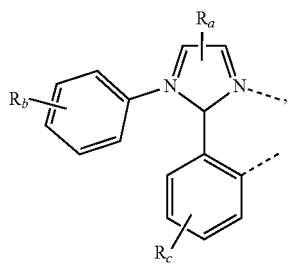
$L_{B3}$

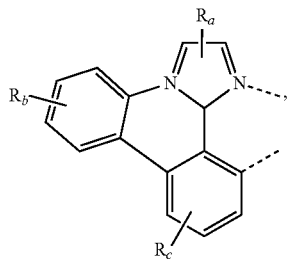
$L_{B4}$

-continued

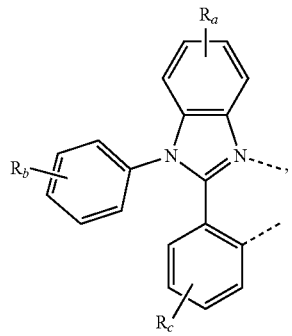
$L_{B5}$

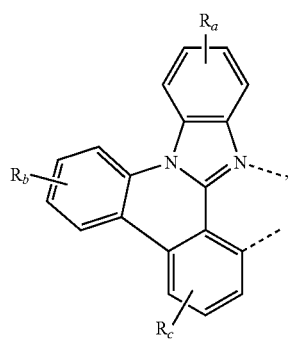
$L_{B6}$

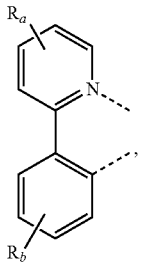
$L_{B7}$

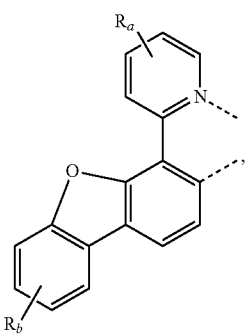
$L_{B8}$

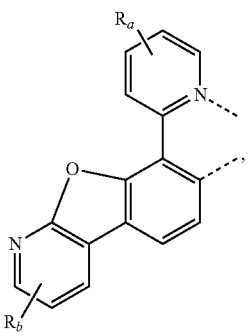
$L_{B9}$

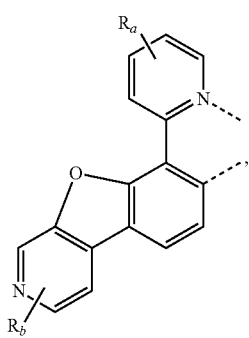 L_{B10}
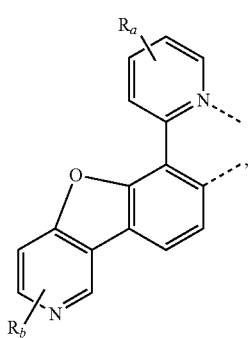 L_{B12}
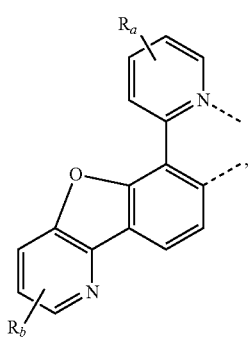 L_{B13}
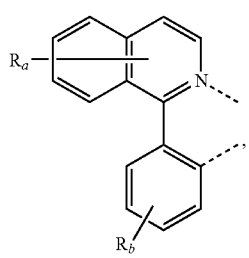 L_{B14}
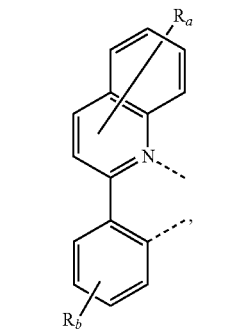 L_{B15}
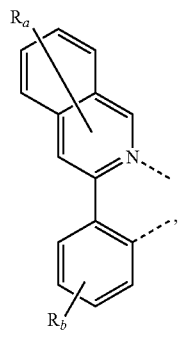 L_{B16}
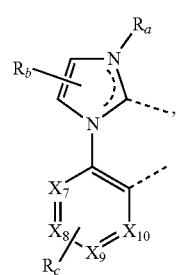 L_{B17}
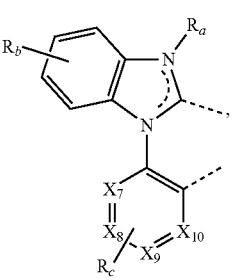 L_{B18}
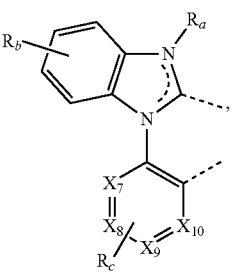 L_{B19}
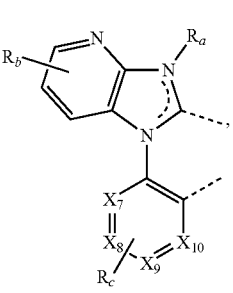 L_{B20}

$L_{B21}$ 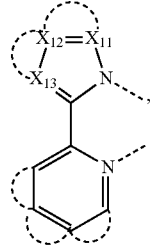

$L_{B22}$ 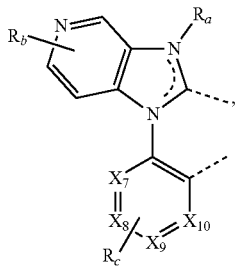

$L_{B23}$ 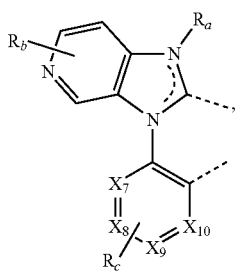

$L_{B24}$ 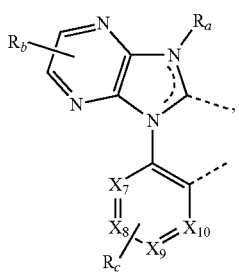

$L_{B25}$ 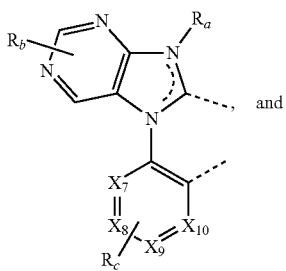, and $L_{B29}$ 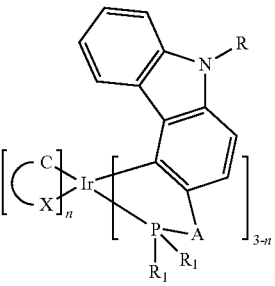, wherein:

$X_7$, $X_8$, $X_9$, and $X_{10}$ are independently selected from the group consisting of CH, and N;

$X_{11}$, $X_{12}$, and $X_{13}$ are independently selected from the group consisting of CH, CR', and N;

$R_a$, $R_b$, and $R_c$, may represent mono, di, tri, or tetra substitution, or no substitution;

R', $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, carboxylic acids, ester, nitrile, isonitrile, and phosphino; and two adjacent substituents of $R_a$, $R_b$, and $R_c$ are optionally joined to form a fused ring;

wherein dotted arcs of ligand $L_{B29}$ represent optional fused rings, which can be cyclic, heterocyclic, aromatic, or heteroaromatic, and which can be further substituted; and if present, each end of each dotted arc is fused to a carbon atom.

12. The compound of claim 11, where the compound is selected from the group consisting of:

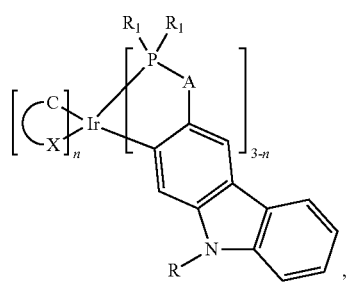

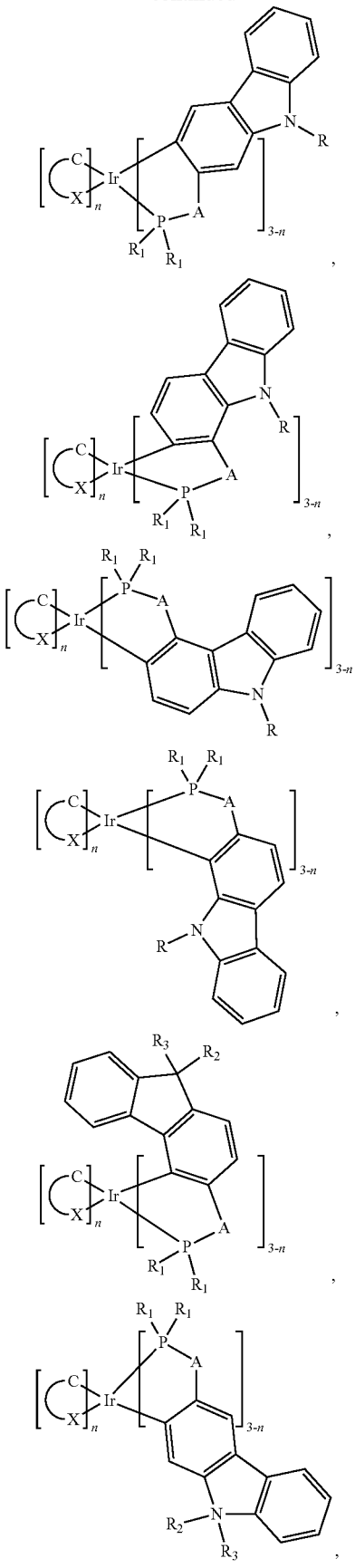
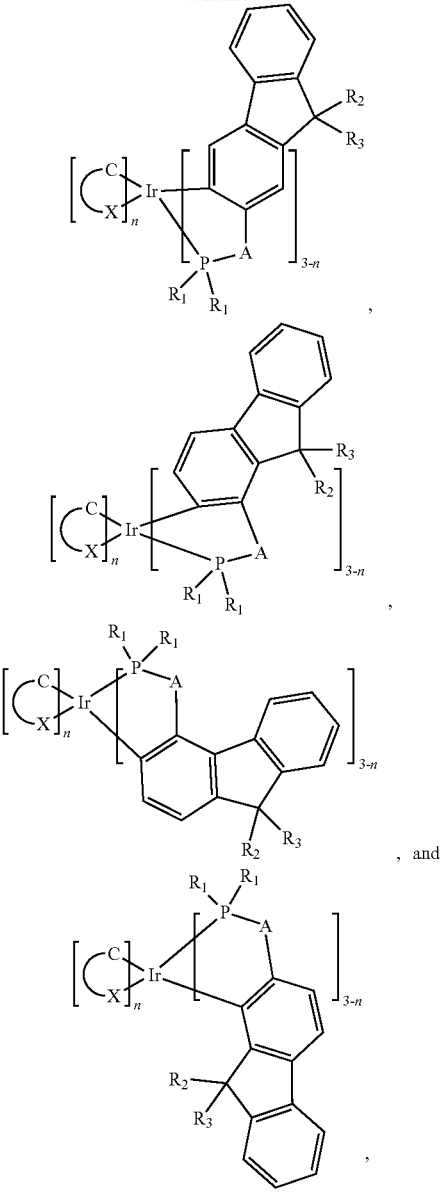
wherein
is selected from the group consisting of $L_{B1}$ through $L_{B10}$, $L_{B12}$ through $L_{B25}$, and $L_{B29}$,
wherein each $R_1$ is independently selected from the group consisting of hydrogen, deuterium, alkyl, cycloalkyl, and aryl, and
wherein n=0, 1, or 2.
13. A first device comprising an organic light emitting device, the organic light emitting device comprising:
an anode;
a cathode; and an organic layer, disposed between the anode and the cathode, comprising a compound comprising a metal and a ligand $L_A$ selected from the group of ligands consisting of:

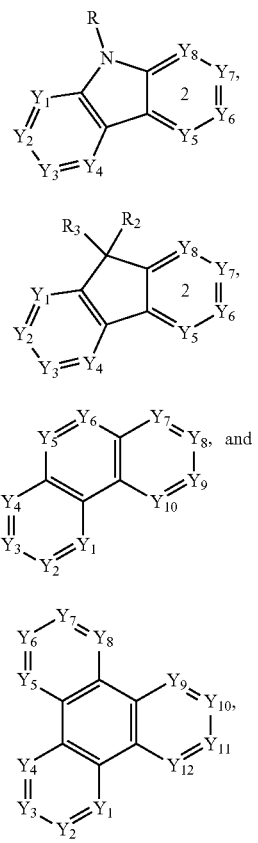

wherein $Y_1$, $Y_2$, $Y_3$, $Y_4$, $Y_5$, $Y_6$, $Y_7$, $Y_8$, $Y_9$, $Y_{10}$, $Y_{11}$, and $Y_{12}$ are independently selected from the group consisting of CH, C bonded to metal M, N, and C-APR$_1$'R$_1$''', and the ligand $L_A$ is bidentate with a first bond to the metal M formed with the P-atom of the C-APR$_1$'R$_1$''' and a second bond to the metal M formed with a ring carbon of ligand $L_{A5}$, ligand $L_{A6}$, ligand $L_{A7}$, or ligand $L_{A8}$; wherein the metal M has an atomic weight of at least 40;

wherein exactly one of $Y_1$ through $Y_8$ is C-APR$_1$'R$_1$''' in $L_{A5}$ and $L_{A6}$, and exactly one of $Y_1$ through $Y_8$ is the ring carbon bonded to the metal;

wherein exactly one of $Y_1$ through $Y_{10}$ is C-APR$_1$'R$_1$''' in $L_{A7}$, and exactly one of $Y_1$ through $Y_{10}$ is the ring carbon bonded to the metal;

wherein exactly one of $Y_1$ through $Y_{12}$ is C-APR$_1$'R$_1$''' in $L_{A8}$, and exactly one of $Y_1$ through $Y_{12}$ is the ring carbon bonded to the metal;

wherein A is selected from the group consisting of a single bond, —CR$_A$R$_B$—, —NR$_A$—, —O—, —S— and —SiR$_A$R$_B$—;

wherein R, R$_1$', R$_1$''', R$_2$, R$_3$, R$_A$, and R$_B$ are each independently selected from the group consisting of hydrogen, deuterium, alkyl, cycloalkyl, and aryl.

14. The first device of claim 13, wherein the first device is a consumer product.

15. The first device of claim 13, wherein the first device is an organic light-emitting device.

16. The first device of claim 13, wherein the first device comprises a lighting panel.

17. The first device of claim 13, wherein the organic layer is an emissive layer comprising a host and the compound is a non-emissive dopant.

18. The first device of claim 13, wherein the organic layer further comprises a host, and the host comprises a triphenylene containing benzo-fused thiophene or benzo-fused furan;

wherein any substituent in the host is an unfused substituent independently selected from the group consisting of $C_mH_{2m+1}$, $OC_mH_{2m+1}$, $OAr_1$, $N(C_mH_{2m+1})_2$, $N(Ar_1)(Ar_2)$, $CH=CH—C_mH_{2m+1}$, $C\equiv CC_mH_{2m+1}$, $Ar_1$, $Ar_1$-$Ar_2$, and $C_mH_{2m}$—$Ar_1$;

wherein m is from 1 to 10; and wherein $Ar_1$ and $Ar_2$ are independently selected from the group consisting of benzene, biphenyl, naphthalene, triphenylene, carbazole, and heteroaromatic analogs thereof.

19. The first device of claim 13, wherein the organic layer further comprises a host, and the host comprises at least one chemical group selected from the group consisting of carbazole, dibenzothiophene, dibenzofuran, dibenzoselenophene, azacarbazole, aza-dibenzothiophene, aza-dibenzofuran, and aza-dibenzoselenophene.

20. The first device of claim 13, wherein the organic layer further comprises a host, and the host is selected from the group consisting of:

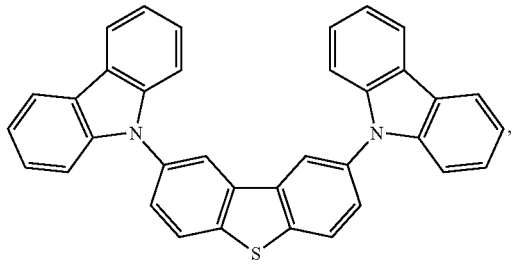

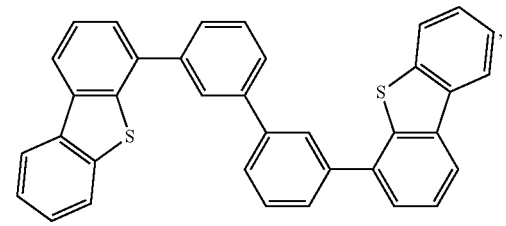

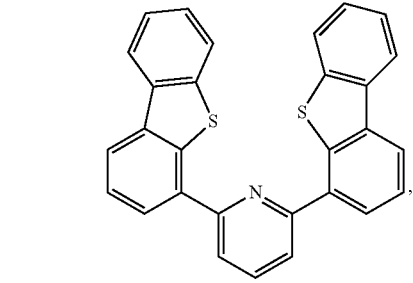

-continued
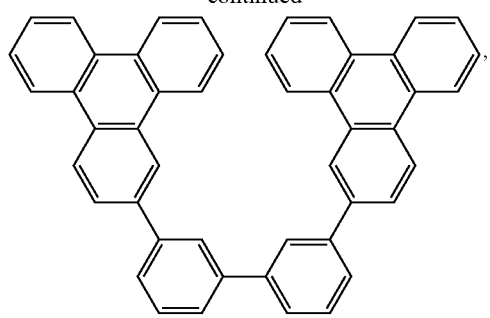
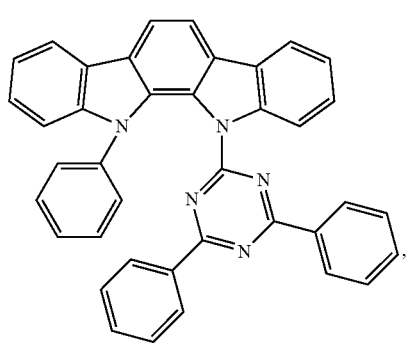
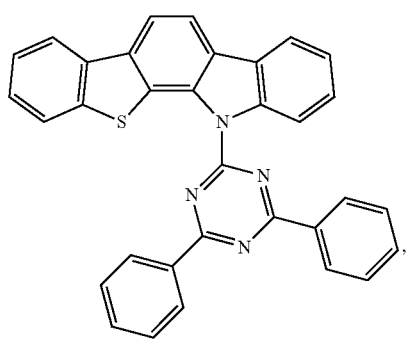
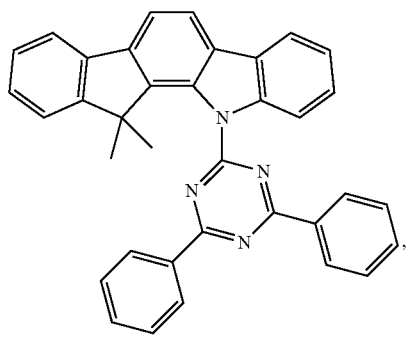
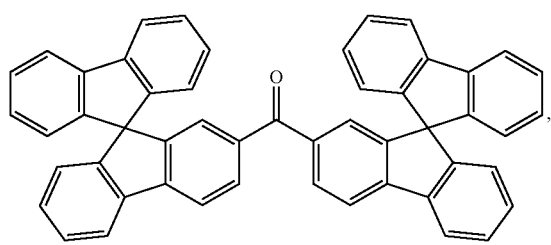
-continued
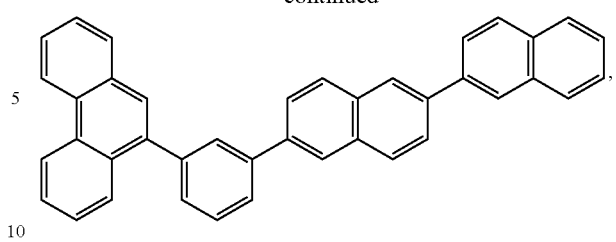
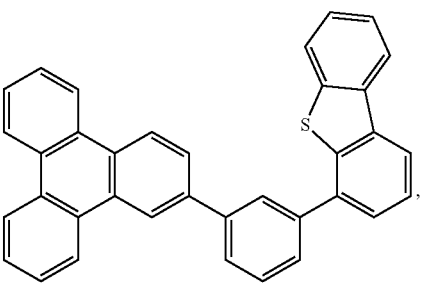
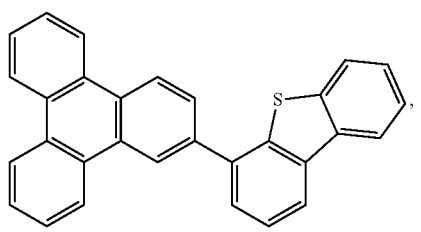 [SMILES: c1ccc2c(c1)sc1c(-c3ccc4c5ccccc5c5ccccc5c4c3)cccc12]
and combinations thereof.
21. A formulation comprising a compound comprising a metal and a ligand $L_A$ selected from the group of ligands consisting of:
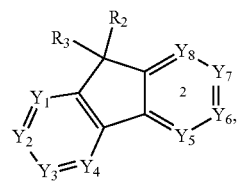
$L_{A5}$
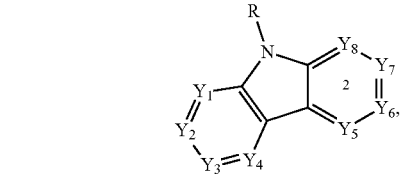
$L_{A6}$
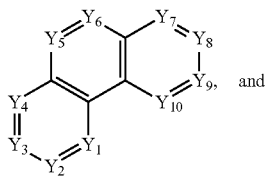
$L_{A7}$
and -continued

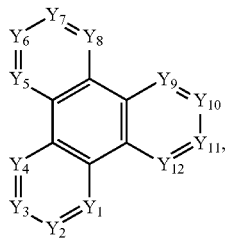

L_{A8} wherein $Y_1$, $Y_2$, $Y_3$, $Y_4$, $Y_5$, $Y_6$, $Y_7$, $Y_8$, $Y_9$, $Y_{10}$, $Y_{11}$, and $Y_{12}$ are independently selected from the group consisting of CH, C bonded to metal M, N, and C-APR$_1'$R$_1''$, and the ligand $L_A$ is bidentate with a first bond to the metal M formed with the P-atom of the C-APR$_1'$R$_1''$ and a second bond to the metal M formed with a ring carbon of ligand $L_{A5}$, ligand $L_{A6}$, ligand $L_{A7}$, or ligand $L_{A8}$;

wherein the metal M has an atomic weight of at least 40;

wherein exactly one of $Y_1$ through $Y_8$ is C-APR$_1'$R$_1''$ in $L_{A5}$, and $L_{A6}$, and exactly one of $Y_1$ through $Y_8$ is the ring carbon bonded to the metal;

wherein exactly one of $Y_1$ through $Y_{10}$ is C-APR$_1'$R$_1''$ in $L_{A7}$, and exactly one of $Y_1$ through $Y_{10}$ is the ring carbon bonded to the metal;

wherein exactly one of $Y_1$ through $Y_{12}$ is C-APR$_1'$R$_1''$ in $L_{A8}$, and exactly one of $Y_1$ through $Y_{12}$ is the ring carbon bonded to the metal;

wherein A is selected from the group consisting of a single bond, —CR$_A$R$_B$—, —NR$_A$—, —O—, —S— and —SiR$_A$R$_B$—;

wherein R, R$_1'$, R$_1''$, R$_2$, R$_3$, R$_A$, and R$_B$ are each independently selected from the group consisting of hydrogen, deuterium, alkyl, cycloalkyl, and aryl.

* * * * *